(12) United States Patent
Yuan et al.

(10) Patent No.: US 11,205,502 B2
(45) Date of Patent: Dec. 21, 2021

(54) PROCESSING METHOD AND PROCESSING APPARATUS FOR EFFICACY OF COMBINED DRUG

(71) Applicant: Institute of radiation medicine, academy of military medical sciences, PLA., Beijing (CN)

(72) Inventors: Shoujun Yuan, Beijing (CN); Linna Li, Beijing (CN); Dexuan Yang, Beijing (CN)

(73) Assignee: Institute of radiation medicine, academy of military medical sciences, PLA., Beijing (CN)

( * ) Notice: Subject to any disclaimer, the term of this patent is extended or adjusted under 35 U.S.C. 154(b) by 629 days.

(21) Appl. No.: 15/764,334

(22) PCT Filed: Aug. 31, 2016

(86) PCT No.: PCT/CN2016/097514
§ 371 (c)(1),
(2) Date: Mar. 29, 2018

(87) PCT Pub. No.: WO2017/054609
PCT Pub. Date: Apr. 6, 2017

(65) Prior Publication Data
US 2018/0276347 A1 Sep. 27, 2018

(30) Foreign Application Priority Data
Sep. 30, 2015 (CN) .......................... 201510640075.0

(51) Int. Cl.
*G16C 20/30* (2019.01)
*G06N 7/00* (2006.01)
*G16Z 99/00* (2019.01)

(52) U.S. Cl.
CPC ............... *G16C 20/30* (2019.02); *G06N 7/00* (2013.01); *G16Z 99/00* (2019.02)

(58) Field of Classification Search
CPC .......... G16C 20/30; G16Z 99/00; G06N 7/00
See application file for complete search history.

(56) References Cited

U.S. PATENT DOCUMENTS

| 2003/0192560 A1 | 10/2003 | McMichael | |
| 2004/0132633 A1* | 7/2004 | Carter, Jr. ............ | G16H 20/10 514/1 |

(Continued)

FOREIGN PATENT DOCUMENTS

| CN | 101046831 A | 10/2007 |
| CN | 101339584 A | 1/2009 |

(Continued)

OTHER PUBLICATIONS

Tallarida, Ronald J. "An overview of drug combination analysis with isobolograms." Journal of Pharmacology and Experimental Therapeutics 319, No. 1 (2006): 1-7. (Year: 2006).*

(Continued)

*Primary Examiner* — Jesse P Frumkin
(74) *Attorney, Agent, or Firm* — Gang Yu

(57) ABSTRACT

Provided are a processing method and a processing apparatus for efficacy of a combined drug. The processing method includes: obtaining dose-effect curve band of expected additive effect of the combined drug; obtaining actual dose-effect relationship curve formed by actual effect value of the combined drug with a dose change of one target component drug in the combined drug; comparing a positional relationship between the actual dose-effect relationship curve and the dose-effect curve band; and outputting the efficacy of the combined drug as a synergistic effect when the actual dose-effect relationship curve is located above the dose-effect curve band, outputting the efficacy of the combined (Continued)

drug as an antagonistic effect when the actual dose-effect relationship curve is located below the dose-effect curve band, and outputting the efficacy of the combined drug as an additive effect when the actual dose-effect relationship curve is located within a range of the dose-effect curve band.

20 Claims, 11 Drawing Sheets

(56) References Cited

U.S. PATENT DOCUMENTS

| | | | |
|---|---|---|---|
| 2004/0138826 A1* | 7/2004 | Carter, Jr. | G16C 20/10 702/27 |
| 2004/0203043 A1* | 10/2004 | Scott | C40B 30/06 435/6.11 |
| 2006/0195215 A1 | 8/2006 | Suzuki et al. | |
| 2008/0075762 A1 | 3/2008 | Tardi et al. | |
| 2013/0231264 A1* | 9/2013 | Reichman | B01J 19/0046 506/9 |
| 2019/0121935 A1* | 4/2019 | Ho | G16C 20/30 |

FOREIGN PATENT DOCUMENTS

| | | | |
|---|---|---|---|
| CN | 101732329 A | 6/2010 | |
| CN | 102269755 A | 12/2011 | |
| CN | 103838967 A | 6/2014 | |
| CN | 105224799 A | 1/2016 | |
| EP | 3358481 A4 * | 6/2019 | G16C 20/30 |
| JP | 2003099535 A | 4/2003 | |
| JP | 2010524055 A | 7/2010 | |
| WO | 2005058373 A2 | 6/2005 | |

OTHER PUBLICATIONS

Tallarida, Ronald J. "Quantitative methods for assessing drug synergism." Genes & cancer 2, No. 11 (2011): 1003-1008. (Year: 2011).*

Foucquier, Julie, and Mickael Guedj. "Analysis of drug combinations: current methodological landscape." Pharmacology research & perspectives 3, No. 3 (2015): e00149. (Year: 2015).*

Julie Foucquier et al: "Analysis of drug combinations: current methodological landscape",Pharmacology Research & Perspectives, vol. 3, No. 3, pp. 1-11;abstract p. 4 col. 1, paragraph 2-p. 5 col. 1, paragraph 1.

R.J. Tallarida: "Quantitative Methods for Assessing Drug Synergism", Genes&Cancer, vol. 2, No. 11, pp. 1003-1008, abstract p. 1005 col. 1, paragraph 1-p. 1007 col. 1, paragraph 1; figure 2.

* cited by examiner

Fig. 1 obtain a dose-effect curve band of an expected additive effect of a combined drug, wherein the dose-effect curve band is enclosed by two equivalent dose-effect curves at the most periphery in multiple equivalent dose-effect curves, each of the equivalent dose-effect curves is a curve established by taking a dose of one target component drug in the combined drug as a horizontal coordinate and an expected additive effect obtained by equivalently converting the combined drug into any component drug as a vertical coordinate, and the equivalent conversion is performed according to a drug sequence of each component drug in the obtained combined drug ⎯⎯ 202 obtain an actual dose-effect relationship curve formed by an actual effect value of the combined drug with a dose change of the one target component drug in the combined drug; ⎯⎯ 204 compare a positional relationship between the actual dose-effect relationship curve and the dose-effect curve band; and ⎯⎯ 206 output the efficacy of the combined drug as a synergistic effect when the actual dose-effect relationship curve is located above the dose-effect curve band, output the efficacy of the combined drug as an antagonistic effect when the actual dose-effect relationship curve is located below the dose-effect curve band, and output the efficacy of the combined drug as an additive effect when the actual dose-effect relationship curve is located within a range of the dose-effect curve band. ⎯⎯ 208

NX concentration in
combined group (fixed proportion)

NX concentration in combined
group (fixed proportion)

vincristine /B fluorouracil/C etoposide (A) concentration in an ABC combined group etoposide (A) concentration in an ABC combined group ated at the content here. 3) Mutual effect among drug effects, which refers to enhanced or weakened drug effects when action mechanisms are different or similar drugs are combined. And 4) influences of a drug administration sequence (sequence); when multiple drugs are combined, there may be different drug administration sequences such that states of tissue cells are changed differently and the drug effects are also different to some extent.

PROCESSING METHOD AND PROCESSING APPARATUS FOR EFFICACY OF COMBINED DRUG

TECHNICAL FIELD

The present disclosure relates to the field of biomedicines, and more particularly, to a processing method and a processing apparatus for efficacy of a combined drug.

BACKGROUND

At present, a basic route to research and develop a new drug is to screen a candidate compound and optimize a primer for a disease related target and then is approved to put into a market after druggability research, pre-clinical evaluation and clinical trials. Such research mode based on "a single target, a single disease and a single drug" becomes increasingly difficult in therapeutic use, particularly to research and develop a single-structure compound drug for the single target. Many serious diseases difficult to be treated are generally rooted in multiple targets and multiple links and only can be treated effectively via multiple procedures. However, to develop a new single-structure compound drug for the multiple procedures is hardly possible. From the perspective of the feasibility of solving the problem and an actual effect, only to give a patient a combined drug or research and develop a new compound drug are broad paths for disease treatment and new drug research and development.

Moreover, it is rare to use a single drug in modern medical practices and is frequent to use multiple drugs such as 2-3 drugs at least, 7-8 drugs at most or even 10 drugs. A drug combined application is one of the most effective treatment means for the disease. In traditional Chinese medicine, it is very common to combine multiple animal, plant or mineral components or to form a fixed prescription. Motivations for the multiple-drug combined application include the followings: the disease treatment often needs to direct at multiple links or multiple targets; the patient is often suffered from multiple diseases; the treatment for any disease needs etiological treatment and symptomatic treatment; indications and therapeutic windows for any drug are limited and have toxicity and side effect in different natures and different degrees. Therefore, the combined drug administration is to obtain the maximum therapeutic effect and alleviate the toxicity and side effect to the great extent. For the treatment of some serious diseases such as malignant tumors, infectious diseases and cardiovascular and cerebrovascular diseases, the therapeutic effect of drug combination is very notable. In research and development of the new drug, the research and development of various new compound preparations, as a matter of fact, are to combine multiple drugs exerting the best therapeutic use and immobilize reasonably and maximally.

However, when the multiple drugs are combined, interactions among the drugs includes: 1) mutual effect of the drugs in physicochemical properties, which refers to a change in the physicochemical properties when the drugs are mixed and combined. A national drug competent department has specified strict application regulations in incompatibility of clinical drugs, such as a drug incompatibility table. 2) Mutual effect to metabolism disposal capability of a body, which refers to that one drug affects a tissue and an organ responsible for medicine metabolism disposal and has an important influence on an in vivo process of another drug, thereby causing a change in efficacy and toxicity. Guiding principles issued by home and abroad drug administration departments on influences of drug interactions are directed at the content here. 3) Mutual effect among drug effects, which refers to enhanced or weakened drug effects when action mechanisms are different or similar drugs are combined. And 4) influences of a drug administration sequence (sequence); when multiple drugs are combined, there may be different drug administration sequences such that states of tissue cells are changed differently and the drug effects are also different to some extent.

Specific management guidelines have been stipulated by the drug administration department for the previous two interactions. However, for the later two interactions, when related drugs are combined, there lack specific guidance methods for the quantitative detection of synergistic, additive and antagonistic effects. Regardless of whatever level on which the drug interaction occurs, the effect of the drug will change and appears to be synergistic, additive and antagonistic.

For definitions of the synergistic, additive and antagonistic effects, it is well accepted that the synergistic effect is an additive effect with an actual efficacy greater than an expected efficacy, the additive effect is the additive effect with the actual efficacy equal to the expected efficacy, and the antagonistic effect is the additive effect with the actual efficacy smaller than the expected efficacy. From the level of the drug effect, the synergistic and antagonistic effects refer to there have interactions among the drugs in fact. The additive effect refers to there is no interaction and thus the definition of the additive effect of the drug is extended into a zero interaction. From a perspective of a dose change of the drug, the synergistic effect refers to that a drug combined dose is smaller than an expected combined dose under equal efficacy levels, the additive effect refers to that the drug combined dose is equal to the expected combined dose under the equal efficacy levels, and the antagonistic effect refers to that the drug combined dose is greater than the expected combined dose under the equal efficacy levels. Therefore, the effect caused by the combined use of the multiple drugs and the change in the drug dose are two sides of a coin as a matter of fact and both can be used for defining the synergistic, additive and antagonistic effects of the multiple drugs in the combined use.

For above statements on the additive effect, whether based on the efficacy or based on the dose, an expected additive effect for a determined drug combination is a fixed value. By comparing an actual effect detected value in the combined use with a value of the expected additive effect, the synergistic, additive and antagonistic effects are quantitatively calculated and judged. However, when multiple drugs are combined, dose-effect curves of each drug member and the combined drugs are complex. With the combined application of two drugs of a drug A and a drug B as an example, conditions actually confronted by each drug member and the complex conditions of the dose-effect relationship curves are listed as follows:

1) Condition 1: the drug A has the effect and the drug B has no effect. When the drug A and the drug B are combined, the effect of the drug A changes obviously. Under such a condition, the dose-effect curve of the expected drug additive effect of the two drugs in the combined use is a dose-effect curve of the single-use drug A and thus it is relatively easy to quantify the synergistic effect or the antagonistic effect of the drugs in the combined use.

2) Condition 2: both the drug A and the drug B have no effect. The drug effect is generated when the drug A and the drug B are combined. Under such a condition, the expected drug additive effect curve of the two drugs in the combined use is a straight line with the effect value being zero, and thus it is relatively easy to quantify the synergistic effect of the drugs in the combined use.

3) Condition 3: the drug A has the effect and the drug B also has the effect. When the drug A and the drug B are combined, the respective drug effect changes certainly and is neither different from the effect of the single-use drug A nor different from the effect of the single-use drug B. The dose-effect curve of each drug member is independent from each other and also is interactive to each other. To determine the expected additive effect curve is very difficult and the confronted drug dose-effect relationship curves are set forth hereinafter:

dose-effect relationship curve when the drug A is in the single use;

dose-effect relationship curve when the drug B is in the single use;

dose-effect curve of the drug A when the drugs A and B are combined at a fixed proportion;

dose-effect curve of the drug B when the drugs A and B are combined at a fixed proportion;

dose-effect curve of the drug B when the drug A is combined with the drug B at a fixed dose;

dose-effect curve of the drug A when the drug B is combined with the drug A at a fixed dose.

4) If there is a relatively large difference between action modes of the two drugs, it is inevitable to change the dose-effect relationship due to different drug administration sequence (sequential) manners and thus the complexity is greatly increased.

5) If three or more drugs are combined, the change in the drug dose-effect curve is more complex.

There are many calculation methods in literatures on whether the efficacy is the synergistic, additive or antagonistic effect when multiple drugs are combined over the last hundred years. For example, Greco W R concluded and summarized 13 or more calculation methods on the synergistic and antagonistic effects in an overview. In recent 20 years, there are relatively less development and progress on new methods. Currently, it is well accepted that the typical methods still are an equivalent line additive model of Loewe and an independent model of Bliss.

The equivalent line additive model of Loewe specifically is as follows: drug doses $D_A$ and $D_g$ of two drugs A and B at an effect level are respectively labeled on an X axis and a Y axis in a rectangular coordinate system, and a straight line at two points are connected to obtain an intercepted straight-line equation:

$$\frac{x}{D_A} + \frac{y}{D_B} = 1.$$

It is pointed by Loewe that when the two drugs are combined respectively at relatively small doses $d_A$ and $d_g$ and reach to an effect generated by the single-use drug at the dose $D_A$ or $D_g$, there exists the following relationships:

$$\frac{d_A}{D_A} + \frac{d_B}{D_B} = 1,$$

additive effect;

$$\frac{d_A}{D_A} + \frac{d_B}{D_B} < 1,$$

synergistic effect;

$$\frac{d_A}{D_A} + \frac{d_B}{D_B} > 1,$$

antagonistic effect.

The equivalent line additive model skillfully avoids the difficult problem on how to calculate the expected additive effect. The synergistic, additive and antagonistic effects of the drugs are evaluated from the perspective of equal efficacy and reduced combined dose. Under the equal effect, the different dose combinations are described into a straight line. Through coordinate points of different combined doses and positional relationship with the straight line, the synergistic, additive or antagonistic effect is judged. The calculation method is widely used. However, with a limitable application range, it only can be used in two drugs with similar action modes. By viewing a "dose ratio" as an "effect ratio", it only can be used in evaluation of the combined application at the fixed proportion and is very difficult to evaluate the combined application of more drugs.

The independent model of Bliss specifically is as follows: effects of the drug A and the drug B are qualitative response data and a dose range of the drug effect is 0-1. By viewing the drug effects of the two drugs as independent events and by virtue of a probability addition calculation formula $P_{AB}=P_A+P_B-P_A \times P_B$, it is concluded that the additive effect of the drugs in the combined use is $E_{AB}=E_A+E_B-E_A \times E_B$ and there exists the following relationships:

$$\frac{E_{AB}}{E_A + E_B - E_A \times E_B} = 1,$$

additive effect;

$$\frac{E_{AB}}{E_A + E_B - E_A \times E_B} > 1,$$

synergistic effect;

$$\frac{E_{AB}}{E_A + E_B - E_A \times E_B} < 1,$$

antagonistic effect.

The independent model method of Bliss introduces a probability addition formula and is used in combined-use analysis of qualitative response drugs. However, the method lacks a support for respective dose-effect relationships of the drug A and the drug B, and only views the combined use of the two drugs as addition of probabilities of two isolated events. A Jin's method used in China more is originated from the model. However, the model does not meet a basic rule of the drug dose-effect relationship.

The rest methods mostly are based on deduction and evolution of the above two methods (Such as an equivalent linear graphic method, a Bürgi formula method, a grade analysis method, a median effect method, an effect surface model, a Jin's formula method and a grade product method). Furthermore, some calculation methods has very complex mathematical formulas, the key parameters are set often depending on experience of a user, the calculation is troublesome, and related data on an effect change in combined use of multiple drugs are difficult to be accurately calculated.

Therefore, methods for evaluating efficacy/toxic effect of multiple drugs in combined use mostly are stayed in simple quantitative comparison between a combined-use group and a single-use group of the drugs. For evaluation of effect of two drugs in the combined use, the efficacy of the combined use of the two drugs at a fixed proportion only can be calculated under a certain condition using the equivalent line additive model of Loewe and related models. Qualitative response data can be calculated using the independent model of Bliss. In additional, there further has a simpler method, that is, to fix a dose of one drug and adjust a dose of the other drug to perform a comparison test. For research and development of other drug combination manners, a combined application of more drug members, a new multi-component drug and a complex compound preparation, there lacks a reliable efficacy/toxic effect quantitative calculation method.

Therefore, based on the above complex conditions, when multiple drugs are combined, how to quantitatively evaluate an effect change due to combined application of the multiple drugs, and how to determine that the drug effect is synergistic, additive and antagonistic and to perform quantitative calculation haven't yet been solved for a long term.

SUMMARY

The present disclosure is mainly intended to provide a processing method and a processing apparatus for efficacy of a combined drug, so as to solve the technical problem that a drug effect is determined difficulty when multiple drugs are in combined use in the conventional art.

Definitions

Combined drug: in the present disclosure, the combined drug refers to multiple drugs for combined use. The combined drug includes different types of drugs according to drug types in the combined use. When two drugs are in the combined use, the combined drug refers to the two drugs. When three drugs are in the combined use, the combined drug refers to the three drugs. When more than three drugs are in the combined use, the combined drug refers to the more than three drugs. The combined use, combination, combined application and compatibility in the present disclosure all are the meaning of the combined use. In embodiments, a combined group formed by specific different drugs in terms of different combined use conditions is also the meaning of the combined drug.

Dose-effect relationship: it refers to that a drug dose is directly proportional to a drug effect in a certain dose range, and such relationship is the dose-effect relationship.

Dose-effect relationship curve: it refers to a curve quantitatively reflecting a rule of the drug effect with a change in the drug dose or in a concentration.

Dose combination index: by drawing a vertical line along a determined combined dose point on a horizontal coordinate axis, points crossed with a dose-effect curve band respectively are a minimum value and a maximum value of an expected additive effect under the combined dose. By comparing an actual efficacy value of the combined dose with the maximum value and the minimum value in an additive efficacy range, a $CI_{d1}$ and a $CI_{d2}$ are calculated.

Effect combination index: by drawing a straight line parallel to a horizontal axis along a determined efficacy point on a vertical coordinate axis, points crossed with the dose-effect curve band respectively are a minimum value and a maximum value of a dose given by an expected additive effect generated under an efficacy level. By comparing a combined dose generating the efficacy level actually with a minimum value and a maximum value of an additive dose, a $CI_{e1}$ and a $CI_{e2}$ are calculated.

To this end, according to one aspect of the present disclosure, there is provided a processing method for efficacy of a combined drug. The processing method includes: obtaining a dose-effect curve band of an expected additive effect of the combined drug, wherein the dose-effect curve band is enclosed by two equivalent dose-effect curves at the most periphery in multiple equivalent dose-effect curves, each of the equivalent dose-effect curves is a curve established by taking a dose of one target component drug in the combined drug as a horizontal coordinate and an expected additive effect obtained by equivalently converting the combined drug into any component drug as a vertical coordinate, and the equivalent conversion is performed according to a drug sequence of each component drug in the obtained combined drug; obtaining an actual dose-effect relationship curve formed by an actual effect value of the combined drug with a dose change of the one target component drug in the combined drug; comparing a positional relationship between the actual dose-effect relationship curve and the dose-effect curve band; and outputting the efficacy of the combined drug as a synergistic effect when the actual dose-effect relationship curve is located above the dose-effect curve band, outputting the efficacy of the combined drug as an antagonistic effect when the actual dose-effect relationship curve is located below the dose-effect curve band, and outputting the efficacy of the combined drug as an additive effect when the actual dose-effect relationship curve is located within a range of the dose-effect curve band.

Further, the combined drug includes a first component drug A and a second component drug B. Before the step of obtaining the dose-effect curve band of the expected additive effect of the combined drug, the processing method further includes a step of establishing multiple equivalent dose-effect curves, wherein the step of establishing the multiple equivalent dose-effect curves includes: obtaining a first dose-effect relationship curve $Y=f(x)$ of the first component drug A; obtaining a second dose-effect relationship curve $Y=g(x)$ of the second component drug B; finding or calculating an effect value $f(Am)$ of the first component drug A under a combined dose Am on the first dose-effect relationship curve $Y=f(x)$; finding or calculating an equivalent dose value Bm same as the effect value $f(Am)$ and corresponding to an effect value $g(Bm)$ of the second component drug B on the second dose-effect relationship curve $Y=g(x)$; calculating a dose sum $(Bn+Bm)$ of a combined dose Bn and the equivalent dose Bm of the second component drug B; finding or calculating a corresponding effect value $g(Bn+Bm)$ when the dose of the second component drug B on the second dose-effect relationship curve $Y=g(x)$ is the dose sum $(Bn+Bm)$; converting the effect value $g(Bn+Bm)$ into an expected additive effect value $Y(Am+Bn)$ of the combined drug; establishing a first equivalent dose-effect curve $Y(Am+Bn)=g(Bn+Bm)$ of the expected additive effect value $Y(Am+Bn)$ of the combined drug with a dose change of the first component drug A; finding or calculating an effect value $g(Bn)$ of the second component drug B under a combined dose Bn on the second dose-effect relationship curve Y=g(x); finding or calculating an equivalent dose value An same as the effect value g(Bn) and corresponding to an effect value f(An) of the first component drug A on the first dose-effect relationship curve Y=f(x); calculating a dose sum (Am+An) of a combined dose Am and the equivalent dose An of the first component drug A; finding or calculating a corresponding effect value f(Am+An) when the dose of the first component drug A on the first dose-effect relationship curve Y=f(x) is the dose sum (Am+An); converting the effect value f(Am+An) into the expected additive effect value Y(Am+Bn) of the combined drug; establishing a second equivalent dose-effect curve Y(Am+Bn)=f(Am+An) of the expected additive effect value of the combined drug with the dose change of the first component drug A.

Further, when the efficacy output result of the combined drug is the synergistic effect, after the step of outputting the efficacy of the combined drug as the synergistic effect, the processing method further includes: calculating a corresponding first dose range of the one target component drug when the actual dose-effect relationship curve is located above the dose-effect curve band; and outputting the first dose range as a synergistic dose range of the one target component drug.

Further, after outputting the synergistic dose range of the one target component drug, the processing method further includes: obtaining a combined relationship between the one target component drug and rest component drugs in the combined drug; calculating synergistic dose ranges of the rest component drugs in the combined drug under a combined condition according to the combined relationship; and outputting the synergistic dose ranges of the rest component drugs.

Further, when the efficacy output result of the combined drug is the antagonistic effect, after the step of outputting the efficacy of the combined drug as the antagonistic effect, the processing method further includes: calculating a corresponding second dose range of the one target component drug when the actual dose-effect relationship curve is located below the dose-effect curve band; and outputting the second dose range as an antagonistic dose range of the one target component drug.

Further, after outputting the antagonistic dose range of the one target component drug, the processing method further includes: obtaining a combined relationship between the one target component drug and rest component drugs in the combined drug; calculating antagonistic dose ranges of the rest component drugs in the combined drug under a combined condition according to the combined relationship; and outputting the antagonistic dose ranges of the rest component drugs.

Further, when the efficacy output result of the combined drug is the additive effect, after the step of outputting the efficacy of the combined drug as the additive effect, the processing method further includes: calculating a corresponding third dose range of the one target component drug when the actual dose-effect relationship curve is located within the range of the dose-effect curve band; and outputting the third dose range as an additive dose range of the one target component drug.

Further, after outputting the additive dose range of the one target component drug, the processing method further includes: obtaining a combined relationship between the one target component drug and rest component drugs in the combined drug; calculating additive dose ranges of the rest component drugs in the combined drug under a combined condition according to the combined relationship; and outputting the additive dose ranges of the rest component drugs.

Further, the step of comparing the positional relationship between the actual dose-effect relationship curve and the dose-effect curve band includes: obtaining a minimum value and a maximum value of an expected additive effect of a corresponding combined drug in a range of the dose-effect curve band under a specific combined dose of the one target component drug; obtaining an actual effect value of the corresponding combined drug on the actual dose-effect relationship curve under the specific combined dose of the one target component drug; calculating a first ratio of the actual effect value to the minimum value of the expected additive effect; calculating a second ratio of the actual effect value to the maximum value of the expected additive effect; respectively labeling the first ratio and the second ratio as $CI_{d1}$ and $CI_{d2}$; if the $CI_{d1}$ and the $CI_{d2}$ both are greater than 1, determining that the actual dose-effect relationship curve is located above the dose-effect curve band and the combined use is synergistic; if the $CI_{d1}$ and the $CI_{d2}$ both are smaller than 1, determining that the actual dose-effect relationship curve is located below the dose-effect curve band and the combined use is antagonistic; and if either the $CI_{d1}$ or the $CI_{d2}$ is greater than or equal to 1 or is smaller than or equal to 1, determining that the actual dose-effect relationship curve is located within the range of the dose-effect curve band.

Further, after the step of respectively labeling the first ratio and the second ratio as the $CI_{d1}$ and the $CI_{d2}$, the processing method further includes a step of outputting the $CI_{d1}$ and the $CI_{d2}$.

Further, the step of comparing the positional relationship between the actual dose-effect relationship curve and the dose-effect curve band includes: obtaining a minimum value and a maximum value of corresponding doses of the one target component drug when the combined drug generates a specific effect on the dose-effect curve band; obtaining an actual combined dose required when the combined drug generates the specific effect on the actual dose-effect relationship curve; calculating a third ratio of the actual combined dose to the minimum value; calculating a fourth ratio of the actual combined dose to the maximum value; respectively labeling the third ratio and the fourth ratio as $CI_{e1}$ and $CI_{e2}$; if the $CI_{e1}$ and the $CI_{e2}$ both are smaller than 1, determining that the actual dose-effect relationship curve is located above the dose-effect curve band; if the $CI_{e1}$ and the $CI_{e2}$ both are greater than 1, determining that the actual dose-effect relationship curve is located below the dose-effect curve band; and if either the $CI_{e1}$ or the $CI_{e2}$ is greater than or equal to 1 or is smaller than or equal to 1, determining that the actual dose-effect relationship curve is located within the range of the dose-effect curve band.

Further, after the step of respectively labeling the third ratio and the fourth ratio as the $CI_{e1}$ and the $CI_{e2}$, the processing method further includes a step of outputting the $CI_{e1}$ and the $CI_{e2}$.

According to another aspect of the present disclosure, there is provided a processing apparatus for efficacy of a combined drug. The processing apparatus includes: a first obtaining module, configured to obtain a dose-effect curve band of an expected additive effect of the combined drug, wherein the dose-effect curve band is enclosed by two equivalent dose-effect curves at the most periphery in multiple equivalent dose-effect curves, each of the equivalent dose-effect curves is a curve established by taking a dose of one target component drug in the combined drug as a horizontal coordinate and an expected additive effect obtained by equivalently converting the combined drug into any component drug as a vertical coordinate, and the equivalent conversion is performed according to a drug sequence of each component drug in the obtained combined drug; a second obtaining module, configured to obtain an actual dose-effect relationship curve formed by an actual effect value of the combined drug with a dose change of the one target component drug in the combined drug; a first comparison module, configured to compare a positional relationship between the actual dose-effect relationship curve and the dose-effect curve band; and a first output module, configured to output the efficacy of the combined drug as a synergistic effect when the actual dose-effect relationship curve is located above the dose-effect curve band; a second output module, configured to output the efficacy of the combined drug as an antagonistic effect when the actual dose-effect relationship curve is located below the dose-effect curve band; and a third output module, configured to output the efficacy of the combined drug as an additive effect when the actual dose-effect relationship curve is located within a range of the dose-effect curve band.

Further, the combined drug includes a first component drug A and a second component drug B. The processing apparatus further includes an equivalent dose-effect curve establishment module, the equivalent dose-effect curve establishment module being configured to establish multiple equivalent dose-effect curves before a step that the first obtaining module obtains the dose-effect curve band of the expected additive effect of the combined drug. The equivalent dose-effect curve establishment module includes: a first obtaining module, configured to obtain a first dose-effect relationship curve $Y=f(x)$ of the first component drug A; a second obtaining module, configured to obtain a second dose-effect relationship curve $Y=g(x)$ of the second component drug B; a first finding module, configured to find or calculate an effect value $f(Am)$ of the first component drug A under a combined dose $Am$ on the first dose-effect relationship curve $Y=f(x)$; a second finding unit, configured to find or calculate an equivalent dose value $Bm$ same as the effect value $f(Am)$ and corresponding to an effect value $g(Bm)$ of the second component drug B on the second dose-effect relationship curve $Y=g(x)$; a first calculation unit, configured to calculate a dose sum $(Bn+Bm)$ of a combined dose $Bn$ and the equivalent dose $Bm$ of the second component drug B; a third finding unit, configured to find or calculate a corresponding effect value $g(Bn+Bm)$ when the dose of the second component drug B on the second dose-effect relationship curve $Y=g(x)$ is the dose sum; a first conversion unit, configured to convert the effect value $g(Bn+Bm)$ into an expected additive effect value $Y(Am+Bn)$ of the combined drug; a first curve establishment unit, configured to establish a first equivalent dose-effect curve $Y(Am+Bn)=g(Bn+Bm)$ of the expected additive effect value $Y(Am+Bn)$ of the combined drug with a dose change of the first component drug A; a fourth finding unit, configured to find or calculate an effect value $g(Bn)$ of the second component drug B under a combined dose $Bn$ on the second dose-effect relationship curve $Y=g(x)$; a fifth finding unit, configured to find or calculate an equivalent dose value $An$ same as the effect value $g(Bn)$ and corresponding to an effect value $f(An)$ of the first component drug A on the first dose-effect relationship curve $Y=f(x)$; a second calculation unit, configured to calculate a dose sum $(Am+An)$ of a combined dose $Am$ and the equivalent dose $An$ of the first component drug A; a sixth finding unit, configured to find or calculate a corresponding effect value $f(Am+An)$ when the dose of the first component drug A on the first dose-effect relationship curve $Y=f(x)$ is the dose sum $(Am+An)$; a second conversion unit, configured to convert the effect value $f(Am+An)$ into the expected additive effect value $Y(Am+Bn)$ of the combined drug; and a second curve establishment unit, configured to establish a second equivalent dose-effect curve $Y(Am+Bn)=f(Am+An)$ of the expected additive effect value of the combined drug with the dose change of the first component drug A.

Further, the processing apparatus further includes: a first calculation module, configured to calculate a corresponding first dose range of the one target component drug when the actual dose-effect relationship curve is located above the dose-effect curve band after the first output module outputs the efficacy of the combined drug as the synergistic effect; and a fourth output module, configured to output the first dose range as a synergistic dose range of the one target component drug.

Further, the processing apparatus further includes: a third obtaining module, configured to obtain a combined relationship between the one target component drug and rest component drugs in the combined drug after the fourth output module outputs the first dose range as the synergistic dose range of the one target component drug; a second calculation module, configured to calculate synergistic dose ranges of the rest component drugs in the combined drug under a combined condition according to the combined relationship; and a fifth output module, configured to output the synergistic dose ranges of the rest component drugs.

Further, the processing apparatus further includes: a third calculation module, configured to calculate a corresponding second dose range of the one target component drug when the actual dose-effect relationship curve is located below the dose-effect curve band after the second output module outputs the efficacy of the combined drug as the antagonistic effect; and a sixth module, configured to output the second dose range as an antagonistic dose range of the one target component drug.

Further, the processing apparatus further includes: a fourth obtaining module, configured to obtain a combined relationship between the one target component drug and rest component drugs in the combined drug after the sixth output module outputs the second dose range as the antagonistic dose range of the one target component drug; a fourth calculation module, configured to calculate antagonistic dose ranges of the rest component drugs in the combined drug under a combined condition according to the combined relationship; and a seventh output module, configured to output the antagonistic dose ranges of the rest component drugs.

Further, the processing apparatus further includes: a fifth calculation module, configured to calculate a corresponding third dose range of the one target component drug when the actual dose-effect relationship curve is located within the range of the dose-effect curve band after the third output module outputs the efficacy of the combined drug as the additive effect; and an eighth module, configured to output the third dose range as an additive dose range of the one target component drug.

Further, the processing apparatus further includes: a fifth obtaining module, configured to obtain a combined relationship between the one target component drug and rest component drugs in the combined drug after the eighth output module outputs the third dose range as the additive dose range of the one target component drug; a sixth calculation module, configured to calculate additive dose ranges of the rest component drugs in the combined drug under a combined condition according to the combined relationship; and a ninth output module, configured to output the additive dose ranges of the rest component drugs.

Further, the first comparison module includes: a first obtaining sub-module, configured to obtain a minimum value and a maximum value of an expected additive effect of a corresponding combined drug in a range of the dose-effect curve band under a specific combined dose of the one target component drug; a second obtaining sub-module, configured to obtain an actual effect value of the corresponding combined drug on the actual dose-effect relationship curve under the specific combined dose of the one target component drug; a first calculation sub-module, configured to calculate a first ratio of the actual effect value to the minimum value of the expected additive effect; a second calculation sub-module, configured to calculate a second ratio of the actual effect value to the maximum value of the expected additive effect; a first labeling sub-module, configured to respectively label the first ratio and the second ratio as $CI_{d1}$ and $CI_{d2}$; a first determining sub-module, configured to determine that the actual dose-effect relationship curve is located above the dose-effect curve band when the $CI_{d1}$ and the $CI_{d2}$ both are greater than 1; a second determining sub-module, configured to determine that the actual dose-effect relationship curve is located below the dose-effect curve band when the $CI_{d1}$ and the $CI_{d2}$ both are smaller than 1; and a third determining module, configured to determine that the actual dose-effect relationship curve is located within the range of the dose-effect curve band if either the $CI_{d1}$ or the $CI_{d2}$ is greater than or equal to 1 or is smaller than or equal to 1.

Further, the processing apparatus further includes an eleventh output module, configured to output the $CI_{d1}$ and the $CI_{d2}$ after the first labeling sub-module respectively labels the first ratio and the second ratio as the $CI_{d1}$ and the $CI_{d2}$.

Further, the first comparison module includes: a third obtaining sub-module, configured to obtain a minimum value and a maximum value of corresponding doses of the one target component drug when the combined drug generates a specific effect on the dose-effect curve band; a fourth obtaining sub-module, configured to obtain an actual combined dose required when the combined drug generates the specific effect on the actual dose-effect relationship curve; a third calculation sub-module, configured to calculate a third ratio of the actual combined dose to the minimum value; a fourth calculation sub-module, configured to calculate a fourth ratio of the actual combined dose to the maximum value; a second labeling sub-module, configured to respectively label the third ratio and the fourth ratio as $CI_{e1}$ and $CI_{e2}$; a fourth determining sub-module, configured to determine that the actual dose-effect relationship curve is located above the dose-effect curve band when the $CI_{e1}$ and the $CI_{e2}$ both are smaller than 1; a fifth determining sub-module, configured to determine that the actual dose-effect relationship curve is located below the dose-effect curve band when the $CI_{e1}$ and the $CI_{e2}$ both are greater than 1; and a sixth determining sub-module, configured to determine that the actual dose-effect relationship curve is located within the range of the dose-effect curve band when either the $CI_{e1}$ or the $CI_{e2}$ is greater than or equal to 1 or is smaller than or equal to 1.

Further, the processing apparatus further includes a twelfth output module, configured to output the $CI_{d1}$ and the $CI_{d2}$ after the second labeling sub-module respectively labels the third ratio and the fourth ratio as the $CI_{e1}$ and the $CI_{e2}$.

To this end, according to one aspect of the present disclosure, there is provided a storage medium. The storage medium is configured to store a program code executed by any of the processing methods for the efficacy of the combined drug.

According to yet another aspect of the present disclosure, there is provided a computer terminal. The computer terminal includes: one or more processors, a memory and a transmission apparatus, wherein the memory is configured to store a program instruction and/or module corresponding to the processing method and/or apparatus for the efficacy of the combined drug; through operating the program instruction and/or module stored in the memory, the processor executes various functional applications and data processing to implement the processing method for the efficacy of the combined drug.

Through applying the technical solutions of the present disclosure, by comparing with the actual dose-effect curve of the combined drug based on the dose-effect curve band of the expected additive effect of the combined drug, and then judging the efficacy of the combined drug via the positional relationship between the actual dose-effect curve and the dose-effect curve band, since the dose-effect curve band is more suitable for the dose-effect relationship of the drug and pharmacodynamic basic characteristics when the drug is in the combined use, the efficacy processing method of the embodiments integrates different drug sequences when multiple drugs are in the combined use and influences of different dose-effect relationships of different drugs on the efficacy of the combined drug. It not only can implement detection on the efficacy when multiple (two or more) drugs are in the combined use, but also can implement quantitative detection. The processing method solves the problem that the efficacy cannot be accurately detected when multiple drugs are in the combined use in the conventional art. Moreover, the efficacy, obtained by the detection, of the combined drug can be widely applied to research and development of a compound drug, toxicological study and environmental evaluation. In addition, dose ranges that the multiple drugs generate the synergistic, additive and antagonistic effects under different combined conditions and related indexes combined with other drugs further can be quantitatively calculated as needed.

BRIEF DESCRIPTION OF THE DRAWINGS

The accompanying drawings described herein are intended to provide further understanding of the embodiments of the present disclosure and constitute a part of present disclosure. The exemplary embodiments of the present disclosure and descriptions thereof are intended to explain the present disclosure, and not to constitute an improper limitation to the present disclosure. In the accompanying drawings:

FIG. 1 illustrates a flowchart of a processing method for efficacy of a combined drug in a preferred embodiment.

FIG. 3D illustrates a dose-effect relationship curve of the actual efficacy in the combined group with the dose change of the drug NX therein when the NX at different doses and +TX at a fixed proportion are combined.

FIG. 8D illustrates a dose-effect relationship curve of the etoposide (A) in the drug combined group.

DETAILED DESCRIPTION OF THE EMBODIMENTS

Figure 2:
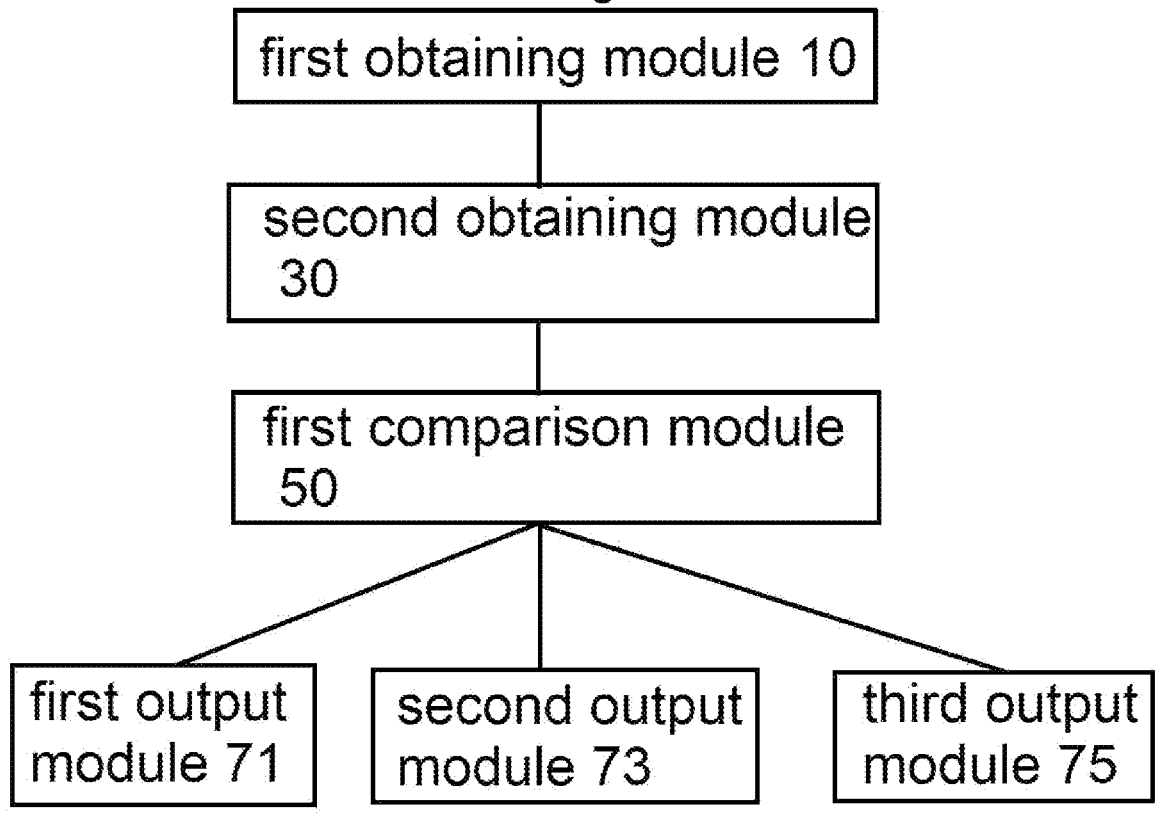
FIG. 2 is a structural systematic diagram of a processing apparatus for efficacy of a combined drug in a preferred embodiment.

It should be noted that the embodiments of the present disclosure and characteristics in the embodiments can be mutually combined if there is no conflict. The present disclosure will be described below in detail with reference to embodiments.

To make a person skilled in the art to better understand the solutions of the present disclosure, the technical solutions in the embodiments of the present disclosure are described clearly and completely in the following with reference to the accompanying drawings in the embodiments of the present disclosure. Obviously, the embodiments to be described are only a part rather than all of the embodiments of the present disclosure. Based on the embodiments of the present disclosure, all other embodiments obtained by persons of ordinary skill in the art without making any creative effort shall fall within the protection scope of the present disclosure.

It should be noted that in the specification, claims, and accompanying drawings of the embodiments of present disclosure, the terms "first", "second", and so on are intended to distinguish between similar objects but do not necessarily indicate a specific order or sequence. It should be understood that data used in this way is exchangeable in a proper case, so that the embodiments of the present disclosure described herein can be implemented in another order except those shown or described herein. Moreover, the terms "include", "contain" and any other variants mean to cover the non-exclusive inclusion, for example, a process, method, system, product, or device that includes a list of steps or units is not necessarily limited to those units, but may include other units not expressly listed or inherent to such a process, method, system, product, or device.

It should be noted that, steps shown in the flowcharts of the accompanying drawings may be performed in, for example, a computer system having a set of computer executable instructions. Moreover, although logical sequences are shown in the flowcharts, in some cases, the steps that are shown or described may be performed in a sequence different from those shown herein.

The method provided by the embodiments of the present disclosure may be implemented in a mobile terminal, a computer terminal or a similar computing device.

Optionally, in the embodiments, the efficacy detection method when multiple drugs are combined may be applied to a network environment. In the embodiment, the efficacy detection method when multiple drugs are combined may be applied to a hardware network environment composed of a terminal and a server. The terminal is connected with the server via a network. The network includes but is not limited to a wide area network, a metropolitan area network, or a local area network. In the embodiments of the present disclosure, the terminal may a mobile terminal and a personal computer. Specifically, the terminal may be a terminal such as an Intelligent mobile phone, a tablet computer and a Personal Digital Assistant (PDA).

Under the above operating environments, the present disclosure provides a processing method for efficacy of a combined drug as shown in FIG. 1. FIG. 1 is a flowchart of a processing method for efficacy of a combined drug according to an embodiment of the present disclosure.

As shown in FIG. 1, the processing method includes the following steps.

In Step S202: a dose-effect curve band of an expected additive effect of the combined drug is obtained, wherein the dose-effect curve band is enclosed by two equivalent dose-effect curves at the most periphery in multiple equivalent dose-effect curves, each of the equivalent dose-effect curves is a curve established by taking a dose of one target component drug in the combined drug as a horizontal coordinate and an expected additive effect obtained by equivalently converting the combined drug into any component drug as a vertical coordinate, and the equivalent conversion is performed according to a drug sequence of each component drug in the obtained combined drug.

In Step S204: an actual dose-effect relationship curve formed by an actual effect value of the combined drug with a dose change of the one target component drug in the combined drug is obtained.

In Step S206: a positional relationship between the actual dose-effect relationship curve and the dose-effect curve band is compared.

In Step S208: the efficacy of the combined drug is output as a synergistic effect when the actual dose-effect relationship curve is located above the dose-effect curve band; the efficacy of the combined drug is output as an antagonistic effect when the actual dose-effect relationship curve is located below the dose-effect curve band; and the efficacy of the combined drug is output as an additive effect when the actual dose-effect relationship curve is located within a range of the dose-effect curve band.

Herein, the drug sequence of each component drug in the obtained combined drug Includes a combined dose or concentration of each component drug, and a dose-effect relationship curve of each component drug.

Through the processing method of the present disclosure, by comparing with the actual dose-effect curve of the combined drug based on the dose-effect curve band of the expected additive effect of the combined drug, and then judging the efficacy of the combined drug via the positional relationship between the actual dose-effect curve and the dose-effect curve band, since the dose-effect curve band is more suitable for the dose-effect relationship of the drug and pharmacodynamic basic characteristics when the drug is in the combined use, the efficacy processing method of the embodiments integrates different drug sequences when multiple drugs are in the combined use and influences of different dose-effect relationships of different drugs on the efficacy of the combined drug. It not only can implement detection on the efficacy when multiple (two or more) drugs are in the combined use, but also can implement quantitative detection. The processing method solves the problem that the efficacy cannot be accurately detected when multiple drugs are in the combined use in the conventional art. Moreover, the efficacy, obtained by the detection, of the combined drug can be widely applied to research and development of a compound drug, toxicological study and environmental evaluation. In addition, dose ranges that the multiple drugs generate the synergistic, additive and antagonistic effects under different combined conditions and related indexes combined with other drugs further can be quantitatively calculated as needed (for example, combination indexes $CI_d$ and $CI_e$).

Specifically, after the dose-effect relationship curve of each component drug in the combined drug is obtained, the expected additive effect of the combined drug is equivalently converted into the expected additive effect of each component drug according to an equivalent conversion principle; then, the equivalent dose-effect curve of the expected additive effect of each combined drug with the dose change of the one target component drug is established; and then, the curve band enclosed by two equivalent dose-effect curves at the most periphery in multiple equivalent dose-effect curves is obtained, and thus, the dose-effect curve band of the expected additive effect of the combined drug is obtained. And meanwhile, after the dose-effect curve band is obtained, the actual dose-effect relationship curve of the actual effect value of the combined drug with the dose change of the one target component drug in the combined drug is obtained; and then, the positional relationship between the dose-effect curve band and the actual dose-effect curve is compared, and according to that the actual dose-effect curve is located above, below or in the range of the dose-effect curve band, the efficacy of the combined drug is correspondingly output as the synergistic, antagonistic or additive effects.

In the embodiment, according to drug types in the combined drug and different combined sequences of the component drugs, by respectively and equivalently converting the expected additive effect of the combined drug into the equivalent dose-effect curve of each component drug, the obtained dose-effect curve of the expected additive effect of the combined drug is the same as the dose-effect curve of each component drug in itself. Since the additive effect is a zero interaction, and when the multiple drugs are simultaneously exposed to each efficacy execution unit in a body tissue, a sequential order that the drugs take the effect is random, the expected additive effect of the combined drug is a sum of effects of all efficacy execution units. An efficacy exertion sequence of one efficacy execution unit is an effect that upon an effect exerted by a first component drug A, a B exerts an own dose again along a dose-effect curve of the B, and that of the other efficacy execution unit may be an effect that upon the effect exerted by the second component B, the A exerts an own dose again along a dose-effect curve of the A. It can be expressed by a formula:

$$Y_{(Am+Bn)} = [Y_{(Am+Bn)}, Y'_{(Am+Bn)}]_{Hi}^{Lo}\downarrow = [(g(Bn)+f(Am))|_{g(Bn)}, (f(Am)+g(Bn)|_{f(Am)})]_{Hi}^{Lo}\downarrow = [(f(A_n)+f(Am))|_{f(An)}, (g(Bm)+g(Bn)|_{g(Bm)})]_{Hi}^{Lo}\downarrow = [f(Am+An), g(Bm+Bn)]_{Hi}^{Lo}\downarrow$$

Where, Lo=Low, Hi=High, $_{Hi}^{Lo}\downarrow$ indicates a function value of a unit in a number set and is arranged from low to high, Bn and An are equivalent doses, and Am and Bm are the equivalent doses.

Therefore, when two drugs are combined at a certain determined dose (Am and Bn), the expected additive effect is a range, namely the number set; two expected additive effect values are boundary values of the number set, and respectively represent all efficacy execution units are hundred-percent Am→Bn and hundred-percent Bn→Am, and the middle numerical range is a an accumulative sum for the efficacy of Am→Bn and Bn→Am efficacy execution units at different proportions. The expected additive effect value in the range of the number set is more suitable for the dose-effect curve band relationship, rather than a straight line in the conventional art.

Optionally, the combined drug includes a first component drug A and a second component drug B. Before the step of obtaining the dose-effect curve band of the expected additive effect of the combined drug, the processing method further includes a step of establishing multiple equivalent dose-effect curves, wherein the step of establishing the multiple equivalent dose-effect curves includes: obtaining a first dose-effect relationship curve Y=f(x) of the first component drug A; obtaining a second dose-effect relationship curve $Y=g(x)$ of the second component drug B; finding or calculating an effect value $f(Am)$ of the first component drug A under a combined dose Am on the first dose-effect relationship curve $Y=f(x)$; finding or calculating an equivalent dose value Bm same as the effect value $f(Am)$ and corresponding to an effect value $g(Bm)$ of the second component drug B on the second dose-effect relationship curve $Y=g(x)$; calculating a dose sum (Bn+Bm) of a combined dose Bn and the equivalent dose Bm of the second component drug B; finding or calculating a corresponding effect value $g(Bn+Bm)$ when the dose of the second component drug B on the second dose-effect relationship curve $Y=g(x)$ is the dose sum (Bn+Bm); converting the effect value $g(Bn+Bm)$ into an expected additive effect value $Y(Am+Bn)$ of the combined drug; establishing a first equivalent dose-effect curve $Y(Am+Bn)=g(Bn+Bm)$ of the expected additive effect value $Y(Am+Bn)$ of the combined drug with a dose change of the first component drug A; finding or calculating an effect value $g(Bn)$ of the second component drug B under a combined dose Bn on the second dose-effect relationship curve $Y=g(x)$; finding or calculating an equivalent dose value An same as the effect value $g(Bn)$ and corresponding to an effect value $f(An)$ of the first component drug A on the first dose-effect relationship curve $Y=f(x)$; calculating a dose sum (Am+An) of a combined dose Am and the equivalent dose An of the first component drug A; finding or calculating a corresponding effect value $f(Am+An)$ when the dose of the first component drug A on the first dose-effect relationship curve $Y=f(x)$ is the dose sum (Am+An); converting the effect value $f(Am+An)$ into the expected additive effect value $Y(Am+Bn)$ of the combined drug; establishing a second equivalent dose-effect curve $Y(Am+Bn)=f(Am+An)$ of the expected additive effect value of the combined drug with the dose change of the first component drug A.

The process of establishing the equivalent dose-effect curve is to equivalently convert an effect generated by the first component drug A under the combined dose into the second component drug B, that is to equivalently convert the expected additive effect of the combined drug into a dose of the second component drug B and a corresponding effect value. Similarly, when the effect generated by the second component drug B under the combined dose is equivalently converted into the first component drug A, the above step is repeated, and the established equivalent dose-effect curve is to equivalently convert the effect generated by the second component drug B under the combined dose into the first component drug A and equivalently convert the expected additive effect of the combined drug into the dose of the first component drug A and the corresponding effect value. Since the drug sequence of the two drugs in the combined use is to use the A first and then the B, or use the B first and then the A, there are two equivalent dose-effect curves of the expected additive effect of the combined drug. Therefore, the dose-effect curve band enclosed by the two equivalent dose-effect curves is the dose-effect curve band of the expected additive effect when two drugs are in the combined use.

Same as the steps of establishing the equivalent dose-effect curve of the expected additive effect when the two drugs are in the combined use, the expected additive effect for the combined use of three drugs is an efficacy level that a third drug reaches to an own dose along an own dose-effect curve based on additive effects of any two drugs. That is, a function value obtained after equivalent dose conversion is performed on the expected additive effect of the combined drug and the dose-effect curve of the third drug and by merging the equivalent dose with the dose of the third drug and following a dose-effect relationship function of the third drug is the expected additive effect value when the three drugs are in the combined use. The reverse is also true. On the basis of the effect of one drug, the other any two drugs reach to the efficacy levels of the own doses along dose-effect curves of own additive effects. The additive effect of any two drugs therein is the expected additive effect band obtained when the combined drug contains the first component drug A and the second component drug B. In other words, the expected additive when the three drugs are in the combined use is that the third drug reaches to the efficacy level of the own dose along the own dose-effect curve based on the equivalent dose-effect curve that any two drugs are converted into one of the component drugs according to the combined dose, and vice versa.

The drug a, the drug b and the drug c have three different drug sequence combinations, including (a+b)+c, (a+c)+b and (b+c)+a. In each drug sequence combination, according the equivalent conversion principle of the first component drug A and the second component drug B, the first component drug Is updated as a medicine (a+b), (a+c) and (b+c), and the expected additive effect of the sequence combination of (a+b)+c may be an equivalent dose-effect curve by equivalently converting the (a+b) into the c, and also may be an equivalent dose-effect curve by equivalently converting into the (a+b). The equivalent dose-effect curve of the (a+b) also may be an equivalent dose-effect curve by equivalently converting into the a and also may be an equivalent dose-effect curve by equivalently converting into the b. Therefore, the expected additive effect of the combined drug of the (a+b)+c has four equivalent dose-effect curves. According to different drug combinations, the process of establishing the equivalent dose-effect curve is repeated to obtain 12 equivalent dose-effect curves, wherein the curve band enclosed by two equivalent dose-effect curves at the most periphery is the dose-effect curve band of the expected additive effect when the three drugs are in the combined use.

Same as the steps of establishing the equivalent dose-effect curve of the expected additive effect when the two drugs are in the combined use and the three drugs are in the combined use, the calculation of an expected additive effect when four drugs are in the combined use is a sum of the above two conditions. 1) On the basis of additive effects of any three drugs, a fourth component drug reaches to an efficacy level of an own dose along an own dose-effect curve. That is, a function value obtained after equivalent dose conversion is performed on the expected additive effect of the combined drug and the dose-effect curve of the fourth drug and by merging the equivalent dose with the dose of the fourth drug and following a dose-effect relationship function of the fourth drug is the expected additive effect value when the four drugs are in the combined use. The reverse is also true. On the basis of the effect of one drug, the other any additive three drugs reach to the efficacy levels of the own doses along dose-effect curves of own additive effects. 2) On the basis of additive effects of any two drugs, the other one group of two-drug combinations reaches to an own efficacy level along an own dose-effect curve band and the equivalent conversion principle is the same.

When five, six . . . n drugs are in the combined use, the steps of establishing the equivalent dose-effect curve are executed repeatedly only according to different types of the combined drugs, the number of formed drug combinations and different drug combination sequences, and an iterative loop is performed stepwise to establish all equivalent dose-effect curves. And then, the curve bands enclosed by the curves at the most periphery in the all equivalent dose-effect curves are obtained to obtain the dose-effect curve band of the expected additive effect when multiple drugs are in the combined use.

From the foregoing, regardless of whether the combined drug is of two drugs, three drugs, four drugs and n drugs, the steps of establishing the equivalent dose-effect curve include steps of equivalently converting two drugs and establishing the equivalent dose-effect curve. Hence, in the embodiments, the steps of establishing the equivalent dose-effect curve include steps common for all ≥2 combined drugs in establishment of the equivalent dose-effect curve. As a result, when the dose-effect curve band of the expected additive effect of n (n≥2) combined drugs is obtained, any using the steps of establishing the dose-effect curve shall be within the scope of the present disclosure.

Optionally, when the efficacy output result of the combined drug is the synergistic effect, after the step of outputting the efficacy of the combined drug as the synergistic effect, the processing method further includes: calculating a corresponding first dose range of the one target component drug when the actual dose-effect relationship curve is located above the dose-effect curve band; and outputting the first dose range as a synergistic dose range of the one target component drug.

Specifically, according to a function relationship between the actual dose-effect relationship curve and the dose-effect curve band, a dose of the one target component drug at an intersection of the actual dose-effect relationship curve and the dose-effect curve band can be calculated; and according to the dose, the corresponding first dose range located above the intersection and belonging to the synergistic effect can be calculated.

Optionally, after outputting the synergistic dose range of the one target component drug, the processing method further includes: obtaining a combined relationship between the one target component drug and rest component drugs in the combined drug; calculating synergistic dose ranges of the rest component drugs in the combined drug under a combined condition according to the combined relationship; and outputting the synergistic dose ranges of the rest component drugs.

Specifically, the combined relationship between the one target component drug and the rest component drugs in the combined drug may be obtained according to the combined relationship, obtained in advance, of each component drug in the combined drug. For example, when the combined drug includes A, B and C, the three drugs are combined according to the fixed proportion of A:B:C=2:2:5 (μg/ml+ μg/ml+μg/ml). When the A is the target component drug, according to the dose at the intersection of the expected additive effect curve band and the actual dose-effect relationship curve of the three drugs in the combined use, the synergistic dose range of the A component drug can be calculated when the efficacy of the combined drug is the synergistic effect. According to a mixture relationship that the A component drug and the B component drug are 1:1, the synergistic dose range of the B component drug can be obtained. Likewise, according to a mixture relationship that the A component drug and the B component drug is 2:5, the synergistic dose range of the C component drug also can be obtained.

Similarly, when the combined drug is combined in terms of other combined conditions, the synergistic dose ranges of the rest component drugs also may be obtained according to different specific combined conditions. For example, when the A and the B are combined, the A at the fixed 1 ng/ml concentration and the B at different concentrations (μg/ml) are combined and the synergistic dose range of the target drug B is obtained, the synergistic dose range of the A component drug is a fixed dose in the combined use.

On the basis of obtaining the synergistic dose range of each component, by adding the synergistic dose range of each component, the synergistic dose range when the efficacy of the combined drug is the synergistic effect can be obtained. In actual applications, according to requirements of research and development of the compound drug, toxicological study and environmental evaluation, the synergistic dose range of the target drug and related dose combination index and/or effect combination index also can be obtained.

Optionally, when the efficacy output result of the combined drug is the antagonistic effect, after the step of outputting the efficacy of the combined drug as the antagonistic effect, the processing method further includes: calculating a corresponding second dose range of the one target component drug when the actual dose-effect relationship curve is located below the dose-effect curve band; and outputting the second dose range as an antagonistic dose range of the one target component drug.

Specifically, the method for calculating the corresponding second dose range of the one target component drug when the actual dose-effect relationship curve is located below the dose-effect curve band also can obtain a range of doses when the effect is located below the dose effect according to corresponding doses when the actual dose-effect relationship curve is located at the intersection with the dose-effect curve band, namely an antagonistic dose range of the one target component drug. In actual applications, according to requirements of research and development of the compound drug, toxicological study and environmental evaluation, an antagonistic dose range of the target drug further can be obtained.

Optionally, after outputting the antagonistic dose range of the one target component drug, the processing method further includes: obtaining a combined relationship between the one target component drug and rest component drugs in the combined drug; calculating antagonistic dose ranges of the rest component drugs in the combined drug under a combined condition according to the combined relationship; and outputting the antagonistic dose ranges of the rest component drugs.

The antagonistic dose ranges of the rest component drugs are calculated same as the synergistic dose ranges; and the antagonistic dose ranges of the rest component drugs are obtained according to the calculation method same as the synergistic dose ranges after an antagonistic dose range of the one target component drug according to the combined relationship among each component drug in the combined drug is obtained.

Optionally, when the efficacy output result of the combined drug is the additive effect, after the step of outputting the efficacy of the combined drug as the additive effect, the processing method further includes: calculating a corresponding third dose range of the one target component drug when the actual dose-effect relationship curve is located within the range of the dose-effect curve band; and outputting the third dose range as an additive dose range of the one target component drug.

The additive dose range of the one target component drug is calculated same as the synergistic dose range. The intersections of the actual dose-effect curve and the dose-effect curve band are a minimum dose and a maximum dose of the one target component drug when the combined drug is in the additive effect, and the doses between the two doses are a dose range of the additive effect.

Optionally, after outputting the additive dose range of the one target component drug, the processing method further includes: obtaining a combined relationship between the one target component drug and rest component drugs in the combined drug; calculating additive dose ranges of the rest component drugs in the combined drug under a combined condition according to the combined relationship; and outputting the additive dose ranges of the rest component drugs.

The additive dose ranges of the rest component drugs are calculated same as the synergistic dose ranges; and the additive dose ranges of the rest component drugs are obtained according to the calculation method same as the synergistic dose ranges after an additive dose range of the one target component drug according to the combined relationship among each component drug in the combined drug is obtained.

Optionally, when the combined drug includes the first component drug A and the second component drug B, the calculation of the additive dose range of the one target component drug further may be implemented by the following steps besides the calculation according to the doses at the intersections of the actual dose-effect relationship curve and the dose-effect curve band.

A first merged dose actual effect curve Y'(Am+Bn)=g(Bn+Bm) and a first merged dose expected additive effect curve Y''(Am+Bn)=p(Bn+Bm) are established by taking the above doses and change values of (Bn+Bm) as horizontal coordinates and respectively taking the actual effect value and the expected additive effect value of the combined drug as vertical coordinates.

An effect value Y(Am+Bn)$_1$ corresponding to the intersection of the first merged dose actual effect curve Y'(Am+Bn)=g(Bn+Bm) and the first merged dose expected additive effect curve Y''(Am+Bn)=p(Bn+Bm) is calculated.

An actual dose-effect relationship curve Y(Am+Bn)=h(m) of the actual effect value of the combined drug with the dose change of the first component drug A is obtained.

A combined dose Am$_1$ of the first component drug A corresponding to the effect value Y(Am+Bn)$_1$ on the actual dose-effect relationship curve Y(Am+Bn)=h(m) is calculated.

A second merged dose actual effect curve Y'(Am+Bn)=f(Am+An) and a second merged dose expected additive effect curve Y''(Am+Bn)=q(Bn+Bm) are established by taking the above doses and change values of (An+Am) as horizontal coordinates and respectively taking the actual effect value and the expected additive effect value of the combined drug as vertical coordinates.

An effect value Y(Am+Bn)$_2$ corresponding to the intersection of the second merged dose actual effect curve Y'(Am+Bn)=f(Am+An) and the second merged dose expected additive effect curve Y''(Am+Bn)=q(Bn+Bm) is calculated.

A combined dose Am$_2$ of the first component drug A corresponding to the effect value Y(Am+Bn))$_2$ on the actual dose-effect relationship curve Y(Am+Bn)=h(m) is calculated.

Doses between the combined dose Am$_1$ and the combined dose Am$_2$ are taken as a dose range of the first component drug A when the efficacy of the combined drug is the additive effect.

According to the combined relationship between the first component drug A and the second component drug B, a dose range of the second component drug B when the efficacy of the combined drug is the additive effect is calculated.

The method for calculating the dose range of each component in the additive effect is also applied to the combined use of three or more component drugs. When the types of the combined drug are ≥2, a set of multiple additive effect dose values similar to the combined doses Am$_1$ and Am$_2$ may be obtained according to the above steps, and a minimum value and a maximum value in the set are selected as a dose range of the additive effect of the combined drug (≥2). Similarly, the additive effect dose ranges of the rest components can be calculated according to the combined conditions. The method is more convenient when the additive effect dose range is calculated.

Optionally, the step of comparing the positional relationship between the actual dose-effect relationship curve and the dose-effect curve band includes: obtaining a minimum value and a maximum value of an expected additive effect of a corresponding combined drug in a range of the dose-effect curve band under a specific combined dose of the one target component drug; obtaining an actual effect value of the corresponding combined drug on the actual dose-effect relationship curve under the specific combined dose of the one target component drug; calculating a first ratio of the actual effect value to the minimum value of the expected additive effect; calculating a second ratio of the actual effect value to the maximum value of the expected additive effect; respectively labeling the first ratio and the second ratio as $CI_{d1}$ and $CI_{d2}$; if the $CI_{d1}$ and the $CI_{d2}$ both are greater than 1, determining that the actual dose-effect relationship curve is located above the dose-effect curve band; if the $CI_{d1}$ and the $CI_{d2}$ both are smaller than 1, determining that the actual dose-effect relationship curve is located below the dose-effect curve band; and if either the $CI_{d1}$ or the $CI_{d2}$ is greater than or equal to 1 or is smaller than or equal to 1, determining that the actual dose-effect relationship curve is located within the range of the dose-effect curve band.

The embodiment is convenient to judge the positional relationship between the actual dose-effect relationship curve and the dose-effect curve band on different effect value levels under any given dose. When the same dose is given, corresponding effect values on the actual dose-effect relationship curve are respectively compared with minimum values and maximum values of corresponding expected additive effects on the dose-effect curve band, thereby obtaining combination indexes $CI_{d1}$ and $CI_{d2}$ based on the dose. According to the $CI_{d1}$ and the $CI_{d2}$ simultaneously being greater than 1, it can be judged that the actual dose-effect relationship curve is located above the dose-effect curve band. According to the $CI_{d1}$ and the $CI_{d2}$ simultaneously being smaller than 1, it can be judged that the actual dose-effect relationship curve is located below the dose-effect curve band. According to either the $CI_{d1}$ or the $CI_{d2}$ being greater than or equal to 1 or either the $CI_{d2}$ being smaller than or equal to 1, it is indicated that one actual effect value is within the dose-effect curve band of the expected additive effect and the effect is the additive effect.

Optionally, after the step of respectively labeling the first ratio and the second ratio as the $CI_{d1}$ and the $CI_{d2}$, the processing method further includes a step of outputting the $CI_{d1}$ and the $CI_{d2}$. The step is beneficial to obtain a dose combination index according to an actual drug combined condition in applications of research and development, toxicological study and environmental evaluation of an actual compound drug.

Optionally, the step of comparing the positional relationship between the actual dose-effect relationship curve and the dose-effect curve band includes: obtaining a minimum value and a maximum value of corresponding doses of the one target component drug when the combined drug generates a specific effect on the dose-effect curve band; obtaining an actual combined dose required when the combined drug generates the specific effect on the actual dose-effect relationship curve; calculating a third ratio of the actual combined dose to the minimum value; calculating a fourth ratio of the actual combined dose to the maximum value; respectively labeling the third ratio and the fourth ratio as $CI_{e1}$ and $CI_{e2}$; if the $CI_{e1}$ and the $CI_{e2}$ both are smaller than 1, determining that the actual dose-effect relationship curve is located above the dose-effect curve band; if the $CI_{e1}$ and the $CI_{e2}$ both are greater than 1, determining that the actual dose-effect relationship curve is located below the dose-effect curve band; and if either the $CI_{e1}$ or the $CI_{e2}$ is greater than or equal to 1 or is smaller than or equal to 1, determining that the actual dose-effect relationship curve is located within the range of the dose-effect curve band.

The embodiment is convenient to compare the positional relationship between the actual dose-effect curve and the dose-effect curve band in different dose ranges under any given efficacy level. When it is at a specific efficacy value such as $ED_{50}$, the vertical coordinate on the dose-effect relationship curve band of the combined drug is a straight line drawn parallel to the horizontal coordinate at 50, and is respectively intersected with the dose-effect curve band and the actual dose-effect curve at A, B and C, and thus horizontal coordinate values at A, B and C are obtained and are assumed to be 1.012, 1.321 and 1.450. At the efficacy $ED_{50}$, a minimum value of a dose of an expected additive effect of the one target component drug is 1.012, a maximum value is 1.321 and the dose of the actual effect is 1.450. Since $CI_{e1}=1.450/1.012>1$, $CI_{e2}=1.450/1.321>1$, it is indicated that when same efficacy is generated, the dose of the one target component drug actually needed to be given is greater than the expected dose. Therefore, under the effect value, the actual dose-effect relationship curve is located below the dose-effect curve band. If the $CI_{e1}$ and the $CI_{e2}$ are smaller than 1, it is determined that the actual dose-effect relationship curve is located above the dose-effect curve band and the efficacy is antagonistic. If the $CI_{e1}$ and the $CI_{e2}$ are greater than 1, it is determined that the actual dose-effect relationship curve is located below the dose-effect curve band. If the $CI_{e1}$ or the $CI_{e2}$ is greater than or equal to 1, it Is determined that the actual dose-effect relationship curve is located within the range of the dose-effect curve band.

The positional relationship comparison method in the embodiment is based on the dose-effect curve band, and is based on two effect values or two dose values of the expected additive effect on the dose-effect curve band under a same dose condition or a given efficacy level, so the efficacy of the combined drug can be detected quantitatively and more accurately according to the combination indexes of the combined drug. For example, when the $CI_{e1}<1$ and the $CI_{e2}<1$, it is determined that the actual dose-effect relationship curve is located below the dose-effect curve band and the efficacy of the combined drug is the synergistic effect. The further the specific value of the $CI_{e1}$ and the $CI_{e2}$ to 1 is, the stronger the synergistic effect of the combined drug is. The closer the specific value of the $CI_{e1}$ and the $CI_{e2}$ to 1 is, the weaker the synergistic effect of the combined drug is. Therefore, the efficacy level of the combined drug can be detected quantitatively.

Optionally, after the step of respectively labeling the third ratio and the fourth ratio as the $CI_{e1}$ and the $CI_{e2}$, the processing method further includes a step of outputting the $CI_{e1}$ and the $CI_{e2}$. According to requirements of research and development, toxicological study and environmental evaluation of a compound drug in actual applications, the effect combination index can be obtained.

It should be noted that, for simple description, the foregoing method embodiments are represented as a combination of a series of actions, but a person skilled in the art should appreciate that the embodiments of the present disclosure are not limited to the described order of the actions because some steps may be performed in another order or performed simultaneously according to the embodiments of the present disclosure. In addition, a person skilled in the art should also appreciate that all the embodiments described in this specification are preferred embodiments, and the related actions and modules are not necessarily mandatory to the embodiments of the present disclosure.

Through the foregoing descriptions of the implementations, it is clear to a person skilled in the art that the method according to the foregoing embodiments may be implemented by software plus a necessary universal hardware platform, and certainly may also be implemented by hardware, but in many cases, the software implementation is preferred. Based on such understanding, the technical solutions of the embodiments of the present disclosure or the part that makes contributions to the existing technology may be substantially embodied in the form of a software product. The computer software product is stored in a storage medium (for example, a ROM/RAM, a magnetic disk, or an optical disc), and contains several instructions for instructing a terminal device (which may be a mobile phone, a computer, a first terminal, or a network device) to perform the method according to the embodiments of the present disclosure.

According to an embodiment of the present disclosure, there is further provided a processing apparatus for efficacy of a combined drug. As shown in FIG. 2, the processing apparatus includes: a first obtaining module 10, a second obtaining module 30, a first comparison module 50, a first output module 71, a second output module 73 and a third output module 75.

Herein, the first obtaining module 10 is configured to obtain a dose-effect curve band of an expected additive effect of the combined drug, wherein the dose-effect curve band is enclosed by two equivalent dose-effect curves at the most periphery in multiple equivalent dose-effect curves, each of the equivalent dose-effect curves is a curve established by taking a dose of the one target component drug in the combined drug as a horizontal coordinate and an expected additive effect obtained by equivalently converting the combined drug into each component drug as a vertical coordinate, and the equivalent conversion is performed according to a drug sequence of each component drug in the obtained combined drug.

The second obtaining module 30 is configured to obtain an actual dose-effect relationship curve formed by an actual effect value of the combined drug with a dose change of the one target component drug in the combined drug.

The first comparison module 50 is configured to compare a positional relationship between the actual dose-effect relationship curve and the dose-effect curve band.

The first output module 71 is configured to output the efficacy of the combined drug as a synergistic effect when the actual dose-effect relationship curve is located above the dose-effect curve band.

The second output module 73 is configured to output the efficacy of the combined drug as an antagonistic effect when the actual dose-effect relationship curve is located below the dose-effect curve band.

The third output module 75 is configured to output the efficacy of the combined drug as an additive effect when the actual dose-effect relationship curve is located within a range of the dose-effect curve band.

In the solutions of the embodiment of the present disclosure, after the dose-effect curve band and the actual dose-effect relationship curve of the expected additive effect of the combined drug are respectively obtained by the first obtaining module and the second obtaining module, the positional relationship between the actual dose-effect relationship curve and the dose-effect curve band is compared using the first comparison module to obtain a comparison result. And at last, according to different comparison results, the first output module, the second output module or the third output module are selected to respectively output different efficacies of the combined drug.

In the solutions of the embodiment of the present disclosure, the dose-effect curve band of the combined drug can express the expected additive effect of the combined drug with a mathematical function and meets the dose-effect relationship of the drug and the pharmacodynamic characteristics when multiple drugs are in the combined use. In addition, the dose-effect curve further Integrates influences of a sequence that the drugs take the effect and influences of a precedence sequence that an efficacy execution unit executes each component drug in the combined drug on the efficacy of the final combined drug. Therefore, by comparing the positional relationship between the dose-effect curve band and the actual dose-effect relationship curve of the combined drug, not only can the efficacy of the combined drug be accurately obtained, but also various indexes relevant to the combined drug can be got.

Specifically, after the dose-effect relationship curve of each component drug in the combined drug is obtained by the first obtaining module, the expected additive effect of the combined drug is equivalently converted into the expected additive effect of each component drug according to an equivalent conversion principle; then, the equivalent dose-effect curve of the expected additive effect of each combined drug with the dose change of the one target component drug is established; and then, the curve band enclosed by two equivalent dose-effect curves at the most periphery in multiple equivalent dose-effect curves is obtained, and thus, the dose-effect curve band of the expected additive effect of the combined drug is obtained. And meanwhile, after the actual dose-effect relationship curve of the actual effect value of the combined drug with the dose change of the one target component drug in the combined drug is obtained by the second obtaining module, the comparison of the first comparison module on the positional relationship between the dose-effect curve band and the actual dose-effect curve is performed. And at last, according to a comparison result that the actual dose-effect curve is located above, below or within the range of the dose-effect curve band, the efficacy of the combined drug is correspondingly output as the synergistic, antagonistic or additive effects using the first output module, the second output module or the third output module.

In the embodiment, according to drug types in the combined drug and different combined sequences of the component drugs, by respectively and equivalently converting the expected additive effect of the combined drug into the equivalent dose-effect curve of each component drug, the obtained dose-effect curve of the expected additive effect of the combined drug is the same as the dose-effect curve of each component drug in itself. Since the additive effect is a zero interaction, and when the multiple drugs are simultaneously exposed to each efficacy execution unit in a body tissue, a sequential order that the drugs take the effect is random, the expected additive effect of the combined drug is a sum of effects of all efficacy execution units. An efficacy exertion sequence of one efficacy execution unit is an effect that upon an effect exerted by a first component drug A, a B exerts an own dose again along a dose-effect curve of the B, and that of the other efficacy execution unit may be an effect that upon the effect exerted by the second component B, the A exerts an own dose again along a dose-effect curve of the A.

Therefore, when two drugs are combined at a certain determined dose (Am and Bn), the expected additive effect is a range, namely the number set; two expected additive effect values are boundary values of the number set, and respectively represent all efficacy execution units are hundred-percent Am→Bn and hundred-percent Bn→Am, and the middle numerical range is a an accumulative sum for the efficacy of Am→Bn and Bn→Am efficacy execution units at different proportions. The expected additive effect value in the range of the number set is more suitable for the dose-effect curve band relationship, rather than a straight line in the conventional art.

In the first obtaining module, the process of obtaining the dose-effect curve band may be formed by establishing multiple equivalent dose-effect curves; and the establishment of the equivalent dose-effect curves may be implemented by an equivalent dose-effect curve establishment module.

Optionally, the combined drug includes a first component drug A and a second component drug B. The processing apparatus further includes an equivalent dose-effect curve establishment module, the equivalent dose-effect curve establishment module being configured to establish multiple equivalent dose-effect curves before a step that the first obtaining module obtains the dose-effect curve band of the expected additive effect of the combined drug. The equivalent dose-effect curve establishment module includes: a first obtaining module, a second obtaining module, a first finding module, a second finding module, a first calculation unit, a third finding unit, a first conversion unit, a first curve establishment unit, a fourth finding unit, a fifth finding unit, a second calculation unit, a sixth finding unit, a second conversion unit and a second curve establishment unit, wherein the first obtaining unit is configured to obtain a first dose-effect relationship curve $Y=f(x)$ of the first component drug A; the second obtaining module is configured to obtain a second dose-effect relationship curve $Y=g(x)$ of the second component drug B; the first finding module is configured to find an effect value $f(Am)$ of the first component drug A under a combined dose Am on the first dose-effect relationship curve $Y=f(x)$; the second finding unit is configured to find an equivalent dose value Bm same as the effect value $f(Am)$ and corresponding to an effect value $g(Bm)$ of the second component drug B on the second dose-effect relationship curve $Y=g(x)$; the first calculation unit is configured to calculate a dose sum of a combined dose Bn and the equivalent dose Bm of the second component drug B; the third finding unit is configured to find a corresponding effect value $g(Bn+Bm)$ when the dose of the second component drug B on the second dose-effect relationship curve $Y=g(x)$ is the dose sum; the first conversion unit is configured to convert the effect value $g(Bn+Bm)$ into an expected additive effect value $Y(Am+Bn)$ of the combined drug; the first curve establishment unit is configured to establish a first equivalent dose-effect curve $Y(Am+Bn)=g(Bn+Bm)$ of the expected additive effect value $Y(Am+Bn)$ of the combined drug with a dose change of the first component drug A; the fourth finding unit is configured to find or calculate an effect value g(Bn) of the second component drug B under a combined dose Bn on the second dose-effect relationship curve Y=g(x); the fifth finding unit is configured to find or calculate an equivalent dose value An same as the effect value g(Bn) and corresponding to an effect value f(An) of the first component drug A on the first dose-effect relationship curve Y=f(x); the second calculation unit is configured to calculate a dose sum (Am+An) of a combined dose Am and the equivalent dose An of the first component drug A; the sixth finding unit is configured to find or calculate a corresponding effect value f(Am+An) when the dose of the first component drug A on the first dose-effect relationship curve Y=f(x) is the dose sum (Am+An); the second conversion unit is configured to convert the effect value f(Am+An) into the expected additive effect value Y(Am+Bn) of the combined drug; and the second curve establishment unit is configured to establish a second equivalent dose-effect curve Y(Am+Bn)=f(Am+An) of the expected additive effect value of the combined drug with the dose change of the first component drug A.

In the embodiment, the equivalent dose-effect curve establishment module respectively obtains a dose-effect relationship curve of component drug via the first obtaining unit and the second obtaining unit; then the first finding unit, the second finding unit and the first calculation unit are executed to equivalently convert the effect generated under the combined dose of the first component drug A to the second component drug B; thereafter, the third finding unit is executed to obtain a corresponding effect value when the expected additive effect of the combined drug is equivalently converted into the dose sum of the second component drug B; and at last, the first curve establishment unit is executed to establish the first equivalent dose-effect curve Y(Am+Bn)=g(Bn+Bm) of the expected additive effect of the combined drug with the dose change of the first component drug A; the fourth finding unit is configured to find or calculate an effect value g(Bn) of the second component drug B under a combined dose Bn on the second dose-effect relationship curve Y=g(x); the fifth finding unit is configured to find or calculate an equivalent dose value An same as the effect value g(Bn) and corresponding to an effect value f(An) of the first component drug A on the first dose-effect relationship curve Y=f(x); the second calculation unit is configured to calculate a dose sum (Am+An) of a combined dose Am and the equivalent dose An of the first component drug A; the sixth finding unit is configured to find or calculate a corresponding effect value f(Am+An) when the dose of the first component drug A on the first dose-effect relationship curve Y=f(x) is the dose sum (Am+An); next, the second conversion unit is executed to convert the effect value f(Am+An) into the expected additive effect value Y(Am+Bn) of the combined drug; and at last the second curve establishment unit is executed to establish a second equivalent dose-effect curve Y(Am+Bn)=f(Am+An) of the expected additive effect value of the combined drug with the dose change of the first component drug A.

When two drugs are in the combined use, the first component drug A and the second component drug B are not specifically referred to two drugs, and may be continuously updated with different types and sequences of the component drugs. Therefore, in the equivalent dose-effect curve establishment module, the dose-effect relationship curve information between the first component drug A and the second component drug B is also updated at any time with the different types and sequences of the drugs. For example, when the second component drug B is updated into the first component drug A, the equivalent dose-effect curve establishment module equivalently converts the efficacy of the combined drug into the equivalent dose-effect curve of the first component drug A. The first obtaining module establishes each of the equivalent dose-effect curves via the equivalent dose-effect curve establishment module. The first obtaining module can obtain the dose-effect curve band of the expected additive of the combined drug by getting two equivalent dose-effect curves at the most periphery in all equivalent dose-effect curves.

Similarly, when the first component drug A is updated into a combination of (a+b) two drugs and the second component drug is updated into a third drug c, or when four drugs, five drugs . . . and n drugs are in the combined use, there only needs to update a drug combined sequence, the equivalent dose-effect curve establishment module is repeatedly executed, and through gradual iterative loop, all equivalent dose-effect curves can be established; and then, by obtaining the curve band enclosed by the curves at the most periphery in all equivalent dose-effect curves, the dose-effect curve band of the expected additive effect when multiple drugs are in the combined use can be obtained.

Optionally, the processing apparatus further includes: a first calculation module, and a fourth output module; the first calculation unit is configured to calculate a corresponding first dose range of the one target component drug when the actual dose-effect relationship curve is located above the dose-effect curve band after the first output module outputs the efficacy of the combined drug as the synergistic effect; and the fourth output module is configured to output the first dose range as a synergistic dose range of the one target component drug.

Specifically, the first calculation module can obtain a dose of the one target component drug at an intersection of the actual dose-effect relationship curve and the dose-effect curve band according to a function relationship between the actual dose-effect relationship curve and the dose-effect curve band, thereby calculating according to the dose to obtain a corresponding first dose range located above the intersection and belonging to the synergistic effect.

Optionally, the processing apparatus further includes: a third obtaining module, configured to obtain a combined relationship between the one target component drug and rest component drugs in the combined drug after the fourth output module outputs the first dose range as the synergistic dose range of the one target component drug; a second calculation module, configured to calculate synergistic dose ranges of the rest component drugs in the combined drug under a combined condition according to the combined relationship; and a fifth output module, configured to output the synergistic dose ranges of the rest component drugs.

Specifically, the combined relationship between the one target component drug and the rest component drugs in the combined drug is obtained by the third obtaining module according to the combined relationship of each component drug in the combined drug. For example, when the combined drug includes A, B and C, the three drugs are combined according to the fixed proportion of A:B:C=2:2:5 (μg/ml+μg/ml+μg/ml). When the A is the target component drug, according to the dose at the intersection of the expected additive effect curve band and the actual dose-effect relationship curve of the three drugs in the combined use, the synergistic dose range of the A component drug can be calculated when the efficacy of the combined drug is the synergistic effect. According to a mixture relationship that the A component drug and the B component drug are 1:1, the third obtaining module can obtain the mixture relationship that the A component drug and the B component drug are 1:1, and then the second calculation unit calculates according to the synergistic dose range, output by the fourth output module, of the one target component drug to obtain the synergistic dose range of the component drug B. similarly, according to a mixture relationship that the A component drug and the B component drug is 2:5, the synergistic dose range of the C component drug also can be obtained.

Similarly, when the combined drug is combined in terms of other combined relationships, the synergistic dose ranges of the rest component drugs also may be obtained according to different specific combined relationships. For example, when the A and the B are combined, the A at the fixed 1 ng/ml concentration and the B at different concentrations (μg/ml) are combined and the synergistic dose range of the target drug B is obtained, the synergistic dose range of the A component drug is a fixed dose in the combined use.

On the basis of obtaining the synergistic dose range of each component, by combining the synergistic dose range of each component according to the combined relationship, the synergistic dose range when the efficacy of the combined drug is the synergistic effect can be obtained.

Optionally, the processing apparatus further includes: a third calculation module, configured to calculate a corresponding second dose range of the one target component drug when the actual dose-effect relationship curve is located below the dose-effect curve band after the second output module outputs the efficacy of the combined drug as the antagonistic effect; and a sixth module, configured to output the second dose range as an antagonistic dose range of the one target component drug.

Specifically, the method of the third calculation module for calculating the corresponding second dose range of the one target component drug when the actual dose-effect relationship curve is located below the dose-effect curve band also can obtain a range of doses when the effect is located below the dose effect according to corresponding doses when the actual dose-effect relationship curve is located at the Intersection with the dose-effect curve band, namely an antagonistic dose range of the one target component drug.

Optionally, the processing apparatus further includes: a fourth obtaining module, configured to obtain a combined relationship between the one target component drug and rest component drugs in the combined drug after the sixth output module outputs the second dose range as the antagonistic dose range of the one target component drug; a fourth calculation module, configured to calculate antagonistic dose ranges of the rest component drugs in the combined drug under a combined condition according to the combined relationship; and a seventh output module, configured to output the antagonistic dose ranges of the rest component drugs.

Specifically, the method of the fourth obtaining module and the fourth calculation module for calculating the antagonistic dose ranges of the rest component drugs is the same as the method for calculating the synergistic dose ranges; and the antagonistic dose ranges of the rest component drugs are obtained according to the calculation method same as the synergistic dose ranges after an antagonistic dose range of the one target component drug according to the combined relationship among each component drug in the combined drug is obtained.

Optionally, behind the third output module, the processing apparatus further includes: a fifth calculation module, configured to calculate a corresponding third dose range of the one target component drug when the actual dose-effect relationship curve is located within the range of the dose-effect curve band after the third output module outputs the efficacy of the combined drug as the additive effect; and an eighth module, configured to output the third dose range as an additive dose range of the one target component drug.

Specifically, the method of the fifth calculation module for calculating the additive dose range of the one target component drug is the same as that for calculating the synergistic dose range. The intersections of the actual dose-effect curve and the dose-effect curve band are a minimum dose and a maximum dose of the one target component drug when the combined drug is in the additive effect, and the doses between the two doses are a dose range of the additive effect.

Optionally, behind the eighth output module, the processing apparatus further includes: a fifth obtaining module, configured to obtain a combined relationship between the one target component drug and rest component drugs in the combined drug after the eighth output module outputs the third dose range as the additive dose range of the one target component drug; a sixth calculation module, configured to calculate additive dose ranges of the rest component drugs in the combined drug under a combined condition according to the combined relationship; and a ninth output module, configured to output the additive dose ranges of the rest component drugs.

Specifically, the method of the fifth obtaining module and the sixth calculation module for calculating the additive dose ranges of the rest component drugs is the same as that for calculating the synergistic dose ranges; and the additive dose ranges of the rest component drugs are obtained according to the calculation method same as the synergistic dose ranges after an additive dose range of the one target component drug according to the combined relationship among each component drug in the combined drug is obtained.

Optionally, the first comparison module includes: a first obtaining sub-module, configured to obtain a minimum value and a maximum value of an expected additive effect of a corresponding combined drug in a range of the dose-effect curve band under a specific combined dose of the one target component drug; a second obtaining sub-module, configured to obtain an actual effect value of the corresponding combined drug on the actual dose-effect relationship curve under the specific combined dose of the one target component drug; a first calculation sub-module, configured to calculate a first ratio of the actual effect value to the minimum value of the expected additive effect; a second calculation sub-module, configured to calculate a second ratio of the actual effect value to the maximum value of the expected additive effect; a first labeling sub-module, configured to respectively label the first ratio and the second ratio as $CI_{d1}$ and $CI_{d2}$; a first determining sub-module, configured to determine that the actual dose-effect relationship curve is located above the dose-effect curve band when the $CI_{d1}$ and the $CI_{d2}$ both are greater than 1; a second determining sub-module, configured to determine that the actual dose-effect relationship curve is located below the dose-effect curve band when the $CI_{d1}$ and the $CI_{d2}$ both are smaller than 1; and a third determining module, configured to determine that the actual dose-effect relationship curve is located within the range of the dose-effect curve band when either the $CI_{d1}$ or the $CI_{d2}$ is greater than or equal to 1 or is smaller than or equal to 1.

The embodiment is convenient to judge the positional relationship between the actual dose-effect relationship curve and the dose-effect curve band on different effect value levels under any given dose. When the same dose is given, corresponding effect values on the actual dose-effect relationship curve are respectively compared with minimum values and maximum values of corresponding expected additive effects on the dose-effect curve band, thereby obtaining combination indexes $CI_{d1}$ and $CI_{d2}$ based on the dose. According to the $CI_{d1}$ and the $CI_{d2}$ simultaneously being greater than 1, it can be judged that the actual dose-effect relationship curve is located above the dose-effect curve band. According to the $CI_{d1}$ and the $CI_{d2}$ simultaneously being smaller than 1, it can be judged that the actual dose-effect relationship curve is located above dose-effect curve band. According to either the $CI_{d1}$ or the $CI_{d2}$ being greater than or equal to 1 or either the $CI_{d1}$ or the $CI_{d2}$ being smaller than or equal to 1, it is indicated that one actual effect value is within the dose-effect curve band of the expected additive effect and the effect is the additive effect.

Optionally, the processing apparatus further includes an eleventh output module, configured to output the $CI_{d1}$ and the $CI_{d2}$ after the first labeling sub-module respectively labels the first ratio and the second ratio as the $CI_{d1}$ and the $CI_{d2}$. The module may output according to requirements on specific values of the combined dose in actual applications.

Optionally, the first comparison module includes: a third obtaining sub-module, configured to obtain a minimum value and a maximum value of corresponding doses of the one target component drug when the combined drug generates a specific effect on the dose-effect curve band; a fourth obtaining sub-module, configured to obtain an actual combined dose required when the combined drug generates the specific effect on the actual dose-effect relationship curve; a third calculation sub-module, configured to calculate a third ratio of the actual combined dose to the minimum value; a fourth calculation sub-module, configured to calculate a fourth ratio of the actual combined dose to the maximum value; a second labeling sub-module, configured to respectively label the third ratio and the fourth ratio as $CI_{e1}$ and $CI_{e2}$; a fourth determining sub-module, configured to determine that the actual dose-effect relationship curve is located above the dose-effect curve band when the $CI_{e1}$ and the $CI_{e2}$ both are smaller than 1; a fifth determining sub-module, configured to determine that the actual dose-effect relationship curve is located below the dose-effect curve band when the $CI_{e1}$ and the $CI_{e2}$ both are greater than 1; and a sixth determining sub-module, configured to determine that the actual dose-effect relationship curve is located within the range of the dose-effect curve band when either the $CI_{e1}$ or the $CI_{e2}$ is greater than or equal to 1 or is smaller than or equal to 1.

The embodiment is convenient to compare the positional relationship between the actual dose-effect curve and the dose-effect curve band in different dose ranges under any given efficacy level. When it is at a specific efficacy value such as $ED_{50}$, the vertical coordinate on the dose-effect relationship curve band of the combined drug is a straight line drawn parallel to the horizontal coordinate at 50, and is respectively intersected with the dose-effect curve band and the actual dose-effect curve at A, B and C, and thus horizontal coordinate values at A, B and C are obtained and are assumed to be 1.012, 1.321 and 1.450. At the efficacy $ED_{50}$, a minimum value of a dose of an expected additive effect of the one target component drug is 1.012, a maximum value is 1.321 and the dose of the actual effect is 1.450. Since $CI_{e1}=1.450/1.012>1$, $CI_{e2}=1.450/1.321>1$, it is indicated that when same efficacy is generated, the dose of the one target component drug actually needed to be given is greater than the expected dose. Therefore, under the effect value, the actual dose-effect relationship curve is located below the dose-effect curve band. If the $CI_{e1}$ and the $CI_{e2}$ are smaller than 1, it is determined that the actual dose-effect relationship curve is located above the dose-effect curve band and the efficacy is antagonistic. If the $CI_{e1}$ and the $CI_{e2}$ are greater than 1, it is determined that the actual dose-effect relationship curve is located below the dose-effect curve band. If the $CI_{e1}$ or the $CI_{e2}$ is greater than or equal to 1, it is determined that the actual dose-effect relationship curve is located within the range of the dose-effect curve band.

The positional relationship comparison method in the embodiment is based on the dose-effect curve band, and is based on two effect values or two dose values of the expected additive effect on the dose-effect curve band under a same dose condition or a given efficacy level, so the efficacy of the combined drug can be detected quantitatively and more accurately according to the combination indexes of the combined drug. For example, when the $CI_{e1}<1$ and the $CI_{e2}<1$, it is determined that the actual dose-effect relationship curve is located below the dose-effect curve band and the efficacy of the combined drug is the synergistic effect. The further the specific value of the $CI_{e1}$ and the $CI_{e2}$ to 1 is, the stronger the synergistic effect of the combined drug is. The closer the specific value of the $CI_{e1}$ and the $CI_{e2}$ to 1 is, the weaker the synergistic effect of the combined drug is. Therefore, the efficacy level of the combined drug can be detected quantitatively.

Optionally, the processing apparatus further includes a twelfth output module, configured to output the $CI_{d1}$ and the $CI_{d2}$ after the second labeling sub-module respectively labels the third ratio and the fourth ratio as the $CI_{e1}$ and the $CI_{e2}$. The output module can meet requirements on the effect combination index in actual applications.

Each module provided in the embodiments and use methods provided by corresponding steps of the method embodiments are the same, and the application scenes also may be the same. Of course, it is to be noted that solutions involved by the above modules may be not limited to contents and scenes in the embodiments. The modules can be operated at a computer terminal or a mobile terminal, and may be implemented by software or hardware.

An embodiment of the present disclosure further may provide a computer terminal. The computer terminal may be any computer terminal device in a computer terminal group. Optionally, in the embodiment, the computer terminal also may be replaced as a terminal device such as a mobile terminal.

Optionally, the computer terminal may include: one or more processors, a memory and a transmission apparatus.

Herein, the memory may be configured to store a software program and module, for example, program instructions/modules corresponding to the processing method and apparatus for the efficacy of the combined drug in the embodiments of the present disclosure. The processor runs the software program and module in the memory to implement various function application and data processing, that is, implement the processing method for the efficacy of the combined drug. The memory may include a high speed random access memory, and may further include a non-volatile memory, for example, one or more magnetic storage apparatuses, a flash memory, or another non-volatile solid-state memory. In some examples, the memory may further include a memory disposed remote to the processor, and the memory may be connected to the terminal through a network. Examples of the network include, but are not limited to, the Internet, an intranet, a local area network, a mobile communications network, or a combination thereof.

The processor may invoke information and an application program stored by the memory via the transmission apparatus, so as to implement the following steps: obtaining a dose-effect curve band of an expected additive effect of the combined drug, wherein the dose-effect curve band is enclosed by two equivalent dose-effect curves at the most periphery in multiple equivalent dose-effect curves, each of the equivalent dose-effect curves is a curve established by taking a dose of the one target component drug in the combined drug as a horizontal coordinate and an expected additive effect obtained by equivalently converting the combined drug into each component drug as a vertical coordinate, and the equivalent conversion is performed according to a drug sequence of each component drug in the obtained combined drug; obtaining an actual dose-effect relationship curve formed by an actual effect value of the combined drug with a dose change of the one target component drug in the combined drug; comparing a positional relationship between the actual dose-effect relationship curve and the dose-effect curve band; and outputting the efficacy of the combined drug as a synergistic effect when the actual dose-effect relationship curve is located above the dose-effect curve band, outputting the efficacy of the combined drug as an antagonistic effect when the actual dose-effect relationship curve is located below the dose-effect curve band, and outputting the efficacy of the combined drug as an additive effect when the actual dose-effect relationship curve is located within a range of the dose-effect curve band.

Optionally, the combined drug includes a first component drug A and a second component drug B. Before the step of obtaining the dose-effect curve band of the expected additive effect of the combined drug, the processing method further includes a step of establishing multiple equivalent dose-effect curves, wherein the step of establishing the multiple equivalent dose-effect curves includes: obtaining a first dose-effect relationship curve $Y=f(x)$ of the first component drug A; obtaining a second dose-effect relationship curve $Y=g(x)$ of the second component drug B; finding or calculating an effect value $f(Am)$ of the first component drug A under a combined dose Am on the first dose-effect relationship curve $Y=f(x)$; finding or calculating an equivalent dose value Bm same as the effect value $f(Am)$ and corresponding to an effect value $g(Bm)$ of the second component drug B on the second dose-effect relationship curve $Y=g(x)$; calculating a dose sum $(Bn+Bm)$ of a combined dose Bn and the equivalent dose Bm of the second component drug B; finding to obtain a corresponding effect value $g(Bn+Bm)$ when the dose of the second component drug B on the second dose-effect relationship curve $Y=g(x)$ is the dose sum $(Bn+Bm)$; converting the effect value $g(Bn+Bm)$ into an expected additive effect value $Y(Am+Bn)$ of the combined drug; establishing a first equivalent dose-effect curve $Y(Am+Bn)=g(Bn+Bm)$ of the expected additive effect value $Y(Am+Bn)$ of the combined drug with a dose change of the first component drug A; finding or calculating an effect value $g(Bn)$ of the second component drug B under a combined dose Bn on the second dose-effect relationship curve $Y=g(x)$; finding or calculating an equivalent dose value An same as the effect value $g(Bn)$ and corresponding to an effect value $f(An)$ of the first component drug A on the first dose-effect relationship curve $Y=f(x)$; calculating a dose sum $(Am+An)$ of a combined dose Am and the equivalent dose An of the first component drug A; finding or calculating a corresponding effect value $f(Am+An)$ when the dose of the first component drug A on the first dose-effect relationship curve $Y=f(x)$ is the dose sum $(Am+An)$; converting the effect value $f(Am+An)$ into the expected additive effect value $Y(Am+Bn)$ of the combined drug; establishing a second equivalent dose-effect curve $Y(Am+Bn)=f(Am+An)$ of the expected additive effect value of the combined drug with the dose change of the first component drug A.

Through the processing method of the present disclosure, by comparing with the actual dose-effect curve of the combined drug based on the dose-effect curve band of the expected additive effect of the combined drug, and then judging the efficacy of the combined drug via the positional relationship between the actual dose-effect curve and the dose-effect curve band, since the dose-effect curve band is more suitable for the dose-effect relationship of the drug and pharmacodynamic basic characteristics when the drug is in the combined use, the efficacy processing method of the embodiments integrates different drug sequences when multiple drugs are in the combined use and influences of different dose-effect relationships of different drugs on the efficacy of the combined drug. It not only can implement detection on the efficacy when multiple (two or more) drugs are in the combined use, but also can implement quantitative detection. The processing method solves the problem that the efficacy cannot be accurately detected when multiple drugs are in the combined use in the conventional art. Moreover, the efficacy, obtained by the detection, of the combined drug can be widely applied to research and development of a compound drug, toxicological study and environmental evaluation. In addition, dose ranges that the multiple drugs generate the synergistic, additive and antagonistic effects under different combined conditions and related indexes combined with other drugs further can be quantitatively calculated as needed.

An embodiment of the present disclosure further provides a storage medium. Optionally, in the embodiment, the storage medium may be configured to store a program code executed by the processing method for the efficacy of the combined drug provided by the embodiment.

Optionally, in the embodiment, the storage medium may be located in any computer terminal in a computer terminal group of a computer network, or located in any mobile terminal in a mobile terminal group.

Optionally, in the embodiment, the storage medium is configured to a program code for executing the following steps:

obtaining a dose-effect curve band of an expected additive effect of the combined drug, wherein the dose-effect curve band is enclosed by two equivalent dose-effect curves at the most periphery in multiple equivalent dose-effect curves, each of the equivalent dose-effect curves is a curve established by taking a dose of the one target component drug in the combined drug as a horizontal coordinate and an expected additive effect obtained by equivalently converting the combined drug into each component drug as a vertical coordinate, and the equivalent conversion is performed according to a drug sequence of each component drug in the obtained combined drug; obtaining an actual dose-effect relationship curve formed by an actual effect value of the combined drug with a dose change of the one target component drug in the combined drug; comparing a positional relationship between the actual dose-effect relationship curve and the dose-effect curve band; and outputting the efficacy of the combined drug as a synergistic effect when the actual dose-effect relationship curve is located above the dose-effect curve band, outputting the efficacy of the combined drug as an antagonistic effect when the actual dose-effect relationship curve is located below the dose-effect curve band, and outputting the efficacy of the combined drug as an additive effect when the actual dose-effect relationship curve is located within a range of the dose-effect curve band.

Optionally, the storage medium is configured to store a program code for executing the following steps, and a step of forming each of the equivalent dose-effect curves includes: obtaining a first dose-effect relationship curve $Y=f(x)$ of the first component drug A; obtaining a second dose-effect relationship curve $Y=g(x)$ of the second component drug B; finding an effect value $f(Am)$ of the first component drug A under a combined dose Am on the first dose-effect relationship curve Y=f(x); finding an equivalent dose value Bm same as the effect value f(Am) and corresponding to an effect value g(Bm) of the second component drug B on the second dose-effect relationship curve Y=g(x); calculating a dose sum (Bn+Bm) of a combined dose Bn and the equivalent dose Bm of the second component drug B; finding to obtain a corresponding effect value g(Bn+Bm) when the dose of the second component drug B on the second dose-effect relationship curve Y=g(x) is the dose sum (Bn+Bm); converting the effect value g(Bn+Bm) into an expected additive effect value Y(Am+Bn) of the combined drug; establishing a first equivalent dose-effect curve Y(Am+Bn)=g(Bn+Bm) of the expected additive effect value Y(Am+Bn) of the combined drug with a dose change of the first component drug A; finding or calculating an effect value g(Bn) of the second component drug B under a combined dose Bn on the second dose-effect relationship curve Y=g(x); finding or calculating an equivalent dose value An same as the effect value g(Bn) and corresponding to an effect value f(An) of the first component drug A on the first dose-effect relationship curve Y=f(x); calculating a dose sum (Am+An) of a combined dose Am and the equivalent dose An of the first component drug A; finding or calculating a corresponding effect value f(Am+An) when the dose of the first component drug A on the first dose-effect relationship curve Y=f(x) is the dose sum (Am+An); converting the effect value f(Am+An) into the expected additive effect value Y(Am+Bn) of the combined drug; establishing a second equivalent dose-effect curve Y(Am+Bn)=f(Am+An) of the expected additive effect value of the combined drug with the dose change of the first component drug A.

In the solutions of the embodiment of the present disclosure, by comparing with the actual dose-effect curve of the combined drug based on the dose-effect curve band of the expected additive effect of the combined drug, and then judging the efficacy of the combined drug via the positional relationship between the actual dose-effect curve and the dose-effect curve band, since the dose-effect curve band is more suitable for the dose-effect relationship of the drug and pharmacodynamic basic characteristics when the drug is in the combined use, the efficacy processing method of the embodiments integrates different drug sequences when multiple drugs are in the combined use and influences of different dose-effect relationships of different drugs on the efficacy of the combined drug. It not only can implement detection on the efficacy when multiple (two or more) drugs are in the combined use, but also can Implement quantitative detection. The processing method solves the problem that the efficacy cannot be accurately detected when multiple drugs are in the combined use in the conventional art. Moreover, the efficacy, obtained by the detection, of the combined drug can be widely applied to research and development of a compound drug, toxicological study and environmental evaluation. In addition, dose ranges that the multiple drugs generate the synergistic, additive and antagonistic effects under different combined conditions and related indexes combined with other drugs further can be quantitatively calculated as needed.

The sequence numbers of the foregoing embodiments of the present disclosure are merely for Illustrative purposes, and are not intended to indicate priorities of the embodiments.

In the foregoing embodiments of the present disclosure, the description of each embodiment has a respective focus. For the part that is not detailed in an embodiment, refer to the relevant description of other embodiments.

In the several embodiments provided in the present disclosure, it should be understood that the disclosed technical contents may be implemented in another manner. The described apparatus embodiments are merely exemplary. For example, the unit division is merely logical function division and may be another division manner during actual implementation. For example, multiple units or components may be combined or integrated into another system, or some features may be ignored or not performed. In addition, the displayed or discussed mutual couplings or direct couplings or communication connections may be indirect couplings or communication connections implemented by using some interfaces, units, or modules, or may be implemented in electronic, mechanical, or other forms.

The units described as separate parts may or may not be physically separate, and parts displayed as units may or may not be physical units, may be located in one position, or may be distributed on a plurality of network units. Some or all of the units may be selected according to actual needs to achieve the objectives of the solutions of the embodiments.

In addition, functional units in the embodiments of the present disclosure may be integrated into one processing unit, or each of the units may exist alone physically, or two or more units are integrated into one unit. The integrated unit may be implemented in a form of hardware, or may be implemented in a form of a software functional unit.

The integrated units in case of being implemented in a form of a software functional unit and taken as a separate product to be sold or used may be stored to a computer readable storage medium.

Based on such understanding, the technical solutions of the present disclosure or the part that makes contributions to the existing technology may be substantially embodied in the form of a software product. The computer software product is stored in a storage medium, and contains several instructions for instructing a computer device (which may be a computer, a server, or a network device) to perform the steps of the method in part or in whole according to the embodiments of the present disclosure. The foregoing storage medium includes, but is not limited to: any medium that can store program code, such as a USB flash drive, an ROM (Read-Only Memory), an RAM (Random Access Memory), a removable hard disk, a magnetic disk, or an optical disc.

The beneficial effects of the present disclosure will be further described below with reference to specific embodiments.

Embodiment 1: A Processing Method for Efficacy of Two Drugs in Combined Use

1) A drug NX and a drug TX are combined at a fixed proportion.
2) A fixed dose of the drug TX is combined with different doses of the drug NX.

Title: the nitrohydroxyl compound (NX) is an anti-infectious drug. In recent years, it is found that the NX has a targeted anticancer activity and has been approved by SFDA to enter a clinical trial. Taxol (TX) is an anticancer drug frequently used in clinic. In an NX/TX combined application, the growth of a human hepatocellular carcinoma cell HepG2 is inhibited in an MTT method. A method for quantitatively processing relevant indexes of synergistic/additive/antagonistic effect is described, which provides a reference for research and development of a novel anticancer compound.

Part 1: processing method for efficacy of two drugs in combined use at NX/TX fixed proportion of NX: TX=1:1 (μg/ml+ng/ml).

Step 1: a dose-effect relationship table of dose levels of each single drug and each member in a combined group is prepared, and a respective dose-effect relationship curve equation is fitted. For dose-effect relationship data among the NX, the TX and the single drug, the NX+TX at a fixed proportion in combined use (1/1, μg/ml+ng/ml), and dose-effect relationship data of the TX at a fixed concentration (2 ng/ml)+the NX at different concentrations in the combined use, see a table 1.

TABLE 1 dose-effect relationship data of the NX and the TX in single use and combined use

| NX (μg/ml) Single use | | TX (ng/ml) Single use | | NX + TX(1/1) (μg/ml + ng/ml) Fixed proportion | | NX + TX(2) (μg/ml + 2 ng/ml) Fixed concentration of TX | |
|---|---|---|---|---|---|---|---|
| Concentration | Inhibition rate % | Concentration | Inhibition rate % | Concentration | Inhibition rate % | Concentration | Inhibition rate % |
| 0.5 | 5.5 | 0.5 | 4.5 | 0.5 + 0.5 | 19.7 | 0.5 + 2 | 10.1 |
| 1 | 14 | 1 | 14.1 | 1 + 1 | 32.1 | 1 + 2 | 23.8 |
| 2 | 49.2 | 2 | 32.5 | 2 + 2 | 62.9 | 2 + 2 | 67.3 |
| 4 | 84.9 | 4 | 59.3 | 4 + 4 | 86 | 4 + 2 | 88 |
| 8 | 92.9 | 8 | 80.3 | 8 + 8 | 92.2 | 8 + 2 | 92.9 |
| 16 | 94.1 | 16 | 87.4 | 16 + 16 | 95.4 | 16 + 2 | 96.1 |

Dose-effect curve diagrams for the NX and the TX in the single use and for the NX in the combined group are drawn, as shown in FIG. 3A, FIG. 3B, FIG. 3C and FIG. 3D.

Figure 3A:
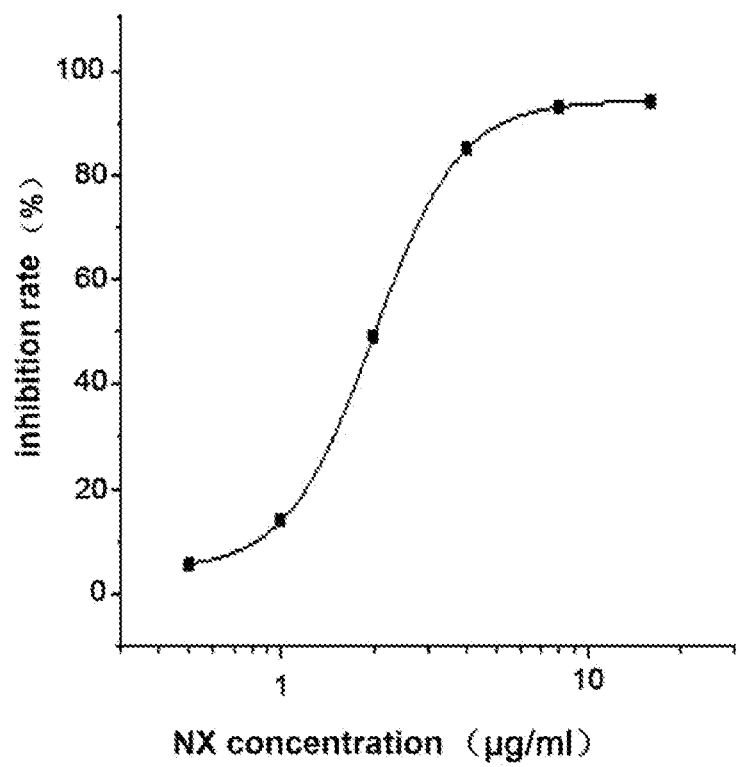
FIG. 3A to FIG. 3D illustrate a dose-effect relationship curve between single use of a nitrohydroxyl compound (NX) and a taxol (TX) and a drug NX in a combined group according to a first embodiment of the present disclosure, wherein the FIG. 3A to the FIG. 3B respectively illustrate a dose-effect relationship curve between two single drugs of the nitrohydroxyl compound (NX) and the taxol (TX), FIG. 3C Illustrates a dose-effect relationship curve of actual efficacy in the combined group with a dose change of the drug NX therein when NX+TX are combined at a fixed proportion.

A dose-effect relationship equation of each diagram is respectively fitted as follows using a logistic program:

Single-use drug NX: $Y=(4.3188-94.209)/\{1+(X/1.9981)^{3.0815}\}+94.209$, with the dose-effect relationship curve as shown in FIG. 3A.

Figure 3B:
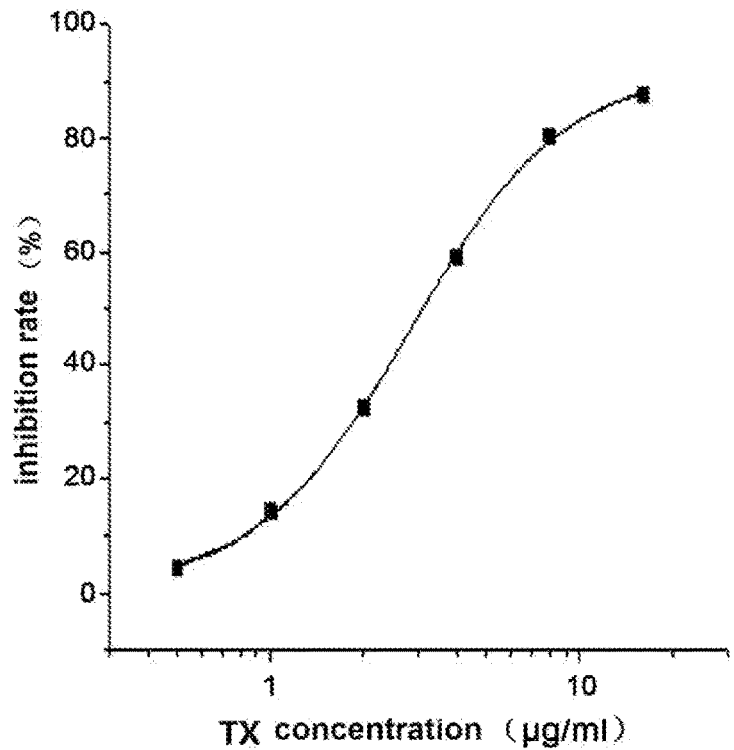

Single-use drug TX: $Y=(0.8779-92.1626)/\{1+(X/2.8494)^{1.7569}\}+92.1626$, with the dose-effect relationship curve as shown in FIG. 3B.

Figure 3C:
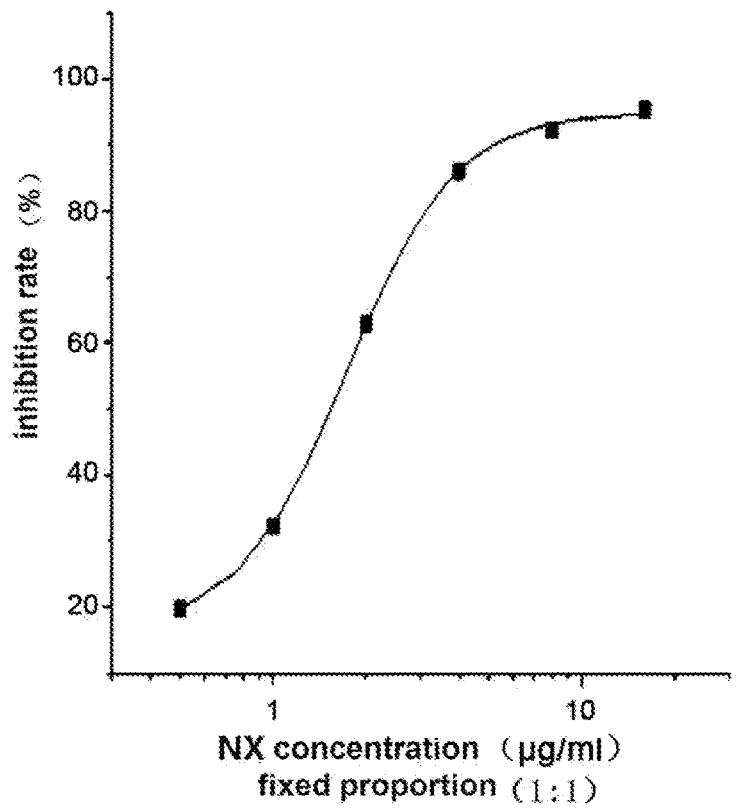

In the combined group at the fixed proportion, NX: $Y=(15.8595-94.9017)/\{1+(X/1.7190)^{2.4490}\}+94.9017$, with the actual dose-effect relationship curve as shown in FIG. 3C.

Figure 3D:
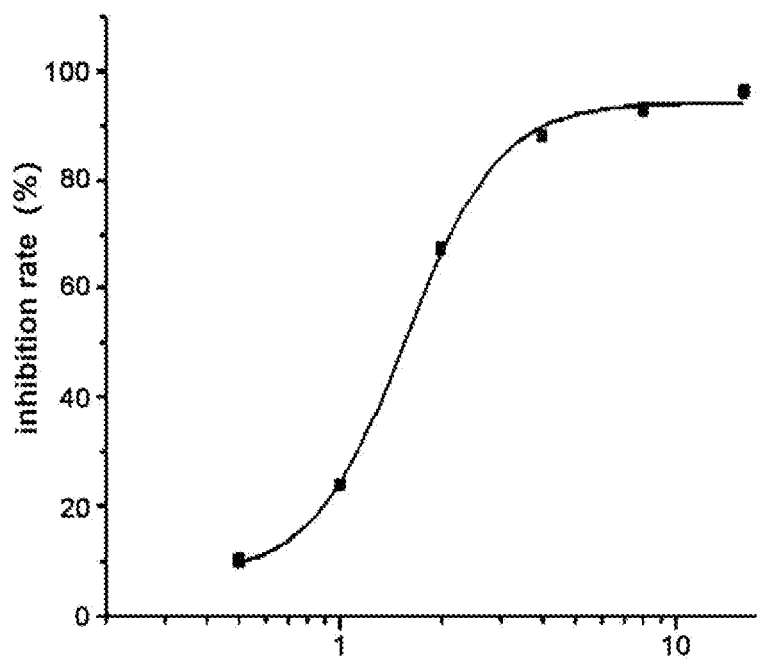

In the combined group at the fixed proportion, TX: $Y=(7.294-94.22)/\{1+(X/1.569)^{3.1080}\}+94.22$, with the actual dose-effect relationship curve as shown in FIG. 3D.

Step 2: the dose is converted sequentially, and each line of the dose-effect relationship data formed into an expected additive efficacy curve band under a combined condition is calculated.

Direct calculation method: several existing combined dose points are evaluated.

Combined dose values for doses in several existing combined groups under the NX/TX fixed proportion after sequential equivalent dose conversion are calculated, with details in a table 2.

TABLE 2 calculation table of expected additive effect after the NX and the TX are combined at the fixed proportion and the equivalent dose conversion is performed sequentially with the NX as the target drug

| Doses in combined group | | Equivalent dose conversion with the NX as the target drug (TX→NX, NX + NX$_{tx}$) | | | |
|---|---|---|---|---|---|
| NX (μg/ml) (1) | TX (ng/ml) (2) | Efficacy of the TX (%) (3) | Equivalent dose of the NX (NX$_{tx}$, μg/ml) (4) | Equivalent dose combination of the NX (NX + NX$_{tx}$, μg/ml) (5) | NX + NX$_{tx}$ expected additive effect (%) (6) |
| 0.5 | 0.5 | 4.9763 | 0.4060 | 0.9060 | 11.5 |
| 1 | 1 | 13.3922 | 0.9827 | 1.9827 | 48.7 |
| 2 | 2 | 32.7687 | 1.5564 | 3.5564 | 81.2 |
| 4 | 4 | 59.7311 | 2.3307 | 6.3307 | 91.7 |
| 8 | 8 | 79.3653 | 3.3807 | 11.3807 | 93.8 |
| 16 | 16 | 87.9614 | 4.6372 | 20.6372 | 94.1 |

Note:

a calculation formula in the table 2: ① NX: $Y = (4.3188 - 94.209)/\{1 + (X/1.9981)^{3.0815}\} + 94.209$; ② TX: $Y = (0.8779 - 92.1626)/\{1 + (X/2.8494)^{1.7569}\} + 92.1626$.

Descriptions on numerical calculation in each column of the table 2: (3) column: data in (2) column are calculated with the formula ②; (4) column: data in (3) column are calculated with the formula ①; (5) column: (1) column+(4) column; (6) column: data in (5) column are calculated with the formula ①.

TABLE 3 calculation table of expected additive effect after the NX and the TX are
combined at the fixed proportion and the equivalent dose conversion is performed
sequentially with the TX as a target drug

| Doses in combined group | | | Equivalent dose conversion with the TX as the target drug $(NX \rightarrow TX, TX + TX_{nx})$ | | $TX + TX_{nx}$ expected additive effect (%) (10) |
|---|---|---|---|---|---|
| NX (μg/ml) (1) | TX (ng/ml) (2) | Efficacy of NX (%) (7) | Equivalent dose of TX $(TX_{nx}, ng/ml)$ (8) | Equivalent dose combination of TX $(TX + TX_{nx}, ng/ml)(9)$ | |
| 0.5 | 0.5 | 5.5596 | 0.5414 | 1.0414 | 14.2 |
| 1 | 1 | 13.8409 | 1.0236 | 2.0236 | 33.2 |
| 2 | 2 | 49.3297 | 3.0565 | 5.0565 | 67.8 |
| 4 | 4 | 84.7367 | 11.3237 | 15.3237 | 87.6 |
| 8 | 8 | 92.9754 | — | — | — |
| 16 | 16 | 94.0615 | — | — | — |

Note:
a calculation formula in the table 3: ① NX: $Y = (4.3188 - 94.209)/\{1 + (X/1.9981)^{3.0815}\} + 94.209$; ② TX: $Y = (0.8779 - 92.1626)/\{1 + (X/2.8494)^{1.7569}\} + 92.1626$.

Descriptions on numerical calculation in each column: (7) column: data in (1) column are calculated with the formula ①; (8) column: data in (7) column are calculated with the formula ②; (9) column: (2) column+(8) column; (10) column: data in (9) column are calculated with the formula ②; "—" indicates to be beyond the dose-effect range of the TX.

Figure 4:
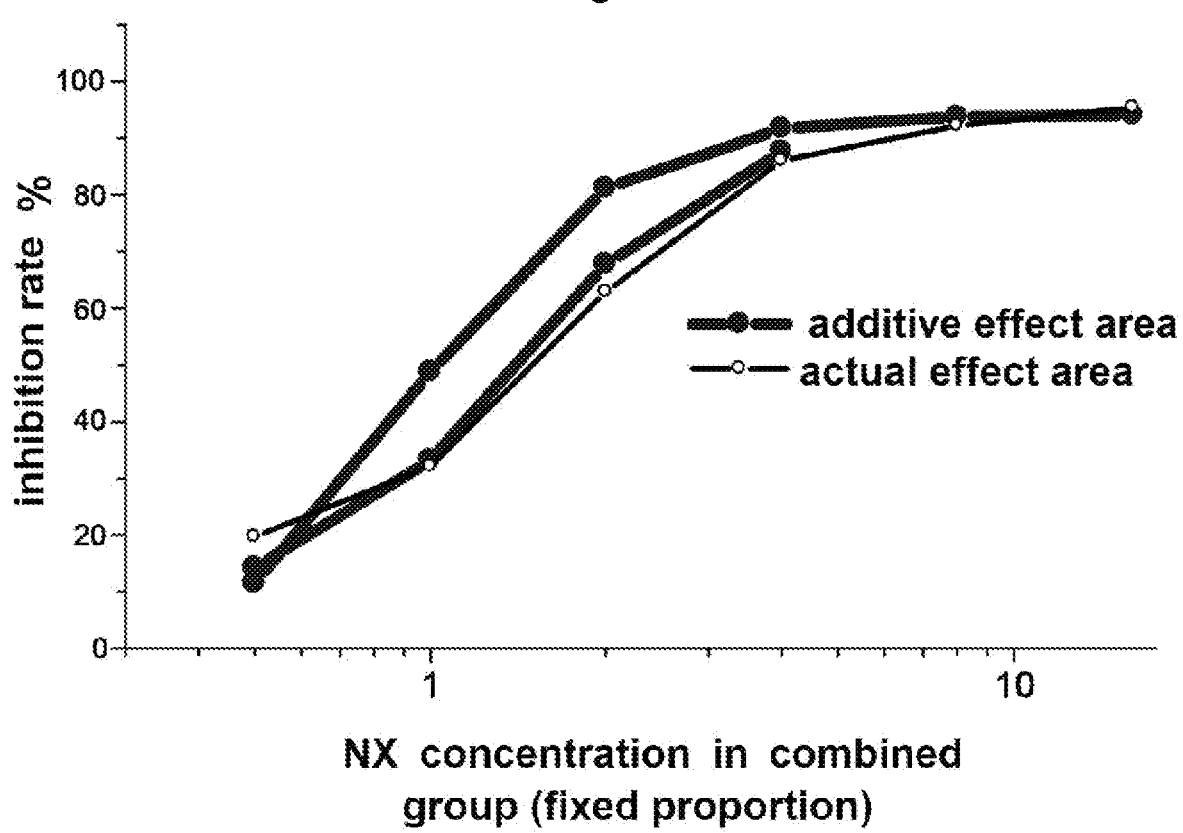
FIG. 4 illustrates a dose-effect curve band diagram and an actual dose-effect relationship curve of an expected additive effect formed by drawing with each dose level of an NX in a combined group as a horizontal coordinate and each expected additive effect value as a vertical coordinate when NX+TX are combined at a fixed proportion.

By drawing a diagram with each dose level of the NX in the combined group as a horizontal coordinate and each expected additive effect value as a vertical coordinate to form a dose-effect curve band of the expected equivalent additive effect, and simultaneously drawing an actual effect curve of the combined group on the diagram as shown in FIG. 4, it may be seen from the FIG. 4 that an area enclosed by two thick curves is the dose-effect curve band of the expected additive effect; the thin curve is the actual dose-effect relationship curve of the combined group and is intersected with the additive effect band. That is to way, in a dose range of the combined group, there are a synergistic effect, an additive effect and an antagonistic effect.

According to the FIG. 4, the expected additive effect of each dose level of the combined group is listed, and combination indexes ($CI_d$) based on the dose are calculated, with details in a table 4.

Descriptions on numerical calculation in each column: (3) column: from the table 2; (4) column: from the table 3; (5) column: from the table 1; (6) column: (5) column data/(3) column data; (7) column: (5) column data/(4) column data; (8) column: standards are referred to the previous $CI_d$ calculation.

Direct calculation method: the synergistic, additive and antagonistic conditions can be judged approximately; the existing dose level in the combined group can be judged. However, there is a relatively big difference in each dose level on the horizontal coordinate, the dose range of each efficacy only can be estimated probably and the dose of each part cannot be determined accurately. The necessity on whether the accurate calculation is performed can be judged. When the dose range of each efficacy needs to be accurately calculated, several intermediate dose values are inserted between each of the dose levels; and according to the determined dose-effect relationship function, after the dose conversion is performed sequentially, the expected additive effect value is calculated and then the function fitting is performed.

Accurate Calculation Method:

In order to improve the fitting precision of the expected additive effect curve band of the combined group, several

TABLE 4

| Doses in combined group | | Expected additive effect value after equivalent dose conversion and combination $(NX + NX_{tx}$ and $TX + TX_{nx})$ | | | | | |
|---|---|---|---|---|---|---|---|
| | | $NX + NX_{tx}$ expected | $TX + TX_{nx}$ expected | | | | |
| NX (μg/ml) (1) | TX (ng/ml) (2) | additive effect (%) (3) | additive effect (%) (4) | Actual effect (%) (5) | $CI_{d1}$ (6) | $CI_{d2}$ (7) | Determination (8) |
| 0.5 | 0.5 | 11.5 | 14.2 | 19.7 | 1.7130 > 1 | 1.3873 > 1 | Synergistic |
| 1 | 1 | 48.7 | 33.2 | 32.1 | 0.6591 < 1 | 0.9669 < 1 | Antagonistic |
| 2 | 2 | 81.2 | 67.8 | 62.9 | 0.7446 < 1 | 0.9277 < 1 | Antagonistic |
| 4 | 4 | 91.7 | 87.6 | 86.0 | 0.9378 < 1 | 0.9817 < 1 | Antagonistic |
| 8 | 8 | 93.8 | — | 92.2 | 0.9829 < 1 | — | Antagonistic |
| 16 | 16 | 94.1 | — | 95.4 | 1.0138 > 1 | — | Synergistic | intermediate dose values are inserted between each of the combined doses as needed. For data in the group, 3-4 inserted values are arranged between each of the doses at intervals. For example, between 0.5+0.5 and 1+1, there increases 0.6+0.6, 0.7+0.7, 0.8+0.8, 0.9+0.9 and the like, as shown in table 5.

Step 1, with the NX as the target drug, after equivalent dose conversion is performed on the TX, equivalent doses are combined and an expected additive effect value is calculated using a dose-effect curve equation of the single-use NX. See data in (3), (4), (5) and (6) columns in the table 4.

TABLE 5 calculation table of expected additive effect after the NX and the TX are combined at the fixed proportion and the equivalent dose conversion is performed sequentially with the NX as the target drug

| Doses in combined group | | Equivalent dose conversion with the NX as the target drug (TX→NX, NX + NX$_{tx}$) | | | |
|---|---|---|---|---|---|
| | | | Equivalent dose | | |
| NX (μg/ml) (1) | TX (ng/ml) (2) | Efficacy of TX (%) (3) | Equivalent dose of NX (NX$_{tx}$, μg/ml) (4) | combination of NX (NX + NX$_{tx}$, μg/ml) (5) | NX + NX$_{tx}$ expected additive effect (%) (6) |
| 0.5 | 0.5 | 4.9763 | 0.4060 | 0.9060 | 11.5 |
| 0.6 | 0.6 | 6.4296 | 0.5960 | 1.1960 | 19.7 |
| 0.7 | 0.7 | 8.0213 | 0.7195 | 1.4195 | 27.6 |
| 0.8 | 0.8 | 9.7270 | 0.8189 | 1.6189 | 35.2 |
| 0.9 | 0.9 | 11.5241 | 0.9051 | 1.8051 | 42.3 |
| 1 | 1 | 13.3922 | 0.9827 | 1.9827 | 48.7 |
| 1.2 | 1.2 | 17.2688 | 1.1207 | 2.3207 | 59.4 |
| 1.4 | 1.4 | 21.2305 | 1.2432 | 2.6432 | 67.5 |
| 1.6 | 1.6 | 25.1792 | 1.3551 | 2.9551 | 73.5 |
| 1.8 | 1.8 | 29.0423 | 1.4589 | 3.2589 | 77.9 |
| 2 | 2 | 32.7687 | 1.5564 | 3.5564 | 81.2 |
| 2.4 | 2.4 | 39.6901 | 1.7364 | 4.1364 | 85.6 |
| 2.8 | 2.8 | 45.8191 | 1.9010 | 4.7010 | 88.2 |
| 3.2 | 3.2 | 51.1569 | 2.0535 | 5.2535 | 89.9 |
| 3.6 | 3.6 | 55.7657 | 2.1962 | 5.7962 | 91.0 |
| 4 | 4 | 59.7311 | 2.3307 | 6.3307 | 91.7 |
| 5 | 5 | 67.3956 | 2.6374 | 7.6374 | 92.8 |
| 6 | 6 | 72.7395 | 2.9105 | 8.9105 | 93.3 |
| 7 | 7 | 76.5600 | 3.1568 | 10.1568 | 93.6 |
| 8 | 8 | 79.3653 | 3.3807 | 11.3807 | 93.8 |
| 10 | 10 | 83.1039 | 3.7736 | 13.7736 | 94.0 |
| 12 | 12 | 85.4029 | 4.1068 | 16.1068 | 94.1 |
| 14 | 14 | 86.9144 | 4.3918 | 18.3918 | 94.1 |
| 16 | 16 | 87.9614 | 4.6372 | 20.6372 | 94.1 |

Calculation formulas: ① NX: $Y=(4.3188-94.209)/\{1+(X/1.9981)^{3.0815}\}+94.209$; ② TX: $Y=(0.8779-92.1626)/\{1+(X/2.8494)^{1.7569}\}+92.1626$. Descriptions on numerical calculation in each column: (3) column: data in (2) column are calculated with the formula ②; (4) column: data in (3) column are calculated with the formula ①; (5) column: (1) column+(4) column; (6) column: data in (5) column are calculated with the formula ①.

Step 2, with the TX as the target drug, after equivalent dose conversion is performed on the NX, equivalent doses are combined and an expected additive effect value is calculated using a dose-effect curve equation of the single-use TX. See data in (7), (8), (9) and (10) columns in the table 6.

TABLE 6 calculation table of expected additive effect after the NX and the TX are combined at the fixed proportion and the equivalent dose conversion is performed sequentially with the TX as the target drug

| Doses in combined group | | Equivalent dose conversion with the TX as the target drug (NX→TX, TX + TXnx) | | | |
|---|---|---|---|---|---|
| NX (μg/ml) (1) | TX (ng/ml) (2) | Efficacy of NX (%) (7) | Equivalent dose of TX ($TX_{nx}$, ng/ml) (8) | Equivalent dose combination of TX (TX + $TX_{nx}$, ng/ml) (9) | TX + $TX_{nx}$ expected additive effect (%) (10) |
| 0.5 | 0.5 | 5.5596 | 0.5414 | 1.0414 | 14.2 |
| 0.6 | 0.6 | 6.4726 | 0.6028 | 1.2028 | 17.3 |
| 0.7 | 0.7 | 7.7324 | 0.6824 | 1.3824 | 20.9 |
| 0.8 | 0.8 | 9.3724 | 0.7797 | 1.5797 | 24.8 |
| 0.9 | 0.9 | 11.4093 | 0.8937 | 1.7937 | 28.9 |
| 1 | 1 | 13.8409 | 1.0236 | 2.0236 | 33.2 |
| 1.2 | 1.2 | 19.7842 | 1.3271 | 2.5271 | 41.7 |
| 1.4 | 1.4 | 26.8326 | 1.6849 | 3.0849 | 49.7 |
| 1.6 | 1.6 | 34.4514 | 2.0934 | 3.6934 | 56.7 |
| 1.8 | 1.8 | 42.0953 | 2.5508 | 4.3508 | 62.7 |
| 2 | 2 | 49.3297 | 3.0565 | 5.0565 | 67.8 |
| 2.4 | 2.4 | 61.6284 | 4.2151 | 6.6151 | 75.2 |
| 2.8 | 2.8 | 70.7302 | 5.5822 | 8.3822 | 80.2 |
| 3.2 | 3.2 | 77.1469 | 7.1860 | 10.3860 | 83.6 |
| 3.6 | 3.6 | 81.6125 | 9.0740 | 12.6740 | 86.0 |
| 4 | 4 | 84.7367 | 11.3237 | 15.3237 | 87.6 |
| 5 | 5 | 89.1832 | 19.6117 | 24.6117 | 90.1 |
| 6 | 6 | 91.2729 | 39.5415 | 45.5415 | 91.5 |
| 7 | 7 | 92.3603 | — | — | — |
| 8 | 8 | 92.9754 | — | — | — |
| 10 | 10 | 93.5845 | — | — | — |
| 12 | 12 | 93.8519 | — | — | — |
| 14 | 14 | 93.9866 | — | — | — |
| 16 | 16 | 94.0615 | — | — | — |

Calculation formulas: ① NX: $Y=(4.3188-94.209)/(1+(X/1.9981)^{3.0815})+94.209$; ② TX: $Y=(0.8779-92.1626)/\{1+(X/2.8494)^{1.7569}\}+92.1626$.

Descriptions on numerical calculation in each column: data in (5) column are calculated with the formula ①; (7) column: data in (1) column are calculated with the formula ①; (8) column: data in (7) column are calculated with the formula ②; (9) column: (2) column+(8) column; (10) column: data in (9) column are calculated with the formula ②; "—" indicates to be beyond the dose-effect range of the TX.

Step 3, a dose-effect curve is reconstructed and a curve equation is fitted.

Figure 5:
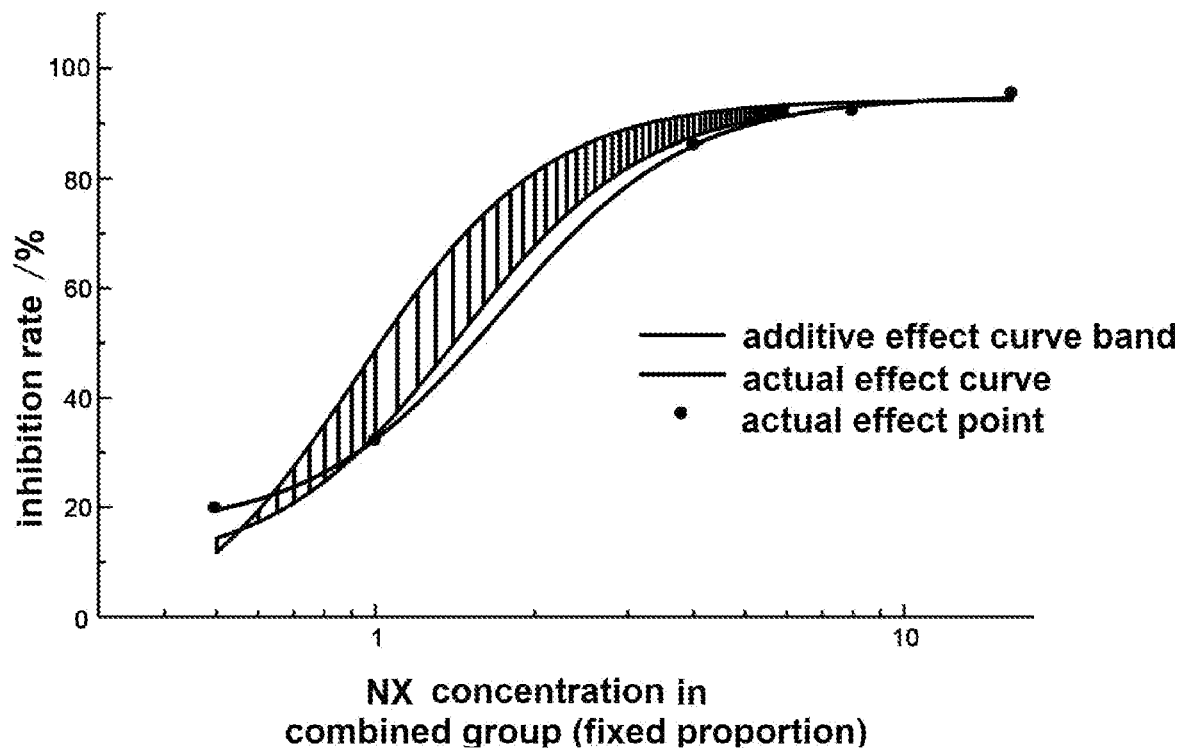
FIG. 5 illustrates a dose-effect curve band and an actual dose-effect relationship curve of an expected additive effect formed by increasing specific combined dose points of multiple NX+TX combinations and then drawing with each dose level of an NX of a combined group as a horizontal coordinate and each expected additive effect value and actual effect value as vertical coordinates when the NX+TX are combined at the fixed proportion in the FIG. 4.

A dose-effect curve band of an expected equivalent additive effect is formed by drawing a diagram with each dose level of the NX in the combined group as a horizontal coordinate and each expected additive effect value and fitted actual effect values [(6) column, (10) column] as a vertical coordinate. And meanwhile, an actual dose-effect curve of an equation ③ NX+TX: $Y=(15.8595-94.9017)/\{1+(X/1.7190)^{2.4490}\}+94.9017$ is drawn on the diagram, as shown in FIG. 5.

Dose-effect equation fitting is performed on the dose of the NX in the combined group and on the expected additive effect value with the NX as the target drug, and the dose-effect equation fitting is also performed on the dose of the NX in the combined group and on the expected additive effect value with the TX as the target drug, such that two equivalent dose-effect curves enclosed into the dose-effect curve band of the expected additive effect is obtained. The equation of each of the equivalent dose-effect curves is as follows:

With the NX as the target drug: $Y_{NX}=(-6.572-94.33)/\{1+(X/0.9231)^{2.452}\}+94.33$;

With the TX as the target drug: $Y_{TX}=(8.534-93.93)/\{1+(X/1.439)^{2.478}\}+93.93$.

Step 4, a positional relationship between the dose-effect curve band and the actual dose-effect curve of the expected additive effect of the combined group is compared and relevant indexes are calculated.

[1] Visual result: it may be observed from the FIG. 5 that the synergistic effect is presented when the combined dose point 0.5+0.5 (μg/ml+ng/ml) is located above the dose-effect curve band; the antagonistic effect is presented when the combined dose points 1+1, 2+2, 4+4 (μg/ml+ng/ml) are located below the dose-effect curve band; the combined dose points 8+8, 16+16 (μg/ml+ng/ml) are beyond a range of the expected additive effect curve with the TX as the target; after the combined dose point 6+6 (μg/ml+ng/ml), the dose-effect relationship of the expected additive effect only is the expected additive effect curve with the NX as the target; the combined dose point 8+8 (μg/ml+ng/ml) is antagonistic and that 16+16 (μg/ml+ng/ml) is synergistic.

[2] Dose ranges of the synergistic, additive and antagonistic effects are calculated.

Equation sets are solved respectively with the above two equations and the dose-effect equation of the actual effect.

$Y=(-6.572-94.33)/\{1+(X/0.9231)^{2.452}\}+94.33$ $Y=(15.8595-94.9017)/\{1+(X/1.7190)^{2.4490}\}+94.9017$    Equation set 1:

$Y=(8.53493.93)/\{1+(X/1.439)^{2.478}\}+93.93$ $Y=(15.8595-94.9017)/\{1+(X/1.7190)^{2.4490}\}+94.9017$    Equation set 2:

The equation set 1 is solved to obtain: X1=0.6344, Y1=22.1901, X2=11.2124, Y2=94.1093;

The equation set 2 is solved to obtain: X=0.9359, Y=30.4090.

The NX dose limits of the additive effect are 0.6344 and 0.9359 μg/ml. According to the combined relationship (1:1) between the NX and the TX, it is very easily to obtain the dose range of the additive effect of the TX. The NX and the TX are within a common effect range.

Dose range of the synergistic effect (NX+TX): [0.5+0.5, 0.6344+0.6344)μg/ml+ng/ml;

Dose range of the additive effect (NX+TX): [0.6344+0.6344, 0.9359+0.9359]μg/ml+ng/ml;

Dose range of the antagonistic effect (NX+TX): (0.9359+0.9359, 6+6)μg/ml+ng/ml.

In the actual dose-effect curve of the combined group, the range belonging to the additive effect: 22.1901%-30.4090%.

Beyond the common effect range of the NX and the TX, there further has an additive effect point (NX+TX: 11.2124+11.2124, μg/ml+ng/m). It may be seen that the combined dose point 8+8 (μg/ml+ng/ml) is below the point and is antagonistic and the combined dose point 16+16 (μg/ml+ng/ml) is above the point and is synergistic.

[3] $CI_d$S are calculated.

It may be seen from the table 5 and the table 6 that the expected additive effect values of the dose point 0.5+0.5 (μg/ml+ng/ml) respectively are 11.5 and 14.2 and the actual observed value is 19.7 (table 4). The $CI_{d1}$ is 19.7/14.2=1.3873>1 and the $CI_{d2}$ is 19.7/11.5=1.7130>1, being synergistic. The expected additive effect values of the dose point 1+1 (μg/ml+ng/ml) respectively are 48.7 and 33.2 and the actual observed value is 23.8. The $CI_{d1}$ is 23.8/48.7=0.4887<1 and the $CI_{d2}$ is 23.8/33.2=0.7168<1, being antagonistic. Similarly, the dose points 2+2 (μg/ml+ng/ml) an 4+4 (μg/ml+ng/ml) can be calculated; both the $CI_{d1}$ and the $CI_{d2}$ are less than 1, being antagonistic. The calculation of the $CI_d$s at the dose points 8+8 (μg/ml+ng/ml) and 16+16 (μg/ml+ng/ml) is ignored.

[4] $CI_e$s are calculated.

Figure 6:
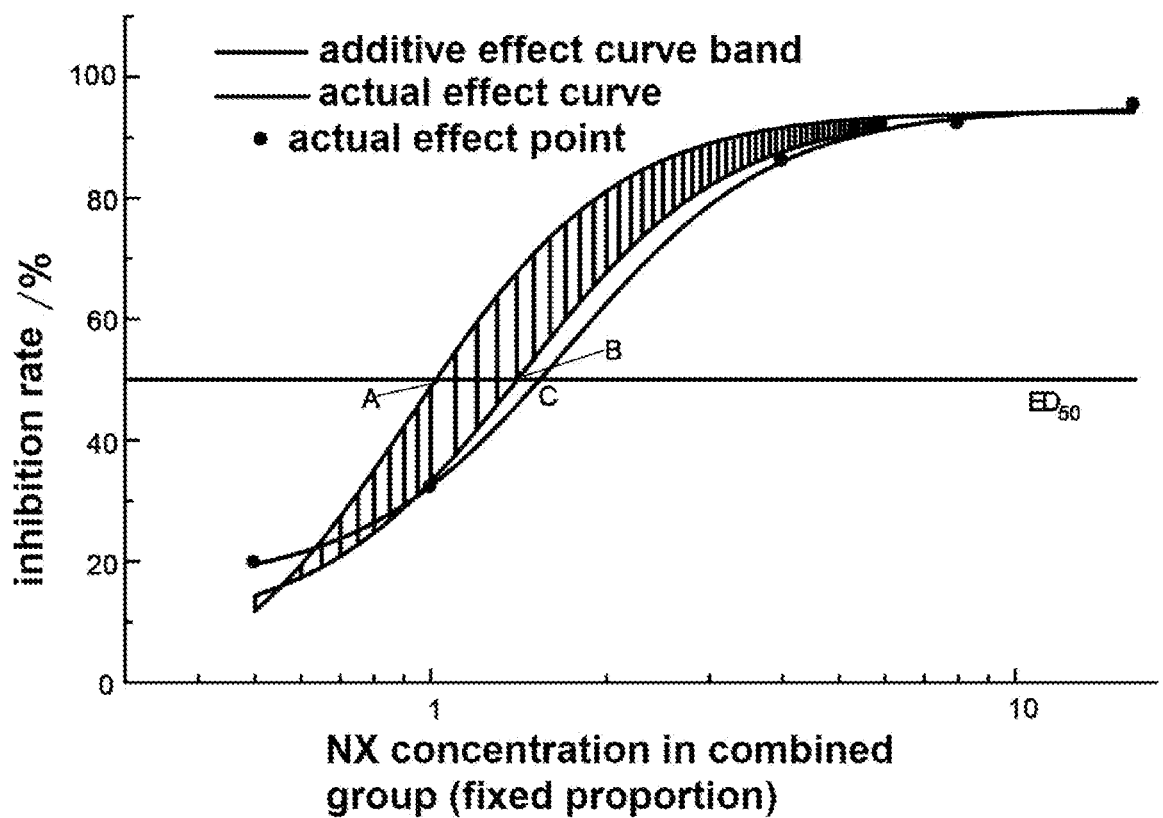
FIG. 6 illustrates that crossed dose points of an $ED_{50}$ efficacy horizontal line with an expected additive effect are A and B, a crossed dose point with an actual effect is C, and crossed dose points of the actual effect are greater than dose range points of the expected additive effect and are located below a dose-effect curve band in the FIG. 5.

Any efficacy level such as $ED_{50}$ can be selected, or the efficacy level is selected as needed. At a place with the vertical coordinate 50 on the diagram of the dose-effect relationship curve of the combined group, a straight line parallel to a horizontal axis is drawn and is respectively intersected with the equivalent dose-effect curve band and the actual dose-effect curve at A, B and C points as shown in FIG. 6 to respectively obtain horizontal coordinate points 1.0196, 1.4059 and 1.5370. At the efficacy $ED_{50}$, the dose range points (NX+TX) of the expected additive effect are 1.0196+1.0196 (μg/ml+ng/ml) and 1.4059+1.4059 (μg/ml+ng/ml), and the dose point (NX+TX) of the actual effect is 1.5370+1.5370 (μg/ml+ng/ml), all of which are located below the dose-effect curve band.

$CI_{e1}$ and $CI_{e2}$ are calculated, $CI_{e1}$=1.5370/1.4059=1.0932>1, $CI_{e2}$=1.5370/1.0196=1.5074>1, indicating to be antagonistic.

Part 2: calculation of two drugs of TX at fixed dose (2 ng/ml) and NX at different concentrations in combined use Step 1: a dose-effect relationship table of dose levels of each single drug and each member in a combined group is prepared, and a respective dose-effect relationship curve equation is fitted.

For dose-effect relationship data among the NX, the TX and the single drug, and dose-effect relationship data of the TX at a fixed concentration (2 ng/ml)+the NX at different concentrations in the combined use, see a table 1.

Dose-effect curve diagrams for the NX and the TX in the single use and for the NX in the combined group are drawn, as shown in FIG. 3A, FIG. 3B and FIG. 3D. A dose-effect relationship equation of each diagram is respectively fitted as follows using a logistic program:

$Y=(4.3188-94.209)/\{1+(X/1.9981)^{3.0815}\}+94.209$    Single-use drug NX:

$Y=(0.8779-92.1626)/\{1+(X/2.8494)^{1.7569}\}+92.1626$    Single-use drug TX:

In the combined group with a TX fixed concentration, NX: $Y=(7.294-94.22)/\{1+(X/1.569^{3.1080}\}+94.22$ Step 2: the dose is converted sequentially, and each dose-effect relationship data formed into an expected additive efficacy curve band under a combined condition is calculated.

Accurate calculation method: under the fixed dose (2 ng/ml) of the TX, after the equivalent dose conversion is performed sequentially, dose values are combined. In order to improve the fitting precision of the expected additive effect curve band, several intermediate dose values are inserted between each of the combined doses. For data in the group, 4 inserted values are arranged between each of the doses at intervals. For example, between 0.5+0.5 and 1+1, there increases 0.6+0.6, 0.7+0.7, 0.8+0.8, 0.9+0.9 and the like.

Step 1, with the NX as the target drug, after equivalent dose conversion is performed on the TX, equivalent doses are combined and an expected additive effect value is calculated using a dose-effect curve equation of the single-use NX. See data in (3), (4), (5) and (6) columns in a table 7.

TABLE 7 calculation table of expected additive effect after the NX and the TX are combined at the fixed proportion and the equivalent dose conversion is performed sequentially with the NX as the target drug

| Doses in combined group | | Equivalent dose conversion with the NX as the target drug (TX→NX, NX + $NX_{tx}$) | | | |
|---|---|---|---|---|---|
| | | | Equivalent dose | | |
| NX (μg/ml) (1) | TX (ng/ml) (2) | Efficacy of TX (%) (3) | Equivalent dose of NX ($NX_{tx}$, μg/ml) (4) | combination of NX (NX + $NX_{tx}$, μg/ml) (5) | NX + $NX_{tx}$ expected additive effect (%) (6) |
| 0.5 | 2 | 32.7687 | 1.5564 | 2.0564 | 51.3 |
| 0.6 | 2 | 32.7687 | 1.5564 | 2.1564 | 54.5 |
| 0.7 | 2 | 32.7687 | 1.5564 | 2.2564 | 57.6 |
| 0.8 | 2 | 32.7687 | 1.5564 | 2.3564 | 60.4 |
| 0.9 | 2 | 32.7687 | 1.5564 | 2.4564 | 63.1 |

TABLE 7-continued calculation table of expected additive effect after the NX and the TX are combined at the fixed proportion and the equivalent dose conversion is performed sequentially with the NX as the target drug

| Doses in combined group | | Equivalent dose conversion with the NX as the target drug (TX→NX, NX + NX$_{tx}$) | | | |
|---|---|---|---|---|---|
| | | | Equivalent dose | | |
| NX (μg/ml) (1) | TX (ng/ml) (2) | Efficacy of TX (%) (3) | Equivalent dose of NX (NX$_{tx}$, μg/ml) (4) | combination of NX (NX + NX$_{tx}$, μg/ml) (5) | NX + NX$_{tx}$ expected additive effect (%) (6) |
| 1 | 2 | 32.7687 | 1.5564 | 2.5564 | 65.6 |
| 1.2 | 2 | 32.7687 | 1.5564 | 2.7564 | 69.9 |
| 1.4 | 2 | 32.7687 | 1.5564 | 2.9564 | 73.5 |
| 1.6 | 2 | 32.7687 | 1.5564 | 3.1564 | 76.6 |
| 1.8 | 2 | 32.7687 | 1.5564 | 3.3564 | 79.1 |
| 2 | 2 | 32.7687 | 1.5564 | 3.5564 | 81.2 |
| 2.4 | 2 | 32.7687 | 1.5564 | 3.9564 | 84.4 |
| 2.8 | 2 | 32.7687 | 1.5564 | 4.3564 | 86.7 |
| 3.2 | 2 | 32.7687 | 1.5564 | 4.7564 | 88.4 |
| 3.6 | 2 | 32.7687 | 1.5564 | 5.1564 | 89.6 |
| 4 | 2 | 32.7687 | 1.5564 | 5.5564 | 90.5 |
| 5 | 2 | 32.7687 | 1.5564 | 6.5564 | 92.0 |
| 6 | 2 | 32.7687 | 1.5564 | 7.5564 | 92.7 |
| 7 | 2 | 32.7687 | 1.5564 | 8.5564 | 93.2 |
| 8 | 2 | 32.7687 | 1.5564 | 9.5564 | 93.5 |
| 10 | 2 | 32.7687 | 1.5564 | 11.5564 | 93.8 |
| 12 | 2 | 32.7687 | 1.5564 | 13.5564 | 94.0 |
| 14 | 2 | 32.7687 | 1.5564 | 15.5564 | 94.0 |
| 16 | 2 | 32.7687 | 1.5564 | 17.5564 | 94.1 |

Calculation formulas: ① NX: $Y=(4.3188-94.209)/\{(1+(X/1.9981)^{3.0815}\}+94.209$; ② TX: $Y=(0.8779-92.1626)/\{1+(X/2.8494)^{1.7569}\}+92.1626$. Descriptions on numerical calculation in each column: (3) column: data in (2) column are calculated with the formula ②; (4) column: data in (1) column are calculated with the formula ①; (5) column: (1) column+(4) column; (6) column: data in (5) column are calculated with the formula ①.

Step 2, with the TX as the target drug, after equivalent dose conversion is performed on the NX, equivalent doses are combined and an expected additive effect value is calculated using a dose-effect curve equation of the single-use TX. See data in (7), (8), (9) and (10) columns in a table 8.

TABLE 8 calculation table of expected additive effect after the TX (at fixed concentration) and the NX are combined at different proportions and the equivalent dose conversion is performed sequentially with the TX as a target drug

| Doses in combined group | | Equivalent dose conversion with the TX as the target drug (NX→TX, TX + TX$_{nx}$) | | | |
|---|---|---|---|---|---|
| | | | Equivalent dose | | |
| NX (μg/ml) (1) | TX (ng/ml) (2) | Efficacy of NX (%) (7) | Equivalent dose of TX (TX$_{nx}$, ng/ml) (8) | combination of TX (TX + TX$_{nx}$, ng/ml) (9) | TX + TX$_{nx}$ expected additive effect (%) (10) |
| 0.5 | 2 | 5.5596 | 0.5414 | 2.5414 | 41.9 |
| 0.6 | 2 | 6.4726 | 0.6028 | 2.6028 | 42.9 |
| 0.7 | 2 | 7.7324 | 0.6824 | 2.6824 | 44.1 |
| 0.8 | 2 | 9.3724 | 0.7797 | 2.7797 | 45.5 |
| 0.9 | 2 | 11.4093 | 0.8937 | 2.8937 | 47.1 |
| 1 | 2 | 13.8409 | 1.0236 | 3.0236 | 48.9 |
| 1.2 | 2 | 19.7842 | 1.3271 | 3.3271 | 52.7 |
| 1.4 | 2 | 26.8326 | 1.6849 | 3.6849 | 56.7 |
| 1.6 | 2 | 34.4514 | 2.0934 | 4.0934 | 60.6 |
| 1.8 | 2 | 42.0953 | 2.5508 | 4.5508 | 64.3 |
| 2 | 2 | 49.3297 | 3.0565 | 5.0565 | 67.8 |
| 2.4 | 2 | 61.6284 | 4.2151 | 6.2151 | 73.7 |
| 2.8 | 2 | 70.7302 | 5.5822 | 7.5822 | 78.3 |
| 3.2 | 2 | 77.1469 | 7.1860 | 9.1860 | 81.8 |
| 3.6 | 2 | 81.6125 | 9.0740 | 11.0740 | 84.5 |
| 4 | 2 | 84.7367 | 11.3237 | 13.3237 | 86.5 |
| 5 | 2 | 89.1832 | 19.6117 | 21.6117 | 89.6 |
| 6 | 2 | 91.2729 | 39.5415 | 41.5415 | 91.3 |
| 7 | 2 | 92.3603 | — | — | — |

TABLE 8-continued calculation table of expected additive effect after the TX (at fixed
concentration) and the NX are combined at different proportions and the equivalent
dose conversion is performed sequentially with the TX as a target drug

| Doses in combined group | | | Equivalent dose conversion with the TX as the target drug (NX→TX, TX + TX$_{nx}$) | | |
|---|---|---|---|---|---|
| | | | | Equivalent dose | |
| NX (µg/ml) (1) | TX (ng/ml) (2) | Efficacy of NX (%) (7) | Equivalent dose of TX (TX$_{nx}$, ng/ml) (8) | combination of TX (TX + TX$_{nx}$, ng/ml) (9) | TX + TX$_{nx}$ expected additive effect (%) (10) |
| 8  | 2 | 92.9754 | — | — | — |
| 10 | 2 | 93.5845 | — | — | — |
| 12 | 2 | 93.8519 | — | — | — |
| 14 | 2 | 93.9866 | — | — | — |
| 16 | 2 | 94.0615 | — | — | — |

Calculation formulas: ① NX: $Y=(4.3188-94.209)/\{1+(X/1.9981)^{-3.0815}\}+94.209$; ② TX: $Y=(0.8779-92.1626)/\{1+(X/2.8494)^{1.7569}\}+92.1626$. Descriptions on numerical calculation in each column: data in (5) column are calculated with the formula ①; (7) column: data in (1) column are calculated with the formula ①; (8) column: data in (7) column are calculated with the formula ②; (9) column: (2) column+(8) column; (10) column: data in (9) column are calculated with the formula ②; "-" indicates to be beyond the dose-effect range of the TX.

Step 3, a dose-effect curve is reconstructed and a curve equation is fitted.

Figure 7:
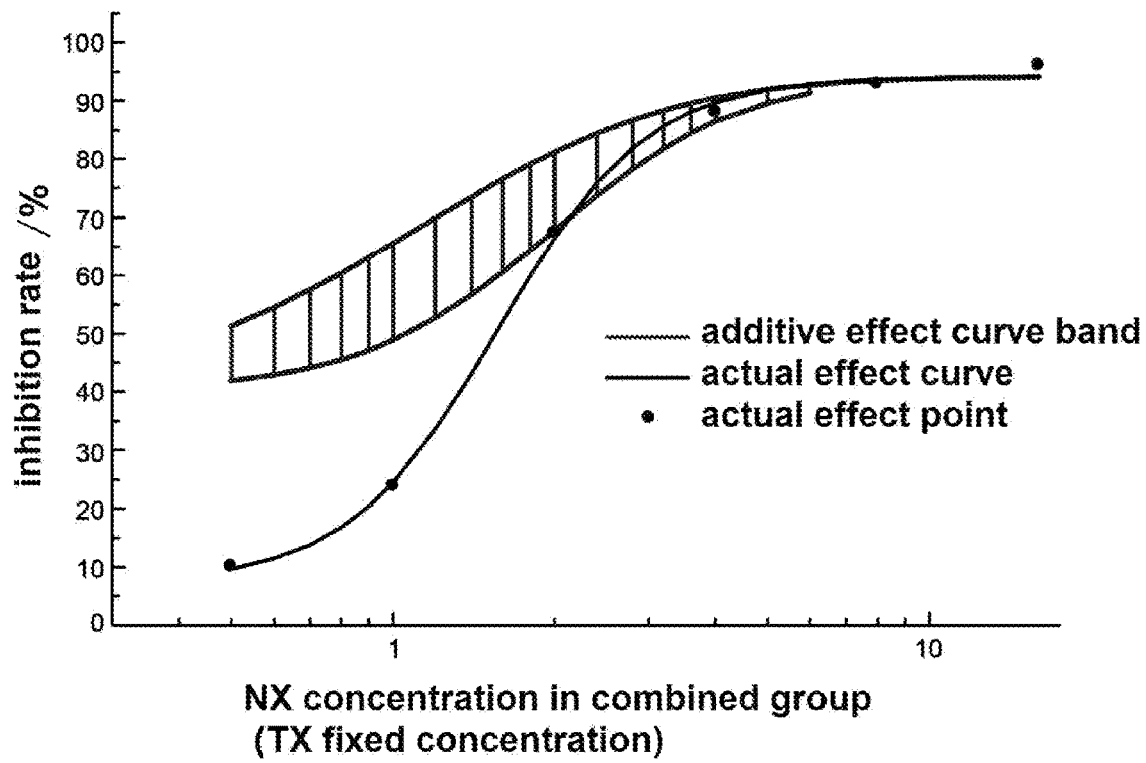
FIG. 7 illustrates a dose-effect curve band diagram and an actual dose-effect relationship curve formed by drawing with each dose level of an NX of a combined group as a horizontal coordinate and each expected additive effect value as a vertical coordinate when the TX at a fixed concentration and +NX at different proportions are combined in the first embodiment of the present disclosure.

A dose-effect curve band, as shown in FIG. 7, of an expected equivalent additive effect is formed by drawing a diagram with each dose level of the NX in the combined group as a horizontal coordinate and each expected additive effect value and fitted actual effect values [(6) column, (10) column] as a vertical coordinate. And meanwhile, an actual dose-effect curve of an equation ③ NX+TX (fixed): $Y=(7.294-94.22)/\{1+(X/1.569^{\wedge}3.1080\}+94.22$ is drawn on the diagram.

Dose-effect equation fitting is performed on the dose of the NX in the combined group and on the expected additive effect value with the NX as the target drug, and the dose-effect equation fitting is also performed on the dose of the NX in the combined group and on the expected additive effect value with the TX as the target drug, such that two equivalent dose-effect curves enclosed into the dose-effect curve band of the expected additive effect is obtained. The equation of each of the curves is as follows:

$Y_{NX}=(42.46-94.7)/\{(1+(X/1.136)^{\wedge}1.892\}+94.7$;   With the NX as the target drug:

$Y_{TX}=(39.95-94.91)/\{1+(X/1.976)^{\wedge}2.41)\}+94.91$.   With the TX as the target drug:

Step 4, a positional relationship between the dose-effect curve band and the actual dose-effect curve of the expected additive effect of the combined group is compared and relevant indexes are calculated.

[1] Visual result: it may be observed from the FIG. 7 that the antagonistic effect is presented when the combined dose points 0.5+2, 1+2 and 2+2 (µg/ml+ng/ml) are located below the dose-effect curve band; the additive effect is presented when the combined dose point 4+2 (µg/ml+ng/ml) is located within the dose-effect curve band; the combined dose point 8+2 (µg/ml+ng/ml) is on the line; the synergistic effect is presented when 16+2 (µg/ml+ng/ml) is located above the rang of the dose-effect curve band.

[2] Dose ranges of the synergistic, additive and antagonistic effects are calculated It may be seen from the FIG. 7 that there is an obvious intersection below a dose-effect curve and a dose-effect curve band of the actual effect and also seemingly has an intersection with the curve above. Therefore, two equation sets need to be solved.

$Y_{NX}=(42.46-94.7)/\{(1+(X/1.136)^{\wedge}1.892\}+94.7$ $Y=(7.294-94.22)/\{1+(X/1.569)^{\wedge}3.1080\}+94.22$   Equation set 1:

$Y_{TX}=(39.95-94.91)/\{1+(X/1.976)^{\wedge}2.41\}+94.91$ $Y=(7.294-94.22)/\{1+(X/1.569)^{\wedge}3.1080\}+94.22$   Equation set 2:

The equation set 1 is solved to obtain: X=4.5777; Y=91.2101;

The equation set 2 is solved to obtain: X=2.1229 Y=69.7986.

The NX dose limits of the additive effect are 2.1229–4.5777 µg/ml. According to the combined relationship (fixed dose: 2 ng/ml) between the NX and the TX, it is very easily to obtain the dose range of the additive effect of the TX. The NX and the TX are within a common effect range.

Dose range of the synergistic effect (NX+TX): [0.5+2, 2.1229+2)µg/ml+ng/ml;

Dose range of the additive effect (NX+TX): [2.1229+2, 4.5777+2] µg/ml+ng/ml;

Dose range of the antagonistic effect (NX+TX): (4.5777+2, 6+2] µg/ml+ng/ml.

In the actual dose-effect curve of the combined group, the range belonging to the additive effect is 69.7986%–91.2101%.

For the combined dose points beyond the common effect range, the expected additive effect value of the combined dose point 8+2 (µg/ml+ng/ml) follows $Y_{NX}=(42.46-94.7)/\{1+(X/1.136)^{\wedge}1.892\}+94.7$; by substituting X=8, 93.431 is obtained. However, the actual observed value is 92.9, being antagonistic; the expected additive effect value of the combined dose point 16+2 (µg/ml+ng/ml) is 94.1563 and the actual observed value is 96.1, being synergistic.

[3] $CI_d$s and $CI_e$s are calculated; the specific calculation method has been described above and thus is ignored here.

Embodiment 2: An Efficacy Detection Method of Three Drugs in Combined Use

Title: there are many application schemes for a chemotherapeutic drug in lung cancer treatment. The chemotherapeutic drug in these schemes mainly includes the followings that belong to a topoisomerase inhibitor, a microtubule inhibitor, a metabolic inhibitor and an alkylating agent from types. One representative drug is successively selected from the four types of the drugs and respectively is etoposide (A), vincristine (B), 5-fluorouracil (C) and adriamycin (D). For any three combined application schemes, the inhibition effect to growth of human lung cancer cell H460 lines is detected with an MTT method. The three schemes successively are combinations of four combined drugs of A+B+C, A+B+D, A+C+D and B+C+D and the synergistic, additive and antagonistic effects are evaluated quantitatively.

$A:B:C$=12.5:2:45 (µg/ml+µg/ml+µg/ml)      A+B+C combination:

$A:B:D$=12.5:2:4 (µg/ml+µg/ml+µg/ml)       A+B+D combination:

$A:C:D$=12.5:45:4 (µg/ml+µg/ml+µg/ml)      A+C+D combination:

$B:C:D$=2:45:4 (µg/ml+µg/ml+µg/ml)         B+C+D combination:

Part 1: calculation of three drugs of etoposide (A), vincristine (B) and 5-fluorouracil (C) in combined use at fixed proportion A:B:C=12.5:2:45 (µg/ml+µg/ml+µg/ml)

Step 1, a dose-effect relationship table of dose levels of each single drug and each member in a combined group is prepared, and a respective dose-effect relationship curve equation is fitted.

Figure 8A:
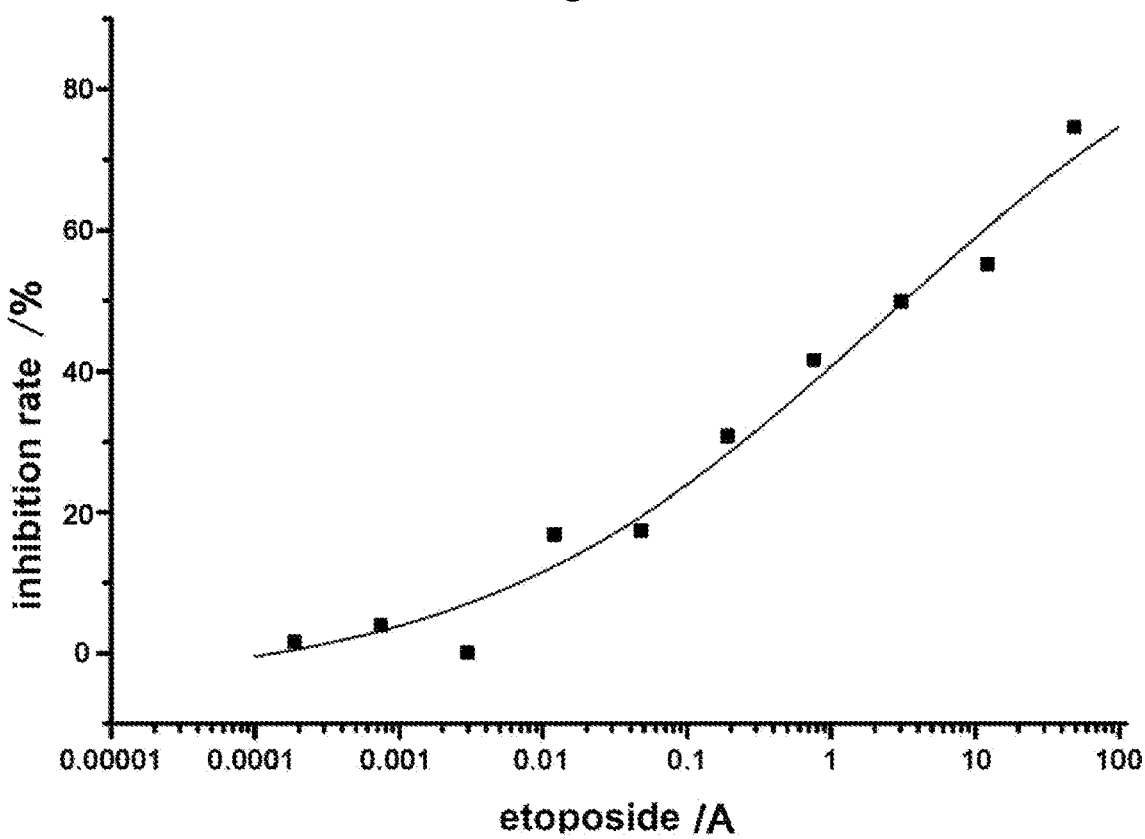
FIG. 8A to FIG. 8D illustrate a dose-effect curve between single drugs of an etoposide (A), a vincristine (B) and a 5-fluorouracil (C) and the etoposide (A) in a drug combined group according to a second embodiment of the present disclosure, wherein FIG. 8A to FIG. 8C respectively illustrate a dose-effect relationship curve among three single drugs of the etoposide (A), the vincristine (B) and the 5-fluorouracil (C)
Figure 8B:
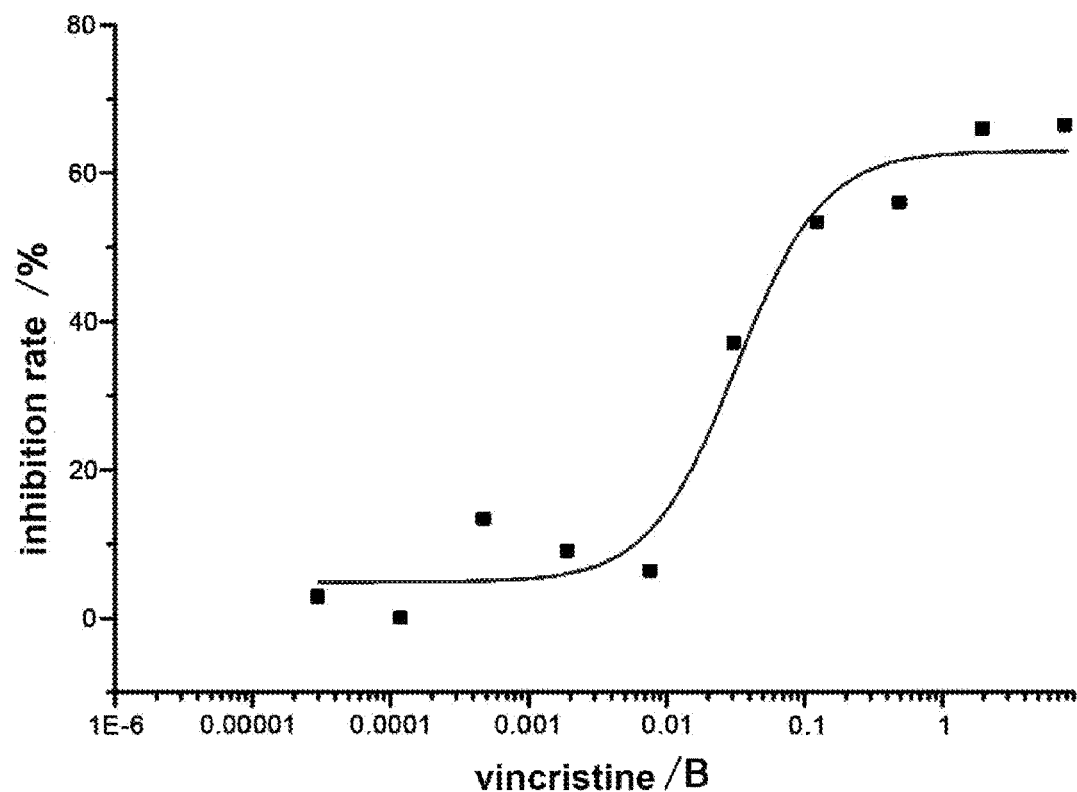
Figure 8C:
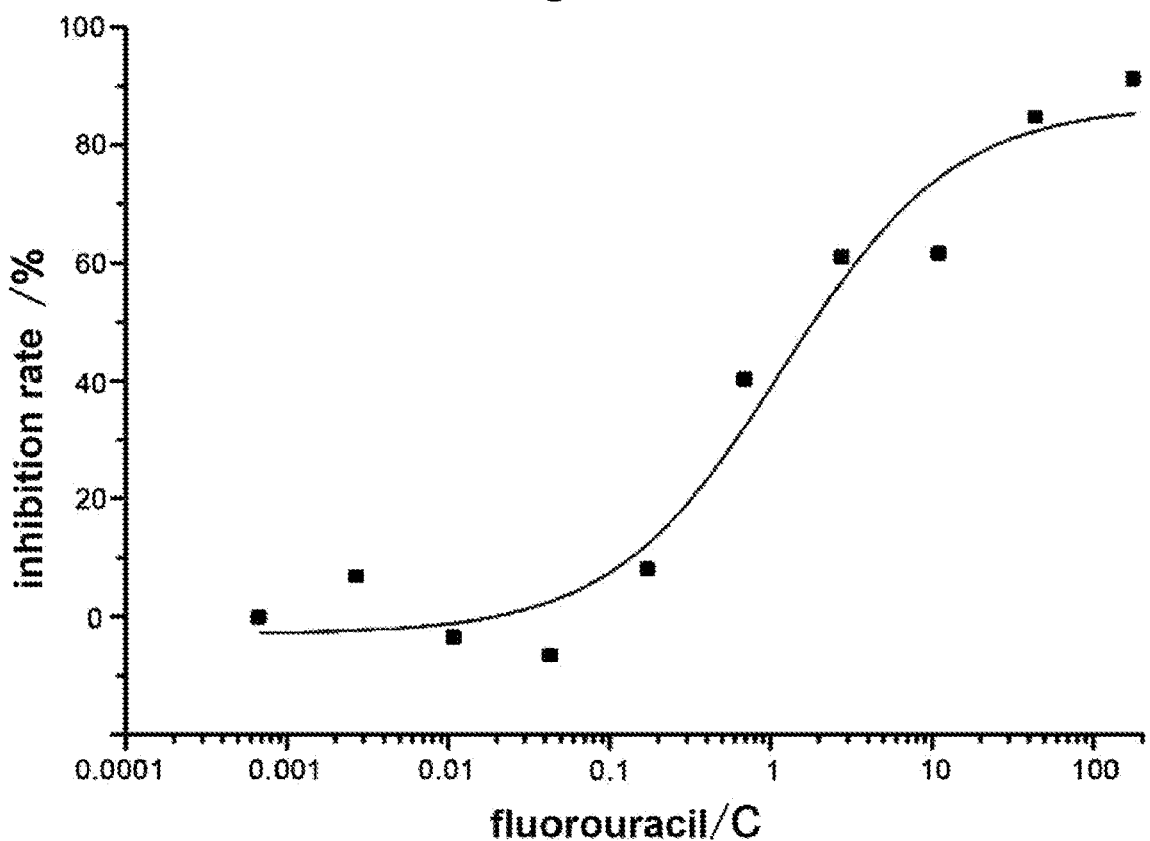
Figure 8D:
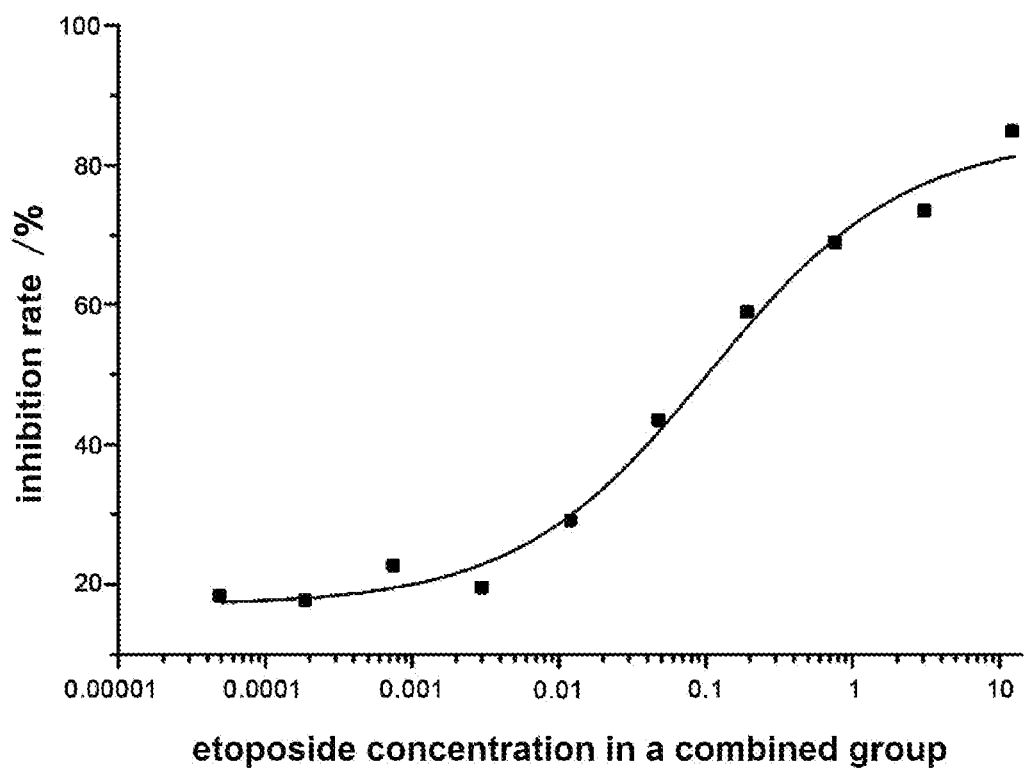

For the etoposide (A), vincristine (B) and 5-fluorouracil (C), dose-effect relationship data of single drugs and dose-effect relationship data in the combined use A:B:C=12.5:2:45 (µg/ml+µg/ml+µg/ml), see a table 9 and a table 10.

are drawn respectively as shown in FIG. 8A, FIG. 8B and FIG. 8C, and an actual dose-effect relationship curve diagram of an expected additive effect in the combined group with a dose change of the etoposide (A) is drawn as shown in FIG. 8D.

Dose-effect relationship equations are respectively fitted using a logistics program and are as follows:

$Y=(-5.003-99.54)/\{1+(X/2.269)^{0.3073}\}+99.54$   Single-use A:

$Y=(4.901-63.00)/\{1+(X/0.03216)^{1.385}\}+63.00$   Single-use B:

$Y=(-2.944-86.77)/\{1+(X/1.182)^{0.8216}\}+86.77$   Single-use C:

In combined use of three drugs: A: $Y=(17.01-84.13)/\{1+(X/0.1083)^{0.6546}\}+84.13$ Step 2, the dose is converted sequentially, and each dose-effect relationship data formed into an expected additive efficacy curve band under a combined condition is calculated.

Under a fixed proportion of the etoposide (A), the vincristine (B) and the 5-fluorouracil (C), after the dose is converted sequentially, dose values are combined.

The equivalent dose conversion is performed on combinations of two drugs of A+B, A+C and B+C sequentially first and then the equivalent dose conversion is performed on (A+B)+C, (A+C)+B and (B+C)+A. An expression for an expected additive effect of the three drugs in the combined use is as follows.

TABLE 9 dose-effect relationship data table of etoposide (A), vincristine (B) and 5-fluorouracil (C) in single use

| Etoposide (A) µg/ml | Inhibition rate (%) | Vincristine (B) µg/ml | Inhibition rate (%) | 5-fluorouracil (C) µg/ml | Inhibition rate (%) |
|---|---|---|---|---|---|
| 0.000190735 | 1.38 | 0.000030518 | 2.75 | 0.000686646 | −0.33 |
| 0.000762939 | 3.73 | 0.00012207 | −0.11 | 0.002746582 | 6.67 |
| 0.003051758 | −0.19 | 0.000488281 | 13.16 | 0.010986328 | −3.78 |
| 0.012207031 | 16.69 | 0.001953125 | 8.91 | 0.043945313 | −6.89 |
| 0.048828125 | 17.21 | 0.0078125 | 6.25 | 0.17578125 | 7.91 |
| 0.1953125 | 30.58 | 0.03125 | 37.00 | 0.703125 | 40.01 |
| 0.78125 | 41.45 | 0.125 | 53.21 | 2.8125 | 60.82 |
| 3.125 | 49.63 | 0.5 | 55.91 | 11.25 | 61.38 |
| 12.5 | 55.04 | 2 | 65.82 | 45 | 84.48 |
| 50 | 74.37 | 8 | 66.35 | 180 | 90.98 |

TABLE 10 dose-effect relationship data table of three drugs of etoposide (A), vincristine (B) and 5-fluorouracil (C) in combined use

| Etoposide (A) µg/ml | Vincristine (B) µg/ml | 5-fluorouracil (C) µg/ml | Inhibition rate (%) |
|---|---|---|---|
| 0.00004768 | 0.00000763 | 0.00017166 | 18.13 |
| 0.00019073 | 0.00003052 | 0.00068665 | 17.49 |
| 0.00076294 | 0.00012207 | 0.00274658 | 22.52 |
| 0.00305176 | 0.00048828 | 0.01098633 | 19.37 |
| 0.01220703 | 0.00195313 | 0.04394531 | 28.97 |
| 0.048828125 | 0.0078125 | 0.17578125 | 43.27 |
| 0.1953125 | 0.03125 | 0.703125 | 58.71 |
| 0.78125 | 0.125 | 2.8125 | 68.82 |
| 3.125 | 0.5 | 11.25 | 73.34 |
| 12.5 | 2 | 45 | 84.67 |

Dose-effect curve diagrams of three single drugs of the etoposide (A), the vincristine (B) and the 5-fluorouracil (C)

$Y_{(A+B+C)}=[Y_{(A+B)C}, Y_{(A+C)+B}, Y_{(B+c)+A}]\ _{Hi}^{Lo}\downarrow$, wherein $_{Hi}^{Lo}\downarrow$ Indicates function values of units in a number set and should be arranged from low to high. The $Y_{(A+B+C)}=[Y_{(A+B)+C}, Y_{(A+C)+B}, Y_{(B+c)+A}]\ _{Hi}^{Lo}\downarrow$ indicates that the expected additive effect value of A, B and C in the combined use is a set in effect values obtained by three combinations of (A+B)+C, (A+C)+B and (B+C)+A from a minimum value to a maximum value.

(1) Equivalent Dose Sequential Conversion of (A+B)+C

Step 1, with the A as the target drug, after equivalent dose conversion is performed on the B to ($A_b$), equivalent doses ($A+A_b$) are combined and an expected additive effect value is calculated using a dose-effect curve equation of the single-use A. See data in (3), (4), (5) and (6) columns in a table 11.

TABLE 11 calculation table of expected additive effect after the etoposide (A) and
the vincristine (B) are combined according to fixed proportion and the equivalent
dose conversion is sequentially performed with the etoposide (A) as the target drug

| Doses in combined use | | | Equivalent dose conversion with the A as the target drug ($B \rightarrow A, A + A_b$) | | |
|---|---|---|---|---|---|
| A (µg/ml) (1) | B (µg/ml) (2) | Efficacy of B (%) (3) | Equivalent dose of A (Ab, µg/ml) (4) | Equivalent dose combination of A (A + Ab, µg/ml) (5) | $B \rightarrow A(A + Ab)$ expected additive effect (%) (6) |
| 0.00004768 | 0.00000763 | 4.9016 | 0.0015 | 0.0015 | 4.9901 |
| 0.00019073 | 0.00003052 | 4.9048 | 0.0015 | 0.0017 | 5.2468 |
| 0.00076294 | 0.00012207 | 4.9268 | 0.0015 | 0.0022 | 6.1365 |
| 0.00305176 | 0.00048828 | 5.0764 | 0.0016 | 0.0046 | 8.5430 |
| 0.01220703 | 0.00195313 | 6.0768 | 0.0022 | 0.0144 | 13.2290 |
| 0.048828125 | 0.0078125 | 12.0757 | 0.0112 | 0.0600 | 20.7849 |
| 0.1953125 | 0.03125 | 33.3731 | 0.3855 | 0.5808 | 36.4808 |
| 0.78125 | 0.125 | 55.3101 | 6.2252 | 7.0065 | 56.2345 |
| 3.125 | 0.5 | 61.7291 | 14.4108 | 17.5358 | 63.1723 |
| 12.5 | 2 | 62.8101 | 16.6877 | 29.1877 | 66.7919 |

Calculation formulas: ① single-use A: $Y=(-5.003-99.54)/\{1+(X/2.269)^{0.3073}\}+99.54$; ② single-use B: $Y=(4.901-63.00)/\{1+(X/0.03216)^{1.385}\}+63.00$. Descriptions on numerical calculation in each column: (3) column: data in (2) column are calculated with the formula ②; (4) column: data in (1) column are calculated with the formula ①; (5) column: (1) column+(4) column; (6) column: data in (5) column are calculated with the formula ①.

Step 2, with the B as the target drug, after equivalent dose conversion is performed on the B into ($B_a$), equivalent doses ($B+B_a$) are combined and an expected additive effect value is calculated using a dose-effect curve equation of the single-use B. See data in (7), (8), (9) and (10) columns in a table 12.

TABLE 12 calculation table of expected additive effect after the etoposide (A) and
the vincristine (B) are combined according to fixed proportion and the equivalent
dose conversion is sequentially performed with the vincristine (B) as the target drug

| Doses in combined use | | | Equivalent dose conversion with the B as the target drug ($A \rightarrow B, B + B_a$) | | |
|---|---|---|---|---|---|
| A (µg/ml) (1) | B (µg/ml) (2) | Efficacy of A (%) (7) | Equivalent dose of B (Ba, µg/ml) (8) | Equivalent dose combination of B (B + Ba, µg/ml) (9) | $A \rightarrow B(B + Ba)$ expected additive effect (%) (10) |
| 0.00004768 | 0.00000763 | −1.3189 | — | — | — |
| 0.00019073 | 0.00003052 | 0.5342 | — | — | — |
| 0.00076294 | 0.00012207 | 3.2432 | — | — | — |
| 0.00305176 | 0.00048828 | 7.1153 | 0.0031 | 0.0036 | 7.5855 |
| 0.01220703 | 0.00195313 | 12.4756 | 0.0082 | 0.0101 | 14.6541 |
| 0.048828125 | 0.0078125 | 19.5765 | 0.0147 | 0.0225 | 26.9134 |
| 0.1953125 | 0.03125 | 28.4535 | 0.0244 | 0.0556 | 44.4769 |
| 0.78125 | 0.125 | 38.7811 | 0.0410 | 0.1660 | 57.5744 |
| 3.125 | 0.5 | 49.8373 | 0.0780 | 0.5780 | 61.9562 |
| 12.5 | 2 | 60.6678 | 0.3182 | 2.3182 | 62.8452 |

Calculation formulas: ① single-use A: $Y=(-5.003-99.54)/\{1+(X/2.269)^{0.3073}\}+99.54$; ② single-use B: $Y=(4.901-63.00)/\{1+(X/0.03216)^{1.385}\}+63.00$. Descriptions on numerical calculation in each column: (7) column: data in (1) column are calculated with the formula ①; (8) column: data in (7) column are calculated with the formula ②; (9) column: (2) column+(8) column; (10) column: data in (9) column are calculated with the formula ②.

Step 3, with $(A+B)=(A+A_b)$ as the target drug, the equivalent dose conversion is performed on the C into ($A_C$), equivalent doses $[(A+A_b)+A_c]$ are combined and an expected additive effect value is calculated using a dose-effect curve equation of the single-use A. See data in (11), (12), (13) and (14) columns in a table 13.

TABLE 13 calculation table of expected additive effect after the etoposide and
vincristine combination (A + B) and the 5-fluorouracil (C) are combined according to
fixed proportion and the equivalent dose conversion is sequentially performed with
the (A + $A_b$) as the target drug Equivalent dose conversion with the (A + B) as the target drug
(C→(A + B), A + $A_b$ + $A_c$)

| Doses in combined use | | | Equivalent dose | | |
|---|---|---|---|---|---|
| A + $A_b$ (μg/ml) (1) | C (μg/ml) (2) | Efficacy of C (%) (11) | Equivalent dose of A ($A_c$, μg/ml) (12) | combination of A (A + $A_b$ + $A_c$, μg/ml) (13) | C→A + $A_b$(A + $A_b$ + $A_c$) expected additive effect (%) (14) |
| 0.0015 | 0.00017166 | −2.8810 | 7.53361E−06 | 0.0015 | 5.0039 |
| 0.0017 | 0.00068665 | −2.7475 | 9.227E−06 | 0.0017 | 5.2625 |
| 0.0022 | 0.00274658 | −2.3331 | 1.6187E−05 | 0.0023 | 6.1585 |
| 0.0046 | 0.01098633 | −1.0631 | 5.98174E−05 | 0.0047 | 8.5897 |
| 0.0144 | 0.04394531 | 2.6806 | 0.00059 | 0.0150 | 13.4169 |
| 0.0600 | 0.17578125 | 12.5608 | 0.0124 | 0.0724 | 21.9265 |
| 0.5808 | 0.703125 | 32.4840 | 0.3420 | 0.9227 | 40.0877 |
| 7.0065 | 2.8125 | 57.2443 | 7.9792 | 14.9857 | 62.0187 |
| 17.5358 | 11.25 | 74.5929 | 98.9702 | 116.5060 | 75.5325 |
| 29.1877 | 45 | 82.4752 | 463.0513 | 492.2390 | 82.7418 |

Calculation formulas: ① combination (A+B)=(A+$A_b$): Y=(−5.003−99.54)/{1+(X/2.269)^0.3073}+99.54. ② single-use C: Y=(−2.944−86.77)/{1+(X/1.182)^0.8216}+86.77. Descriptions on numerical calculation in each column: (11) column: data in (2) column are calculated with the formula ②; (12) column: (11) column is calculated with the formula ①; (13) column: (1) column+(12) column; (14) column: data in (13) column are calculated with the formula ①.

Step 4, with (A+B)=(B+$B_a$) as the target drug, the equivalent dose conversion is performed on the C into ($B_C$), equivalent doses [(B+$B_a$)+$B_C$] are combined and an expected additive effect value is calculated using a dose-effect curve equation of the single-use B. See data in (15), (16), (17) and (18) columns in a table 14.

Calculation formulas: ① combination (A+B)=(B+$B_b$) Y=(4.901−63.00)/{1+(X/0.03216)^0.385}+63.00. ② single-use C: Y=(−2.944−86.77)/{1+(X/1.182)^0.8216}+86.77. Descriptions on numerical calculation in each column: (15) column: data in (2) column are calculated with the formula ②; (16) column: (15) column is calculated with the formula ①; (17) column: (1) column+(16) column; (18) column: data in (17) column are calculated with the formula ①.

Step 5, with the C as the target drug, the equivalent dose conversion is performed on the (A+B)=(A+$A_b$) into ($C_{(A+Ab)}$), equivalent doses [(C+$C_{(A+Ab)}$)] are combined and an expected additive effect value is calculated using a dose-effect curve equation of the single-use C. See data in (19), (20), (21) and (22) columns in a table 15.

TABLE 14 calculation table of expected additive effect after the etoposide and
vincristine combination (A + B) and the 5-fluorouracil (C) are combined according to
fixed proportion and the equivalent dose conversion is sequentially performed with
the (B + $B_a$) as the target drug Equivalent dose conversion with the (A + B) as the target drug
(C→(B + $B_a$), B + $B_a$ + $B_c$)

| Doses in combined use | | | Equivalent dose | | |
|---|---|---|---|---|---|
| B + $B_a$ (μg/ml) (1) | C (μg/ml) (2) | Efficacy of C (%) (15) | Equivalent dose of B ($B_c$, μg/ml) (16) | combination of B (B + $B_a$ + $B_c$, μg/ml) (17) | C→B + $B_a$(B + $B_a$ + $B_c$) expected additive effect (%) (18) |
| — | 0.00017166 | −2.8810 | — | — | — |
| — | 0.00068665 | −2.7475 | — | — | — |
| — | 0.00274658 | −2.3331 | — | — | — |
| 0.0036 | 0.01098633 | −1.0631 | — | — | — |
| 0.0101 | 0.04394531 | 2.6806 | — | — | — |
| 0.0225 | 0.17578125 | 12.5608 | 0.008247 | 0.0308 | 33.0514 |
| 0.0556 | 0.703125 | 32.4840 | 0.029897 | 0.0855 | 51.0850 |
| 0.1660 | 2.8125 | 57.2443 | 0.158330 | 0.3243 | 60.7261 |
| 0.5780 | 11.25 | 74.5929 | — | — | — |
| 2.3182 | 45 | 82.4752 | — | — | — |

TABLE 15 calculation table of expected additive effect after the etoposide and vincristine combination (A + B) and the 5-fluorouracil (C) are combined according to fixed proportion and the equivalent dose conversion is sequentially performed with the C as the target drug Equivalent dose conversion with the (A + B) as the target drug $((A + A_b) \to C, C + C_{(A+Ab)})$

| Doses in combined use | | | Equivalent dose | | |
|---|---|---|---|---|---|
| $A + A_b$ (µg/ml) (1) | C (µg/ml) (2) | Efficacy of $A + A_b$ (%) (19) | Equivalent dose of C $C_{(A+Ab)}$, µg/ml (20) | combination of C $(C + C_{(A+Ab)}$, µg/ml) (21) | $A + A_b \to C(C + C_{(A+Ab)})$ expected additive effect (%) (22) |
| 0.0015 | 0.00017166 | 4.9901 | 0.0691 | 0.0693 | 5.0049 |
| 0.0017 | 0.00068665 | 5.2468 | 0.0721 | 0.0728 | 5.3049 |
| 0.0022 | 0.00274658 | 6.1365 | 0.0828 | 0.0856 | 6.3575 |
| 0.0046 | 0.01098633 | 8.5430 | 0.1144 | 0.1254 | 9.3187 |
| 0.0144 | 0.04394531 | 13.2290 | 0.1871 | 0.2310 | 15.6554 |
| 0.0600 | 0.17578125 | 20.7849 | 0.3404 | 0.5162 | 27.2097 |
| 0.5808 | 0.703125 | 36.4808 | 0.8789 | 1.5821 | 47.2594 |
| 7.0065 | 2.8125 | 56.2345 | 2.6447 | 5.4572 | 66.8964 |
| 17.5358 | 11.25 | 63.1723 | 4.1420 | 15.3920 | 77.0585 |
| 29.1877 | 45 | 66.7919 | 5.4126 | 50.4126 | 82.8411 |

Calculation formulas: ① combination $(A+B)=(A+A_b)$: $Y=(-5.003-99.54)/\{1+(X/2.269)^{0.3073}\}+99.54$. ② single-use C: $Y=(-2.944-86.77)/\{1+(X/1.182)^{0.8216}\}+86.77$. Descriptions on numerical calculation in each column: (19) column: data in (1) column are calculated with the formula ①; (20) column: (19) column is calculated with the formula ②; (21) column: (1) column+(12) column; (22) column: data in (13) column are calculated with the formula ②2.

Step 6, with the C as the target drug, the equivalent dose conversion is performed on the $(A+B)=(B+B_a)$ into $(C_{(B+Ba)})$, equivalent doses $[(C+C_{(B+Ba)})]$ are combined and an expected additive effect value is calculated using a dose-effect curve equation of the single-use C. See data in (23), (24), (25) and (26) columns in a table 16.

TABLE 16 calculation table of expected additive effect after the etoposide and vincristine combination (A + B) and the 5-fluorouracil (C) are combined according to fixed proportion and the equivalent dose conversion is sequentially performed with the C as the target drug Equivalent dose conversion with the (A + B) as the target drug $((B + B_a) \to C, C + C_{(B+Ba)})$

| Doses in combined use | | | Equivalent dose | | |
|---|---|---|---|---|---|
| $B + B_a$ (µg/ml) (1) | C (µg/ml) (2) | Efficacy of $B + B_a$ (%) (23) | Equivalent dose of C $(B_c$, µg/ml) (24) | combination of C $(C + C_{(B+Ba)}$, µg/ml) (25) | $B + B_a \to C(C + C_{(B+Ba)})$ expected additive effect (%) (26) |
| — | 0.00017166 | — | — | — | — |
| — | 0.00068665 | — | — | — | — |
| — | 0.00274658 | — | — | — | — |
| 0.0036 | 0.01098633 | 7.5855 | 0.1014 | 0.1124 | 8.3966 |
| 0.0101 | 0.04394531 | 14.6541 | 0.2123 | 0.2563 | 16.9432 |
| 0.0225 | 0.17578125 | 26.9134 | 0.5070 | 0.6827 | 31.9670 |
| 0.0556 | 0.703125 | 44.4769 | 1.3587 | 2.0618 | 51.9904 |
| 0.1660 | 2.8125 | 57.5744 | 2.8703 | 5.6828 | 67.4066 |
| 0.5780 | 11.25 | 61.9562 | 3.8092 | 15.0592 | 76.9019 |
| 2.3182 | 45 | 62.8452 | 4.0487 | 49.0487 | 82.7556 |

Calculation formulas: ① combination $(A+B)=(B+B_a)$: $Y=(4.901-63.00)/\{1+(X/0.03216)^{1.385}\}+63.00$. ② single-use C: $Y=(-2.944-86.77)/\{1+(X/1.182)^{0.8216}\}+86.77$. Descriptions on numerical calculation in each column: (23) column: data in (1) column are calculated with the formula ①; (24) column: (23) column is calculated with the formula ②; (25) column: (2) column+(12) column; (26) column: data in (25) column are calculated with the formula ②2.

After equivalent dose sequential conversion of (A+B)+C, the expected additive effect values are summarized. That is, the table 11 to the table 16 are summarized as follows in a table 17.

TABLE 17 expected additive effect values of (A + B) + C combination after the equivalent dose sequential conversion

| Doses in three-drug combination (A + B) + C combination (μg/ml) | | | Expected additive effect (%) | | | |
|---|---|---|---|---|---|---|
| A (μg/ml) (1) | B (μg/ml) (2) | C (μg/ml) (2) | C→A + $A_b$ (A + $A_b$ + $A_c$) | C→B + $B_a$ (B + $B_a$ + $B_c$) | A + $A_b$→C (C + $C_{(A+Ab)}$) | B + Ba→C (C + $C_{(B+Ba)}$) |
| 0.00004768 | 0.00000763 | 0.00017166 | 5.0039 | — | 5.0049 | — |
| 0.00019073 | 0.00003052 | 0.00068665 | 5.2625 | — | 5.3049 | — |
| 0.00076294 | 0.00012207 | 0.00274658 | 6.1585 | — | 6.3575 | — |
| 0.00305176 | 0.00048828 | 0.01098633 | 8.5897 | — | 9.3187 | 8.3966 |
| 0.01220703 | 0.00195313 | 0.04394531 | 13.4169 | — | 15.6554 | 16.9432 |
| 0.048828125 | 0.0078125 | 0.17578125 | 21.9265 | 33.0514 | 27.2097 | 31.9670 |
| 0.1953125 | 0.03125 | 0.703125 | 40.0877 | 51.0850 | 47.2594 | 51.9904 |
| 0.78125 | 0.125 | 2.8125 | 62.0187 | 60.7261 | 66.8964 | 67.4066 |
| 3.125 | 0.5 | 11.25 | 75.5325 | — | 77.0585 | 76.9019 |
| 12.5 | 2 | 45 | 82.7418 | — | 82.8411 | 82.7556 |

(2) Equivalent Dose Sequential Conversion of (A+C)+B

Steps are the same as those of the "equivalent dose sequential conversion of (A+B)+C" and are described briefly as follows:

Step 1, with the A as the target drug, after equivalent dose conversion is performed on the C into ($A_c$), equivalent doses (A+$A_c$) are combined and an expected additive effect value is calculated using a dose-effect curve equation of the single-use A.

Step 2, with the C as the target drug, after equivalent dose conversion is performed on the A into ($C_a$), equivalent doses (C+$C_a$) are combined and an expected additive effect value is calculated using a dose-effect curve equation of the single-use C.

Step 3, with (A+C)=(A+$A_c$) as the target drug, after equivalent dose conversion is performed on the B Into ($A_b$), equivalent doses [(A+$A_c$)+$A_b$] are combined and an expected additive effect value is calculated using a dose-effect curve equation of the single-use A.

Step 4, with (A+C)=(C+$C_a$) as the target drug, after equivalent dose conversion is performed on the B into ($C_b$), equivalent doses [(C+$C_a$)+$C_b$] are combined and an expected additive effect value is calculated using a dose-effect curve equation of the single-use C.

Step 5, with the B as the target drug, after equivalent dose conversion is performed on the (A+C)=(A+$A_c$) into ($B_{(A+Ac)}$), equivalent doses [B+$B_{(A+Ac)}$] are combined and an expected additive effect value is calculated using a dose-effect curve equation of the single-use B.

Step 6, with the B as the target drug, after equivalent dose conversion is performed on the (A+C)=(C+$C_a$) into ($B_{(C+Ca)}$), equivalent doses [B+$B_{(C+Ca)}$] are combined and an expected additive effect value is calculated using a dose-effect curve equation of the single-use B.

Each detailed calculations steps are the same as the calculation of the "equivalent dose sequential conversion of (A+B)+C" and will not be described here due to spaces. After equivalent dose sequential conversion of (A+C)+B, the expected additive effect values are summarized as a table 18.

TABLE 18 expected additive effect values of (A + C) + B combination after the equivalent dose sequential conversion

| Doses in three-drug combination (A + C) + B combination (μg/ml) | | | Expected additive effect (%) | | | |
|---|---|---|---|---|---|---|
| A (μg/ml) (1) | B (μg/ml) (2) | C (μg/ml) (2) | B→A + $A_c$ (A + $A_c$ + $A_b$) | B→C + $C_a$ (C + $C_a$ + $C_b$) | A + $A_c$→B (B + $B_{(A+Ac)}$) | C + $C_a$→B (B + $B_{(C+Ca)}$) |
| 0.00004768 | 0.00000763 | 0.00017166 | 5.0039 | 5.6911 | — | — |
| 0.00019073 | 0.00003052 | 0.00068665 | 5.2625 | 6.9057 | — | — |
| 0.00076294 | 0.00012207 | 0.00274658 | 6.1585 | 9.0006 | — | — |
| 0.00305176 | 0.00048828 | 0.01098633 | 8.5897 | 12.5941 | 7.6521 | 8.4420 |
| 0.01220703 | 0.00195313 | 0.04394531 | 13.4169 | 19.0367 | 14.8665 | 17.1170 |
| 0.048828125 | 0.0078125 | 0.17578125 | 21.9265 | 31.2699 | 27.9949 | 32.2828 |
| 0.1953125 | 0.03125 | 0.703125 | 40.0877 | 51.4463 | 47.4828 | 50.6362 |
| 0.78125 | 0.125 | 2.8125 | 62.0187 | 68.6835 | 60.4906 | 62.2013 |
| 3.125 | 0.5 | 11.25 | 75.5325 | 77.6746 | — | — |
| 12.5 | 2 | 45 | 82.7418 | 82.9664 | — | — |

(3) Equivalent Dose Sequential Conversion of (B+C)+A

Steps are the same as those of the "equivalent dose sequential conversion of (A+B)+C" and are described briefly as follows:

Step 1, with the B as the target drug, after equivalent dose conversion is performed on the C into ($B_c$), equivalent doses ($B+B_c$) are combined and an expected additive effect value is calculated using a dose-effect curve equation of the single-use B.

Step 2, with the C as the target drug, after equivalent dose conversion is performed on the B into ($C_b$), equivalent doses ($C+C_b$) are combined and an expected additive effect value is calculated using a dose-effect curve equation of the single-use C.

Step 3, with (B+C)=($B+B_c$) as the target drug, after equivalent dose conversion is performed on the A into ($B_a$), equivalent doses [($B+B_c$)+$B_a$] are combined and an expected additive effect value is calculated using a dose-effect curve equation of the single-use B.

Step 4, with (B+C)=($C+C_b$) as the target drug, after equivalent dose conversion is performed on the A into ($C_a$), equivalent doses [($C+C_b$)+$C_a$] are combined and an expected additive effect value is calculated using a dose-effect curve equation of the single-use C.

Step 5, with the A as the target drug, after equivalent dose conversion is performed on the (B+C)=($B+B_c$) into ($A_{(B+Bc)}$), equivalent doses [$A+A_{(B+Bc)}$] are combined and an expected additive effect value is calculated using a dose-effect curve equation of the single-use A.

Step 6, with the A as the target drug, after equivalent dose conversion is performed on the (B+C)=($C+C_b$) into ($A_{(C+Cb)}$), equivalent doses [$A+A_{(C+Cb)}$] are combined and an expected additive effect value is calculated using a dose-effect curve equation of the single-use A.

Each detailed calculations steps are the same as the calculation of the "equivalent dose sequential conversion of (A+B)+C" and will not be described here due to spaces. After equivalent dose sequential conversion of (B+C)+A, the expected additive effect values are summarized as a table 19.

are shown in the FIG.). The curves at the most outside are enclosed into a boundary of the dose-effect curve band as shown in FIG. 9A.

Figure 9A:
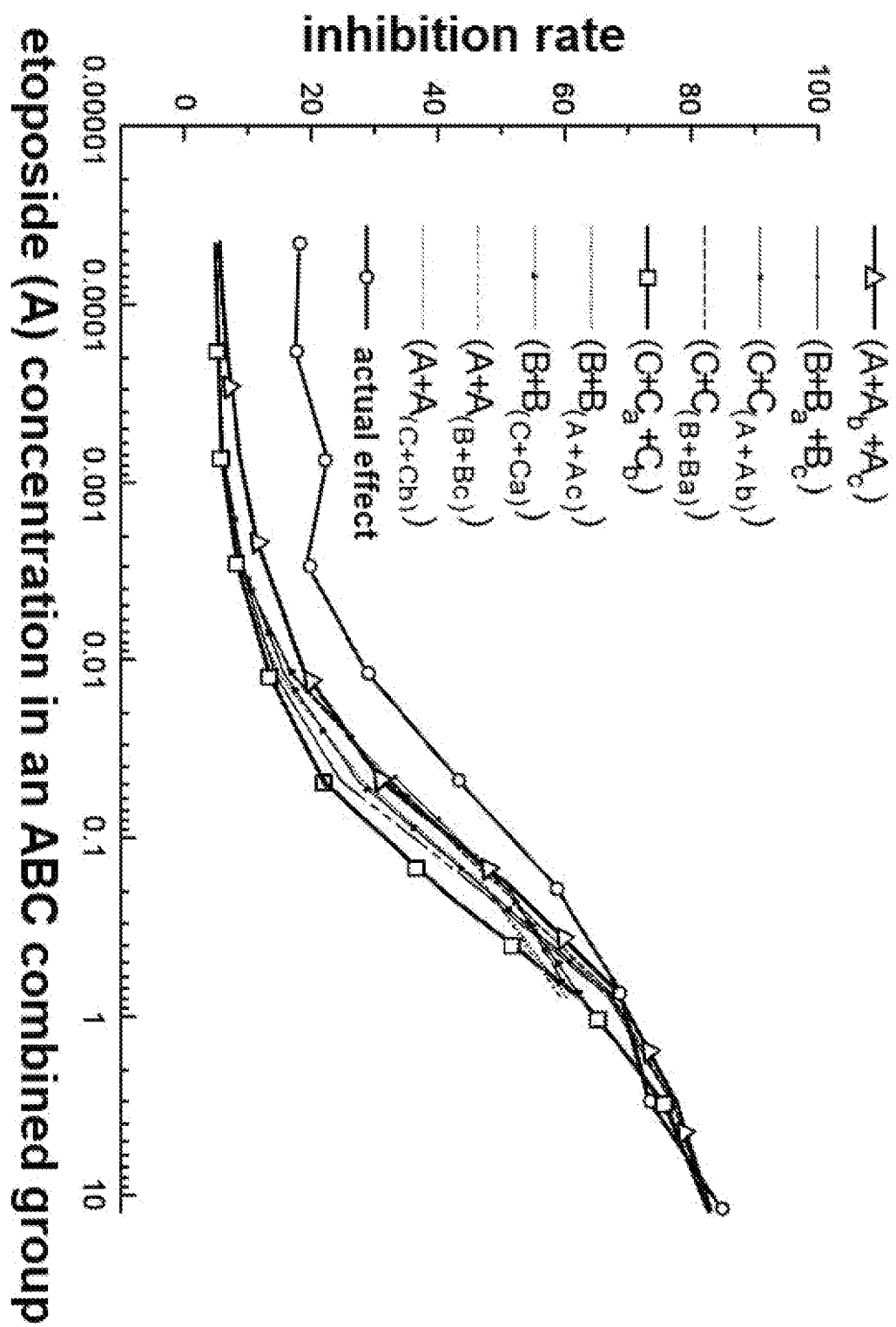
FIG. 9A shows 12 dose-effect curves and actual dose-effect curves drawn with each dose level of an etoposide (A) of a combined group as a horizontal coordinate and data of expected additive effect values and actual effect values in three (A+B)+C, (A+C)+B and (B+C)+A combinations as vertical coordinates.
Figure 9B:
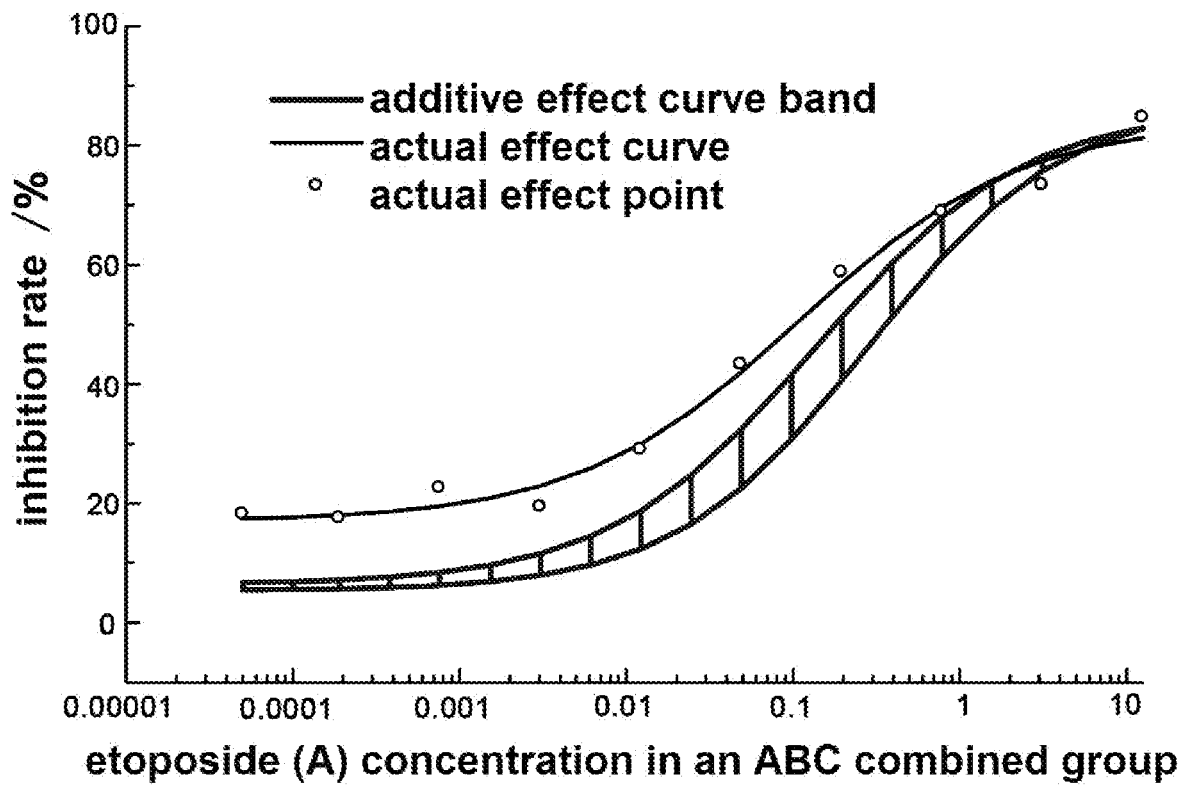
FIG. 9B illustrates a dose-effect curve band enclosed by two curves at the most periphery in 12 dose-effect curves drawn with each dose level of an etoposide (A) of a combined group as a horizontal coordinate and data of expected additive effect values and actual effect values in three (A+B)+C, (A+C)+B and (B+C)+A combinations as vertical coordinates, and an actual dose-effect curve.

It may be seen from the FIG. 9A that the curves at the most outside formed into an equivalent dose-effect curve band are ($A+A_b+A_c$) and ($C+C_a+C_b$). With reference to the positional relationship between the actual effect curve and the equivalent dose-effect curve band, it is considered that an image enclosed by the two curves may basically contain other equivalent dose-effect curves. Therefore, the two curves may be redrawn as shown in FIG. 9B.

By performing fitting on a new constructed dose-effect equation of values at peripheral effect value points formed by a concentration of the etoposide (A) in the combined group and ($A+A_b+A_c$) and ($C+C_a+C_b$) in equivalent lines of the expected additive effect, two curve equations for enclosing into the dose-effect curve band of the expected additive effect are obtained and are respectively as follows:

$$Y_{(A+Ab+Ac)}=(5.34-87.31)/\{1+(X/0.2835)^{0.7528}\}+87.31 \quad Y_{(A+B+C)};$$

$$Y_{(C+Ca+Cb)}=(6.376-86.2)/\{1+(X/0.1374)^{0.7008}\}+86.2 \quad Y_{(A+B+C)};$$

Step 4, positional relationship between the dose-effect curve band and the actual dose-effect curve of the expected additive effect of the combined group is compared and relevant indexes are calculated.

[1] Visual result: it may be observed from the FIG. 9B that the synergistic effect is presented when most combined dose points are located above the dose-effect curve band of the additive effect; a small segment of an upper end of the actual effect curve is intersected with the dose-effect curve band and belongs to doses ranges of the additive and antagonistic effects.

[2] Dose ranges of the synergistic, additive and antagonistic effects are calculated

TABLE 19 expected additive effect values of (B + C) + A combination after the equivalent dose sequential conversion

| Doses in three-drug combination (B + C) + A combination (µg/ml) | | | Expected additive effect (%) | | | |
|---|---|---|---|---|---|---|
| A | B | C | | | | |
| (µg/ml) (1) | (µg/ml) (2) | (µg/ml) (2) | A→B + $B_c$ (B + $B_c$ + $B_a$) | B→C + $C_b$ (C + $C_b$ + $C_a$) | B + $B_c$→A (A + $A_{(B+Bc)}$) | C + $C_b$→A (A + $A_{(C+Cb)}$) |
| 0.00004768 | 0.00000763 | 0.00017166 | — | 5.6911 | — | 5.0046 |
| 0.00019073 | 0.00003052 | 0.00068665 | — | 6.9057 | — | 5.3008 |
| 0.00076294 | 0.00012207 | 0.00274658 | — | 9.0006 | — | 6.3103 |
| 0.00305176 | 0.00048828 | 0.01098633 | — | 12.5941 | — | 8.9768 |
| 0.01220703 | 0.00195313 | 0.04394531 | — | 19.0367 | — | 14.2713 |
| 0.048828125 | 0.0078125 | 0.17578125 | 33.0514 | 31.2699 | 24.6122 | 24.5820 |
| 0.1953125 | 0.03125 | 0.703125 | 51.0850 | 51.4463 | 46.8495 | 46.3858 |
| 0.78125 | 0.125 | 2.8125 | 60.7261 | 68.6835 | 60.7591 | 66.7468 |
| 3.125 | 0.5 | 11.25 | — | 77.6746 | — | 76.9876 |
| 12.5 | 2 | 45 | — | 82.9664 | — | 82.8629 |

Step 3, a dose-effect curve is reconstructed and a curve equation is fitted.

With each dose level of the etoposide (A) of the combined group as a horizontal coordinate and data of expected additive effect values of three (A+B)+C, (A+C)+B and (B+C)+A combinations as a vertical coordinate, 12 dose-effect curves are drawn (three are the same, so nine curves It may be seen from the FIG. 9A and FIG. 9B that there is an obvious intersection between a dose-effect curve and a dose-effect curve band of the actual effect. Therefore, two equation sets need to be solved.

Equation set 1

$$Y_{(A+Ab+Ac)}=(5.34-87.31)/\{1+(X/0.2835)^{0.7528}\}+87.31 \quad Y_{(A+B+C)};$$

In the three-drug combination, A: $Y=(17.01-84.13)/\{1+(X/0.1083)^{\wedge}0.6546\}+84.13$ Equation set 2

$Y_{(C+Ca+Cb)}=(6.376-86.2)/\{1+(X/0.1374)^{\wedge}0.7008\}+86.2$     $Y_{(A+B+C)}$:

In the three-drug combination, A: $Y=(17.01-84.13)/\{1+(X/0.1083)^{\wedge}0.6546\}+84.13$ The equation set 1 is solved to obtain: X=5.4883, Y=79.3564

The equation set 2 is solved to obtain: X=1.8282, Y=75.0104

It is obtained that the dose limits of the etoposide (A) of the additive effect is 1.8282-5.4883 μg/ml. According to a combined relationship of A:B:C=12.5:2:45, it is very easy to obtain dose ranges of the additive effect of the A+B+C:

Etoposide (A): 1.8282-5.4883 μg/ml;
Vincristine (B): 0.2925-0.8781 μg/ml;
5-fluorouracil (C): 6.5815-19.7579 μg/ml.

The etoposide (A), the vincristine (B) and the 5-fluorouracil (C) are in a common effect range in the combined use (A+B+C) and in the three-drug combined use at a fixed proportion A:B:C=12.5:2:45 (μg/ml+μg/ml+μg/ml).

Dose Range of the Synergistic Effect (A+B+C):
[0.00004768+0.00000763+0.00017166, 1.8282+0.2925+6.5815)μg/ml+ng/ml Dose Range of the Additive Effect (A+B+C):
[1.8282+0.2925+6.5815, 5.4883+0.8781+19.7579] μg/ml+ng/ml Dose Range of the Antagonistic Effect (A+B+C):
(5.4883+0.8781+19.7579, 12.5+2+45] μg/ml+ng/ml Range belonging to the additive effect in the dose-effect curve of the actual effect of the combined group: 75.0104%-79.3564%

[3] the $CI_d s$ and the $CI_e s$ are calculated (ignored).

Part 2: quantitative calculation of synergistic, additive and antagonistic effects of other several three-drug combinations, including:

1) etoposide (A), vincristine (B) and adriamycin (D) combination at a fixed proportion A:B:D=12.5:2:4 (μg/ml);
2) etoposide (A), 5-fluorouracil (C) and adriamycin (D) combination at a fixed proportion A:C:D=12.5:45:4 (μg/ml);
3) vincristine (B), 5-fluorouracil (C) and adriamycin (D) combination at a fixed proportion B:C:D=2:45:4 (μg/ml).

Figure 10:
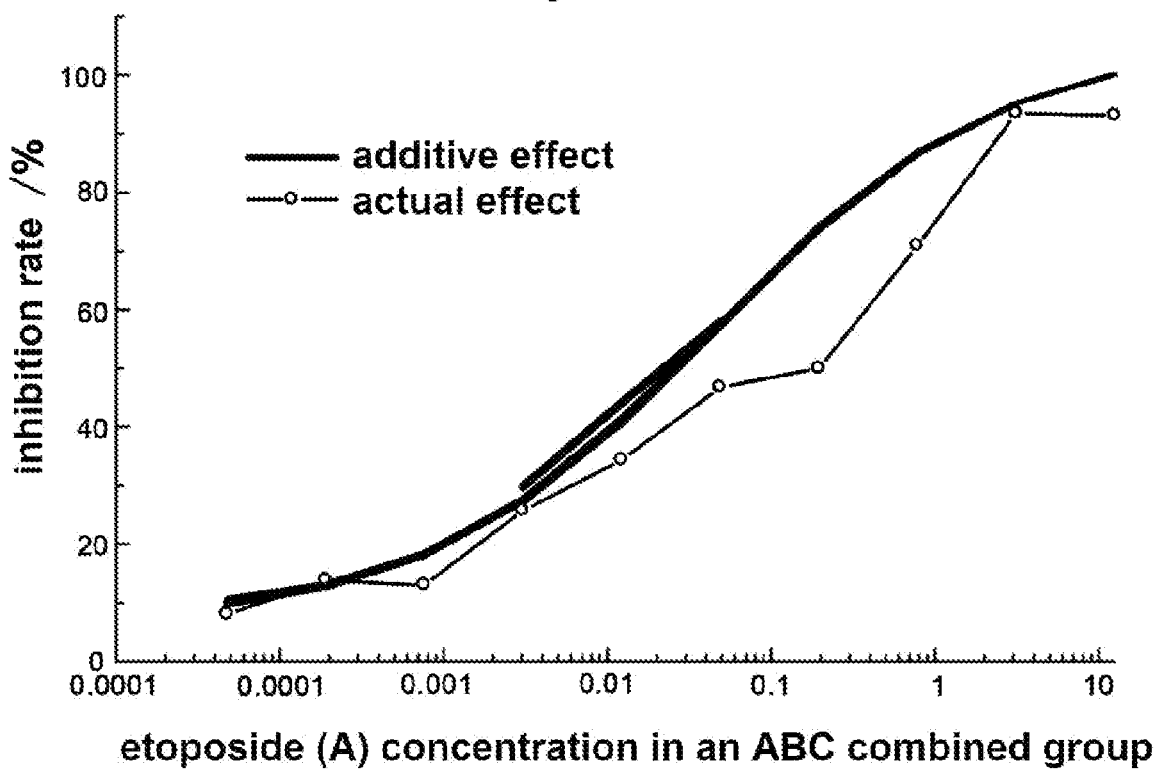
FIG. 10 illustrates a comparison diagram of an expected additive effect and an actual effect of A, B and D combined groups at a fixed proportion of A:B:D=12.5:2:4 (μg/ml) in a second embodiment of the present disclosure.

The calculation steps are the same as the calculation of the A+B+C combination in the part 1 (the calculation procedures are ignored), and the main results are as follows:

The dose-effect curve band and the actual dose-effect curve of the expected additive effect reconstructed in the A:B:D combined group is as shown in FIG. 10.

Figure 11:
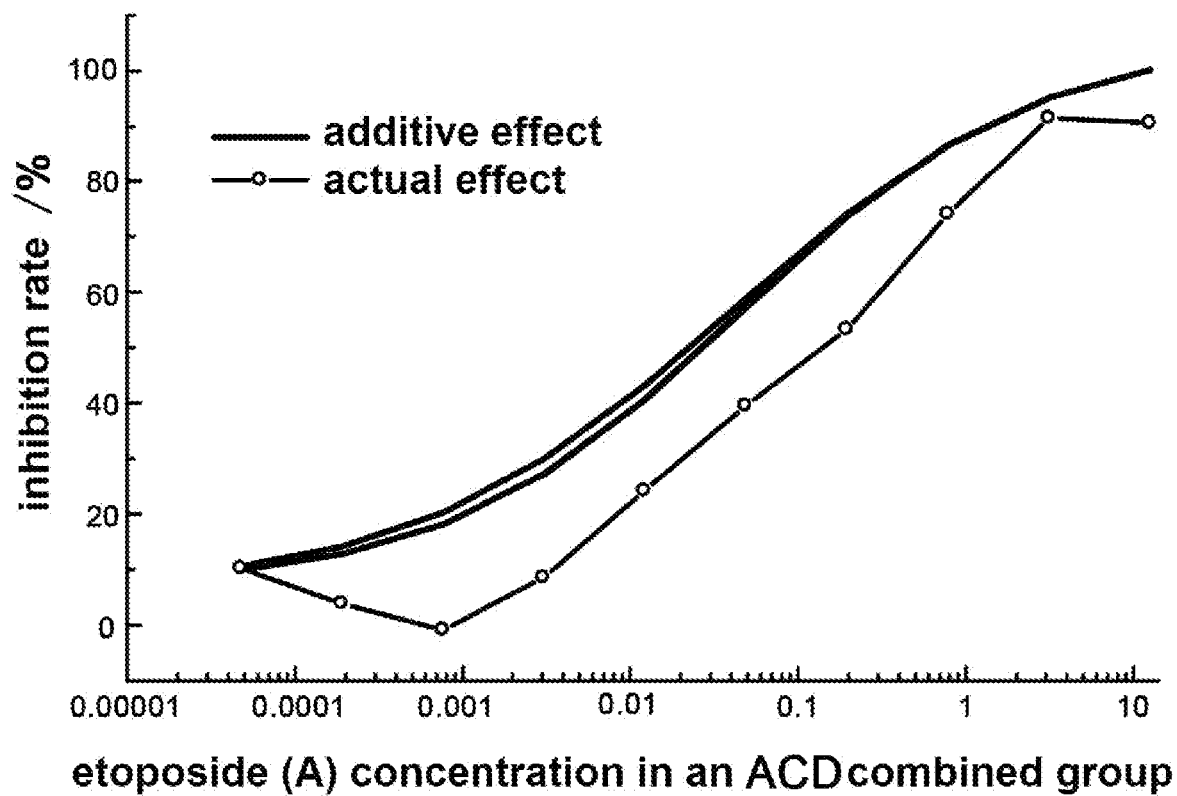
FIG. 11 illustrates a comparison diagram of an expected additive effect and an actual effect of A, C and D combined groups at a fixed proportion of A:C:D=12.5:45:4 (μg/ml) in a second embodiment of the present disclosure.

The dose-effect curve band and the actual dose-effect curve of the expected additive effect reconstructed in the A:C:D combined group is as shown in FIG. 11.

Figure 12:
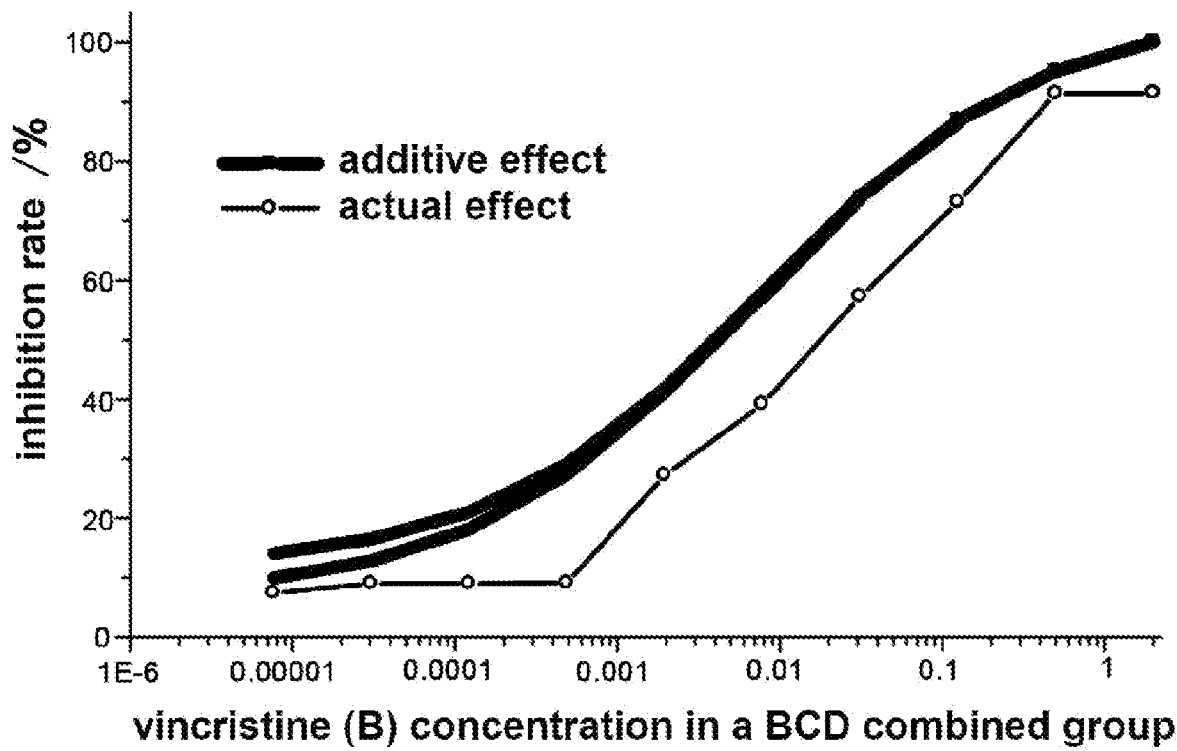
FIG. 12 illustrates a comparison diagram of an expected additive effect and an actual effect of B, C and D combined groups at a fixed proportion of B:C:D=2:45:4 (μg/ml) in a second embodiment of the present disclosure.

The dose-effect curve band and the actual dose-effect curve of the expected additive effect reconstructed in the B:C:D combined group is as shown in FIG. 12.

It may be seen from the FIG. 10, FIG. 11 and FIG. 12 that when A:B:D, A:C:D and B:C:D are combined at a fixed proportion, the dose-effect curves of the actual effect are substantially lower than the expected additive effect curve band and most belong to the range of the antagonistic effect.

Comprehensive evaluation: under existing compatibility condition, when any three of the four drugs are combined, those combined with the adriamycin will generate the antagonistic effect. And only the A+B+C are combined, the synergetic effect can be generated.

The foregoing descriptions are merely preferred embodiments of the present disclosure, but not to limit the present disclosure. A person of ordinary skill in the art may make various changes and variations. Any modification, equivalent replacement, improvement and the like make within the spirit and principle of the present disclosure shall be included in a scope of protection of the present disclosure.

What is claimed is:

1. A method for detecting efficacy of a combined drug, comprising:

administering each component drug in the combined drug to patients, recording the drug effect, preparing a dose-effect relationship table of dose levels of each component drug, fitting a respective dose-effect relationship curve equation, converting the dose sequentially, and calculating each dose-effect relationship data formed into an expected additive efficacy curve band under a combined condition, obtaining a dose-effect curve band of an expected additive effect of the combined drug, wherein the dose-effect curve band is enclosed by two equivalent dose-effect curves at the most periphery in multiple equivalent dose-effect curves, each of the equivalent dose-effect curves is a curve established by taking a dose of one target component drug in the combined drug as a horizontal coordinate and an expected additive effect obtained by equivalently converting the combined drug into any component drug as a vertical coordinate, and the equivalent conversion is performed according to a drug sequence of each component drug in the obtained combined drug; wherein the combined drug comprises nitrohydroxyl compound and Taxol, or the combined drug comprising etoposide, vincristine, 5-fluorouracil and adriamycin, the patients are patients with hepatocellular carcinoma or lung cancer;

administering each component drug in the combined drug, the combined drug with each component drug combined at a fixed proportion, and the combined drug with a dose change of the one target component drug in the combined drug to patients, recording the drug effect, and obtaining an actual dose-effect relationship curve formed by an actual effect value of the combined drug with a dose change of the one target component drug in the combined drug;

comparing a positional relationship between the actual dose-effect relationship curve and the dose-effect curve band; and determining the efficacy of the combined drug as a synergistic effect when the actual dose-effect relationship curve is located above the dose-effect curve band, determining the efficacy of the combined drug as an antagonistic effect when the actual dose-effect relationship curve is located below the dose-effect curve band, and determining the efficacy of the combined drug as an additive effect when the actual dose-effect relationship curve is located within a range of the dose-effect curve band;

the step of comparing the positional relationship between the actual dose-effect relationship curve and the dose-effect curve band comprises:

obtaining a minimum value and a maximum value of an expected additive effect of a corresponding combined drug in a range of the dose-effect curve band under a specific combined dose of the one target component drug;

obtaining an actual effect value of the corresponding combined drug on the actual dose-effect relationship curve under the specific combined dose of the one target component drug;

calculating a first ratio of the actual effect value to the minimum value of the expected additive effect;

calculating a second ratio of the actual effect value to the maximum value of the expected additive effect;

respectively labeling the first ratio and the second ratio as $CI_{d1}$ and $CI_{d2}$;

if the $CI_{d1}$ and the $CI_{d2}$ both are greater than 1, determining that the actual dose-effect relationship curve is located above the dose-effect curve band;

if the $CI_{d1}$ and the $CI_{d2}$ both are smaller than 1, determining that the actual dose-effect relationship curve is located below the dose-effect curve band; and if either the $CI_{d1}$ or the $CI_{d2}$ is greater than or equal to 1 or is smaller than or equal to 1, determining that the actual dose-effect relationship curve is located within the range of the dose-effect curve band.

2. The method as claimed in claim 1, wherein the combined drug comprises a first component drug A and a second component drug B; before the step of obtaining the dose-effect curve band of the expected additive effect of the combined drug, the method further comprises a step of establishing multiple equivalent dose-effect curves, wherein the step of establishing the multiple equivalent dose-effect curves comprises:

obtaining a first dose-effect relationship curve $Y=f(x)$ of the first component drug A;

obtaining a second dose-effect relationship curve $Y=g(x)$ of the second component drug B;

finding or calculating an effect value $f(Am)$ of the first component drug A under a combined dose Am on the first dose-effect relationship curve $Y=f(x)$;

finding or calculating an equivalent dose value Bm same as the effect value $f(Am)$ and corresponding to an effect value $g(Bm)$ of the second component drug B on the second dose-effect relationship curve $Y=g(x)$;

calculating a dose sum (Bn+Bm) of a combined dose Bn and the equivalent dose Bm of the second component drug B;

finding or calculating a corresponding effect value $g(Bn+Bm)$ when the dose of the second component drug B on the second dose-effect relationship curve $Y=g(x)$ is the dose sum (Bn+Bm);

converting the effect value $g(Bn+Bm)$ into an expected additive effect value $Y(Am+Bn)$ of the combined drug;

establishing a first equivalent dose-effect curve $Y(Am+Bn)=g(Bn+Bm)$ of the expected additive effect value of the combined drug with a dose change of the first component drug A;

finding or calculating an effect value $g(Bn)$ of the second component drug B under a combined dose Bn on the second dose-effect relationship curve $Y=g(x)$;

finding or calculating an equivalent dose value An same as the effect value $g(Bn)$ and corresponding to an effect value $f(An)$ of the first component drug A on the first dose-effect relationship curve $Y=f(x)$;

calculating a dose sum (Am+An) of a combined dose Am and the equivalent dose An of the first component drug A;

finding or calculating a corresponding effect value $f(Am+An)$ when the dose of the first component drug A on the first dose-effect relationship curve $Y=f(x)$ is the dose sum (Am+An);

converting the effect value $f(Am+An)$ into the expected additive effect value $Y(Am+Bn)$ of the combined drug; and establishing a second equivalent dose-effect curve $Y(Am+Bn)=f(Am+An)$ of the expected additive effect value of the combined drug with the dose change of the first component drug A.

3. The method as claimed in claim 1, wherein when the efficacy output result of the combined drug is the synergistic effect, after the step of outputting the efficacy of the combined drug as the synergistic effect, the method further comprises:

calculating a corresponding first dose range of the one target component drug when the actual dose-effect relationship curve is located above the dose-effect curve band; and outputting the first dose range as a synergistic dose range of the one target component drug.

4. The method as claimed in claim 3, wherein after outputting the synergistic dose range of the one target component drug, the method further comprises:

obtaining a combined relationship between the one target component drug and rest component drugs in the combined drug;

calculating synergistic dose ranges of the rest component drugs in the combined drug under a combined condition according to the combined relationship; and outputting the synergistic dose ranges of the rest component drugs.

5. The method as claimed in claim 1, wherein when the efficacy output result of the combined drug is the antagonistic effect, after the step of outputting the efficacy of the combined drug as the antagonistic effect, the method further comprises:

calculating a corresponding second dose range of the one target component drug when the actual dose-effect relationship curve is located below the dose-effect curve band; and outputting the second dose range as an antagonistic dose range of the one target component drug.

6. The method as claimed in claim 5, wherein after outputting the antagonistic dose range of the one target component drug, the method further comprises:

obtaining a combined relationship between the one target component drug and rest component drugs in the combined drug;

calculating antagonistic dose ranges of the rest component drugs in the combined drug under a combined condition according to the combined relationship; and outputting the antagonistic dose ranges of the rest component drugs.

7. The method as claimed in claim 1, wherein when the efficacy output result of the combined drug is the additive effect, after the step of outputting the efficacy of the combined drug as the additive effect, the method further comprises:

calculating a corresponding third dose range of the one target component drug when the actual dose-effect relationship curve is located within the range of the dose-effect curve band;

and outputting the third dose range as an additive dose range of the one target component drug.

8. The method as claimed in claim 7, wherein after outputting the additive dose range of the one target component drug, the method further comprises:

obtaining a combined relationship between the one target component drug and rest component drugs in the combined drug;

calculating additive dose ranges of the rest component drugs in the combined drug under a combined condition according to the combined relationship; and outputting the additive dose ranges of the rest component drugs.

9. The method as claimed in claim 1, after the step of respectively labeling the first ratio and the second ratio as the $CI_{d1}$ and the $CI_{d2}$, the method further comprises a step of outputting the $CI_{d1}$ and the $CI_{d2}$.

10. The method as claimed in claim 1, wherein the step of comparing the positional relationship between the actual dose-effect relationship curve and the dose-effect curve band comprises:

obtaining a minimum value and a maximum value of corresponding doses of the one target component drug when the combined drug generates a specific effect on the dose-effect curve band;

obtaining an actual combined dose required when the combined drug generates the specific effect on the actual dose-effect relationship curve;

calculating a third ratio of the actual combined dose to the minimum value;

calculating a fourth ratio of the actual combined dose to the maximum value;

respectively labeling the third ratio and the fourth ratio as $CI_{e1}$ and $CI_{e2}$;

if the $CI_{e1}$ and the $CI_{e2}$ both are smaller than 1, determining that the actual dose-effect relationship curve is located above the dose-effect curve band;

if the $CI_{e1}$ and the $CI_{e2}$ both are greater than 1, determining that the actual dose-effect relationship curve is located below the dose-effect curve band; and if either the $CI_{e1}$ or the $CI_{e2}$ is greater than or equal to 1 or is smaller than or equal to 1, determining that the actual dose-effect relationship curve is located within the range of the dose-effect curve band;

after the step of respectively labeling the third ratio and the fourth ratio as the $CI_{e1}$ and the $CI_{e2}$, the method further comprises a step of outputting the $CI_{e1}$ and the $CI_{e2}$.

11. A method for preventing or treating disease by a combined drug, comprising:

screening a combined drug with a synergistic effect or an antagonistic effect, and administering the combined drug with a synergistic effect or an antagonistic effect to patients, wherein screening a combined drug with a synergistic effect or an antagonistic effect comprises:

administering each component drug in the combined drug to patients, recording the drug effect, preparing a dose-effect relationship table of dose levels of each component drug, fitting a respective dose-effect relationship curve equation, converting the dose sequentially, and calculating each dose-effect relationship data formed into an expected additive efficacy curve band under a combined condition, obtaining a dose-effect curve band of an expected additive effect of the combined drug, wherein the dose-effect curve band is enclosed by two equivalent dose-effect curves at the most periphery in multiple equivalent dose-effect curves, each of the equivalent dose-effect curves is a curve established by taking a dose of one target component drug in the combined drug as a horizontal coordinate and an expected additive effect obtained by equivalently converting the combined drug into any component drug as a vertical coordinate, and the equivalent conversion is performed according to a drug sequence of each component drug in the obtained combined drug; wherein the combined drug comprises nitrohydroxyl compound and Taxol, or the combined drug comprising etoposide, vincristine, 5-fluorouracil and adriamycin, the patients are patients with hepatocellular carcinoma or lung cancer;

administering each component drug in the combined drug, the combined drug with each component drug combined at a fixed proportion, and the combined drug with a dose change of the one target component drug in the combined drug to patients, recording the drug effect, and obtaining an actual dose-effect relationship curve formed by an actual effect value of the combined drug with a dose change of the one target component drug in the combined drug;

comparing a positional relationship between the actual dose-effect relationship curve and the dose-effect curve band; and determining the efficacy of the combined drug as a synergistic effect when the actual dose-effect relationship curve is located above the dose-effect curve band, determining the efficacy of the combined drug as an antagonistic effect when the actual dose-effect relationship curve is located below the dose-effect curve band, and determining the efficacy of the combined drug as an additive effect when the actual dose-effect relationship curve is located within a range of the dose-effect curve band;

the step of comparing the positional relationship between the actual dose-effect relationship curve and the dose-effect curve band comprises:

obtaining a minimum value and a maximum value of an expected additive effect of a corresponding combined drug in a range of the dose-effect curve band under a specific combined dose of the one target component drug;

obtaining an actual effect value of the corresponding combined drug on the actual dose-effect relationship curve under the specific combined dose of the one target component drug;

calculating a first ratio of the actual effect value to the minimum value of the expected additive effect;

calculating a second ratio of the actual effect value to the maximum value of the expected additive effect;

respectively labeling the first ratio and the second ratio as $CI_{d1}$ and $CI_{d2}$;

if the $CI_{d1}$ and the $CI_{d2}$ both are greater than 1, determining that the actual dose-effect relationship curve is located above the dose-effect curve band;

if the $CI_{d1}$ and the $CI_{d2}$ both are smaller than 1, determining that the actual dose-effect relationship curve is located below the dose-effect curve band; and if either the $CI_{d1}$ or the $CI_{d2}$ is greater than or equal to 1 or is smaller than or equal to 1, determining that the actual dose-effect relationship curve is located within the range of the dose-effect curve band.

12. The method as claimed in claim 11, wherein the combined drug comprises a first component drug A and a second component drug B; before the step of obtaining the dose-effect curve band of the expected additive effect of the combined drug, the method further comprises a step of establishing multiple equivalent dose-effect curves, wherein the step of establishing the multiple equivalent dose-effect curves comprises:

obtaining a first dose-effect relationship curve Y=f(x) of the first component drug A;

obtaining a second dose-effect relationship curve Y=g(x) of the second component drug B;

finding or calculating an effect value f(Am) of the first component drug A under a combined dose Am on the first dose-effect relationship curve Y=f(x);

finding or calculating an equivalent dose value Bm same as the effect value f(Am) and corresponding to an effect value g(Bm) of the second component drug B on the second dose-effect relationship curve Y=g(x);

calculating a dose sum (Bn+Bm) of a combined dose Bn and the equivalent dose Bm of the second component drug B;

finding or calculating a corresponding effect value g(Bn+Bm) when the dose of the second component drug B on the second dose-effect relationship curve Y=g(x) is the dose sum (Bn+Bm);

converting the effect value g(Bn+Bm) into an expected additive effect value Y(Am+Bn) of the combined drug;

establishing a first equivalent dose-effect curve Y(Am+Bn)=g(Bn+Bm) of the expected additive effect value of the combined drug with a dose change of the first component drug A;

finding or calculating an effect value g(Bn) of the second component drug B under a combined dose Bn on the second dose-effect relationship curve Y=g(x);

finding or calculating an equivalent dose value An same as the effect value g(Bn) and corresponding to an effect value f(An) of the first component drug A on the first dose-effect relationship curve Y=f(x);

calculating a dose sum (Am+An) of a combined dose Am and the equivalent dose An of the first component drug A;

finding or calculating a corresponding effect value f(Am+An) when the dose of the first component drug A on the first dose-effect relationship curve Y=f(x) is the dose sum (Am+An);

converting the effect value f(Am+An) into the expected additive effect value Y(Am+Bn) of the combined drug; and establishing a second equivalent dose-effect curve Y(Am+Bn)=f(Am+An) of the expected additive effect value of the combined drug with the dose change of the first component drug A.

13. The method as claimed in claim 11, wherein when the efficacy output result of the combined drug is the synergistic effect, after the step of outputting the efficacy of the combined drug as the synergistic effect, the method further comprises:

calculating a corresponding first dose range of the one target component drug when the actual dose-effect relationship curve is located above the dose-effect curve band; and outputting the first dose range as a synergistic dose range of the one target component drug.

14. The method as claimed in claim 13, wherein after outputting the synergistic dose range of the one target component drug, the method further comprises:

obtaining a combined relationship between the one target component drug and rest component drugs in the combined drug;

calculating synergistic dose ranges of the rest component drugs in the combined drug under a combined condition according to the combined relationship; and outputting the synergistic dose ranges of the rest component drugs.

15. The method as claimed in claim 11, wherein when the efficacy output result of the combined drug is the antagonistic effect, after the step of outputting the efficacy of the combined drug as the antagonistic effect, the method further comprises:

calculating a corresponding second dose range of the one target component drug when the actual dose-effect relationship curve is located below the dose-effect curve band; and outputting the second dose range as an antagonistic dose range of the one target component drug.

16. The method as claimed in claim 15, wherein after outputting the antagonistic dose range of the one target component drug, the method further comprises:

obtaining a combined relationship between the one target component drug and rest component drugs in the combined drug;

calculating antagonistic dose ranges of the rest component drugs in the combined drug under a combined condition according to the combined relationship; and outputting the antagonistic dose ranges of the rest component drugs.

17. The method as claimed in claim 11, wherein when the efficacy output result of the combined drug is the additive effect, after the step of outputting the efficacy of the combined drug as the additive effect, the method further comprises:

calculating a corresponding third dose range of the one target component drug when the actual dose-effect relationship curve is located within the range of the dose-effect curve band;

and outputting the third dose range as an additive dose range of the one target component drug.

18. The method as claimed in claim 17, wherein after outputting the additive dose range of the one target component drug, the method further comprises:

obtaining a combined relationship between the one target component drug and rest component drugs in the combined drug;

calculating additive dose ranges of the rest component drugs in the combined drug under a combined condition according to the combined relationship; and outputting the additive dose ranges of the rest component drugs.

19. The method as claimed in claim 11, after the step of respectively labeling the first ratio and the second ratio as the $CI_{d1}$ and the $CI_{d2}$, the method further comprises a step of outputting the $CI_{d1}$ and the $CI_{d2}$.

20. The method as claimed in claim 11, wherein the step of comparing the positional relationship between the actual dose-effect relationship curve and the dose-effect curve band comprises:

obtaining a minimum value and a maximum value of corresponding doses of the one target component drug when the combined drug generates a specific effect on the dose-effect curve band;

obtaining an actual combined dose required when the combined drug generates the specific effect on the actual dose-effect relationship curve;

calculating a third ratio of the actual combined dose to the minimum value;

calculating a fourth ratio of the actual combined dose to the maximum value;

respectively labeling the third ratio and the fourth ratio as $CI_{e1}$ and $CI_{e2}$;

if the $CI_{e1}$ and the $CI_{e2}$ both are smaller than 1, determining that the actual dose-effect relationship curve is located above the dose-effect curve band;

if the $CI_{e1}$ and the $CI_{e2}$ both are greater than 1, determining that the actual dose-effect relationship curve is located below the dose-effect curve band; and if either the $CI_{e1}$ or the $CI_{e2}$ is greater than or equal to 1 or is smaller than or equal to 1, determining that the actual dose-effect relationship curve is located within the range of the dose-effect curve band;

after the step of respectively labeling the third ratio and the fourth ratio as the $CI_{e1}$ and the $CI_{e2}$, the method further comprises a step of outputting the $CI_{e1}$ and the $CI_{e2}$.

* * * * *